US010220089B2

(12) United States Patent
Hsiao et al.

(10) Patent No.: US 10,220,089 B2
(45) Date of Patent: Mar. 5, 2019

(54) DIAGNOSIS AND TREATMENT OF AUTISM SPECTRUM DISORDER

(71) Applicant: California Institute of Technology, Pasadena, CA (US)

(72) Inventors: Elaine Hsiao, Rowland Heights, CA (US); Sarkis K Mazmanian, Porter Ranch, CA (US); Paul H Patterson, Altadena, CA (US); Sara McBride, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/012,769

(22) Filed: Aug. 28, 2013

(65) Prior Publication Data
US 2014/0065132 A1 Mar. 6, 2014

Related U.S. Application Data

(60) Provisional application No. 61/694,679, filed on Aug. 29, 2012.

(51) Int. Cl.
A61K 39/395 (2006.01)
A61K 35/74 (2015.01)
A61K 35/741 (2015.01)
G01N 33/68 (2006.01)
C07K 16/18 (2006.01)
A61K 39/00 (2006.01)

(52) U.S. Cl.
CPC .......... A61K 39/3955 (2013.01); A61K 35/74 (2013.01); A61K 35/741 (2013.01); C07K 16/18 (2013.01); G01N 33/6896 (2013.01); A61K 2039/505 (2013.01); G01N 2800/28 (2013.01); G01N 2800/7076 (2013.01); G01N 2800/7085 (2013.01)

(58) Field of Classification Search
None
See application file for complete search history.

(56) References Cited

U.S. PATENT DOCUMENTS

| 5,443,826 | A | 8/1995 | Brody |
| 5,951,977 | A | 9/1999 | Nisbet et al. |
| 7,731,976 | B2 | 6/2010 | Cobb et al. |
| 7,749,509 | B2 | 7/2010 | Cobb et al. |
| 8,192,733 | B2 | 6/2012 | Cobb et al. |
| 9,452,189 | B2 | 9/2016 | Mazmanian et al. |
| 2002/0013270 | A1 | 1/2002 | Bolte |
| 2004/0005304 | A1 | 1/2004 | Brudnak |
| 2004/0028689 | A1 | 2/2004 | Borody |
| 2004/0170617 | A1 | 9/2004 | Finegold |
| 2006/0167057 | A1 | 7/2006 | Kong et al. |
| 2006/0177424 | A1 | 8/2006 | Cobb et al. |
| 2007/0280911 | A1 | 12/2007 | Cobb et al. |
| 2009/0118257 | A1 | 5/2009 | Jankowski et al. |
| 2010/0303782 | A1 | 12/2010 | Cobb et al. |
| 2011/0081320 | A1 | 4/2011 | Westall et al. |
| 2011/0118135 | A1 | 5/2011 | State et al. |
| 2012/0087895 | A1 | 4/2012 | Mazmanian et al. |
| 2012/0190055 | A1 | 7/2012 | Cezar et al. |
| 2012/0207726 | A1 | 8/2012 | Lipkin et al. |
| 2012/0237482 | A1 | 9/2012 | Rodriguez |
| 2012/0252775 | A1 | 10/2012 | Finegold |
| 2013/0115257 | A1 | 5/2013 | Gysemans et al. |
| 2013/0195802 | A1 | 8/2013 | Moore |
| 2015/0050246 | A1 | 2/2015 | Jones et al. |
| 2016/0120916 | A1 | 5/2016 | Hsaio et al. |
| 2016/0120917 | A1 | 5/2016 | Bailey et al. |
| 2016/0120920 | A1 | 5/2016 | Hsiao et al. |
| 2016/0193256 | A1 | 7/2016 | Honda et al. |
| 2016/0339065 | A1 | 11/2016 | Adams et al. |

FOREIGN PATENT DOCUMENTS

| CN | 104546932 A | 4/2015 |
| EP | 2 624 863 B1 | 4/2016 |
| EP | 3072524 | 9/2016 |
| JP | 2008-532033 | 8/2008 |
| WO | WO 9611014 | 4/1996 |
| WO | WO 99/19459 | 4/1999 |
| WO | WO 02/07741 | 1/2002 |
| WO | WO 2006/090185 A1 | 8/2006 |
| WO | WO2006090185 | 8/2006 |
| WO | WO2006/110406 | 10/2006 |
| WO | WO2009/055362 | 4/2008 |
| WO | WO2010/056985 A2 | 5/2010 |
| WO | WO 2011/044516 | 4/2011 |
| WO | WO2011139914 | 11/2011 |
| WO | WO2012/048152 | 4/2012 |
| WO | WO 2013/154725 | 10/2013 |
| WO | WO 2014/036182 | 3/2014 |
| WO | WO 2014/121301 | 8/2014 |
| WO | WO 2014/121304 | 8/2014 |

(Continued)

OTHER PUBLICATIONS

Round et al.: "Coordination of tolerogenic immune responses by the commensal microbiota." J. Autoimmun., 34:J220-225 (2010).
Office Action dated Nov. 21, 2013 for U.S. Appl. No. 13/267,748, filed Oct. 6, 2011.
Campbell et al., Bacterial diversity, community structure and potential growth rates along an estuarine salinity gradient, *Isme J*, (2012).
Grenham, G. Clarke, J. F. Cryan, T. G. Dinan, Brain-gut-microbe communication in health and disease. *Front Physiol* 2, 94 (Dec. 7, 2011).
Gulati et al., Mouse Background Strain Profoundly Influences Paneth Cell Function and Intestinal Microbial Composition, *PLoS One* 7, e32403 (2012).

(Continued)

*Primary Examiner* — Olga N Chernyshev
(74) *Attorney, Agent, or Firm* — Knobbe, Martens, Olson & Bear, LLP

(57) ABSTRACT

Disclosed herein are compositions, systems, and methods for diagnosing and treatment of subjects suffering from anxiety, autism spectrum disorder (ASD), or a pathological condition with one or more of the symptoms of ASD.

11 Claims, 37 Drawing Sheets
Specification includes a Sequence Listing.

(56) References Cited

FOREIGN PATENT DOCUMENTS

| WO | WO2015/181449 A1 | 12/2015 |
| WO | WO2016/069792 | 5/2016 |
| WO | WO2016/069801 | 5/2016 |
| WO | WO 2016/110768 A1 | 7/2016 |
| WO | WO2017/205302 A1 | 11/2017 |
| WO | WO 2017/220708 | 12/2017 |

OTHER PUBLICATIONS

Lee et al., in *International Meeting for Autism Research* (Toronto, Canada, May 17-19, 2012).

Smith et al., Host Genetics and Environmental Factors Regulate Ecological Succession of the Mouse Colon Tissue-Associated Microbiota, *PLoS One* 7, e30273 (Jan. 2012).

Adams et al. (2011). Gastrointestinal flora and gastrointestinal status in children with autism—comparisons to typical children and correlation with autism severity. BMC Gastroenterol 11, 22.

Al-Asmakh et al. (2012). Gut microbial communities modulating brain development and function. Gut Microbes 3, 366-373.

Altieri et al. (2011). Urinary p-cresol is elevated in small children with severe autism spectrum disorder. Biomarkers 16, 252-260.

Amaral et al. (2008). Commensal microbiota is fundamental for the development of inflammatory pain. Proc Natl Acad Sci U S A 105, 2193-2197.

Amasheh et al. (2009). Na+ absorption defends from paracellular back-leakage by claudin-8 upregulation. Biochem Biophys Res Commun 378, 45-50.

Atladottir, et al. (2010). Maternal infection requiring hospitalization during pregnancy and autism spectrum disorders. J Autism Dev Disord 40, 1423-1430.

Bercik et al. (2011). The anxiolytic effect of Bifidobacterium longum NCC3001 involves vagal pathways for gut-brain communication. Neurogastroenterol Motil 23, 1132-1139.

Blumberg, R., and Powrie, F. (2012). Microbiota, disease, and back to health: a metastable journey. Sci Transl Med 4, 137rv137.

Boksa, P. (2010). Effects of prenatal infection on brain development and behavior: a review of findings from animal models. Brain Behav Immun 24, 881-897.

Bourin et al. (2007). Animal models of anxiety in mice. Fundamental & clinical pharmacology 21, 567-574.

Bravo et al. (2011). Ingestion of Lactobacillus strain regulates emotional behavior and central GABA receptor expression in a mouse via the vagus nerve. Proc Natl Acad Sci U S A 108, 16050-16055.

Breiman, L. (2001). Random forests. Mach Learn 45, 5-32.

Brown, et al. (2000). Stress produced by gavage administration in the rat. Contemporary topics in laboratory animal science / American Association for Laboratory Animal Science 39, 17-21.

Buie, et al. (2010). Evaluation, diagnosis, and treatment of gastrointestinal disorders in individuals with ASDs: a consensus report. Pediatrics 125 Suppl 1, S1-18.

Bull et al. (2003). Indolyl-3-acryloylglycine (IAG) is a putative diagnostic urinary marker for autism spectrum disorders. Med Sci Monit 9, CR422-425.

Burlingham et al. (2003). 34S isotope effect on sulfate ester hydrolysis: mechanistic implications. J Am Chem Soc 125, 13036-13037.

Canitano, R., and Scandurra, V. (2008). Risperidone in the treatment of behavioral disorders associated with autism in children and adolescents. Neuropsychiatr Dis Treat 4, 723-730.

Caporaso et al. (2010). PyNAST: a flexible tool for aligning sequences to a template alignment. Bioinformatics 26, 266-267.

CDC (2012). Prevalence of autism spectrum disorders—autism and developmental disabilities monitoring network, 14 sites, United States, 2008. MMWR Surveill Summ 61, 1-19.

Clemente et al. (2012). The impact of the gut microbiota on human health: an integrative view. Cell 148, 1258-1270.

Cohen-Poradosu et al. (2011). Bacteroides fragilis-stimulated interleukin-10 contains expanding disease. The Journal of infectious diseases 204, 363-371.

Collins et al. (2012). The interplay between the intestinal microbiota and the brain. Nat Rev Microbiol 10, 735-742.

Coury, et al. (2012). Gastrointestinal conditions in children with autism spectrum disorder: developing a research agenda. Pediatrics 130 Suppl 2, S160-168.

Critchfield, et al. (2011). The potential role of probiotics in the management of childhood autism spectrum disorders. Gastroenterology research and practice 2011, 161358.

Cryan, J.F., and Dinan, T.G. (2012). Mind-altering microorganisms: the impact of the gut microbiota on brain and behaviour. Nat Rev Neurosci 13, 701-712.

D'Eufemia, et al. (1996). Abnormal intestinal permeability in children with autism. Acta Paediatr 85, 1076-1079.

De Hoon et al. (2004). Open source clustering software. Bioinformatics 20, 1453-1454.

De Magistris et al. (2010). Alterations of the intestinal barrier in patients with autism spectrum disorders and in their first-degree relatives. J Pediatr Gastroenterol Nutr 51, 418-424.

Desbonnet, et al. (2013). Microbiota is essential for social development in the mouse. Molecular psychiatry.

Edgar, R.C. (2010). Search and clustering orders of magnitude faster than BLAST. Bioinformatics 26, 2460-2461.

Edgar, et al. (2011). UCHIME improves sensitivity and speed of chimera detection. Bioinformatics 27, 2194-2200.

Ewaschuk, et al. (2008). Secreted bioactive factors from Bifidobacterium infantis enhance epithelial cell barrier function. Am J Physiol Gastrointest Liver Physiol 295, G1025-1034.

Faith, D.P. (1992). Conservation Evaluation and Phylogenetic Diversity. Biol Conserv 61, 1-10.

Finegold, S.M. (2011). Desulfovibrio species are potentially important in regressive autism. Medical hypotheses 77, 270-274.

Finegold, et al. (2010). Pyrosequencing study of fecal microflora of autistic and control children. Anaerobe 16, 444-453.

Finegold, et al. (2012). Microbiology of regressive autism. Anaerobe 18, 260-262.

Finegold, et al. (2002). Gastrointestinal microflora studies in late-onset autism. Clin Infect Dis 35, S6-S16.

Frye, et al. (2013). Unique acyl-carnitine profiles are potential biomarkers for acquired mitochondrial disease in autism spectrum disorder. Translational psychiatry 3, e220.

Geyer, M.A., and Swerdlow, N.R. (2001). Measurement of startle response, prepulse inhibition, and habituation. Curr Protoc Neurosci Chapter 8, Unit 8 7.

Gondalia, et al. (2012). Molecular characterisation of gastrointestinal microbiota of children with autism (with and without gastrointestinal dysfunction) and their neurotypical siblings. Autism Res 5, 419-427.

Gorrindo, et al. (2013). Enrichment of elevated plasma f2t-isoprostane levels in individuals with autism who are stratified by presence of gastrointestinal dysfunction. PLoS One 8, e68444.

Gorrindo, et al. (2012). Gastrointestinal dysfunction in autism: parental report, clinical evaluation, and associated factors. Autism Res 5, 101-108.

Grimes, A.J. (1959). Synthesis of 35S-labelled arylsulphates by intact animals and by tissue preparations, with particular reference to I-tyrosine O-sulphate. Biochem J 73, 723.

Grimsley, et al. (2011). Development of social vocalizations in mice. PloS one 6, e17460.

Hallmayer, et al. (2011). Genetic heritability and shared environmental factors among twin pairs with autism. Arch Gen Psychiatry 68, 1095-1102.

Han, et al. (2012). Autistic-like behaviour in Scn1a+/− mice and rescue by enhanced GABA-mediated neurotransmission. Nature 489, 385-390.

Heijtz, et al. (2011). Normal gut microbiota modulates brain development and behavior. Proc Natl Acad Sci U S A 108, 3047-3052.

Hering, et al. (2012). Determinants of colonic barrier function in inflammatory bowel disease and potential therapeutics. The Journal of physiology 590, 1035-1044.

Holmes, et al. (2006). Claudin profiling in the mouse during postnatal intestinal development and along the gastrointestinal tract reveals complex expression patterns. Gene Expr Patterns 6, 581-588.

(56) References Cited

OTHER PUBLICATIONS

Hooper, et al. (2012). Interactions between the microbiota and the immune system. Science 336, 1268-1273.
Horvath, K., and Perman, J.A. (2002). Autism and gastrointestinal symptoms. Curr Gastroenterol Rep 4, 251-258.
Hsiao, et al. (2012). Modeling an autism risk factor in mice leads to permanent immune dysregulation. Proc Natl Acad Sci U S A 109, 12776-12781.
Hsiao, E.Y., and Patterson, P.H. (2011). Activation of the maternal immune system induces endocrine changes in the placenta via IL-6. Brain Behav Immun 25, 604-615.
Huang, et al. (2011). The human commensal Bacteroides fragilis binds intestinal mucin. Anaerobe 17, 137-141.
Ibrahim, et al. (2009). Incidence of gastrointestinal symptoms in children with autism: a population-based study. Pediatrics 124, 680-686.
Kang, et al. (2013). Reduced Incidence of and Other Fermenters in Intestinal Microflora of Autistic Children. PLoS One 8, e68322.
Kau, et al. (2011). Human nutrition, the gut microbiome and the immune system. Nature 474, 327-336.
Keszthelyi, et al. (2009). Understanding the role of tryptophan and serotonin metabolism in gastrointestinal function. Neurogastroenterol Motil 21, 1239-1249.
Knights, et al. (2011). Supervised classification of human microbiota. FEMS microbiology reviews 35, 343-359.
Koenig, et al. (2011). Succession of microbial consortia in the developing infant gut microbiome. Proc Natl Acad Sci U S A 108 Suppl 1, 4578-4585.
Kohane, et al. (2012). The co-morbidity burden of children and young adults with autism spectrum disorders. PLoS One 7, e33224.
Korosi, et al. (2012). Early-life stress mediated modulation of adult neurogenesis and behavior. Behav Brain Res 227, 400-409.
Kursa, M.B., and Rudnicki, W.R. (2010). Feature Selection with the Boruta Package. J Stat Softw 36, 1-13.
Lafaye, et al. (2004). Profiling of sulfoconjugates in urine by using precursor ion and neutral loss scans in tandem mass spectrometry. Application to the investigation of heavy metal toxicity in rats. J Mass Spectrom 39, 655-664.
Lazic, S.E. (2013). Comment on "Stress in puberty unmasks latent neuropathological consequences of prenatal immune activation in mice". Science 340, 811; discussion 811.
Leatham, et al. (2009). Precolonized human commensal *Escherichia coli* strains serve as a barrier to *E. coli* O157:H7 growth in the streptomycin-treated mouse intestine. Infect Immun 77, 2876-2886.
Lee, A., and Gemmell, E. (1972). Changes in the mouse intestinal microflora during weaning: role of volatile fatty acids. Infect Immun 5, 1-7.
Lozupone, C., and Knight, R. (2005). UniFrac: a new phylogenetic method for comparing microbial communities. Appl Environ Microbiol 71, 8228-8235.
Ludwig, et al. (2004). ARB: a software environment for sequence data. Nucleic Acids Res 32, 1363-1371.
MacFabe, D.F. (2012). Short-chain fatty acid fermentation products of the gut microbiome: implications in autism spectrum disorders. Microbial Ecology in Health & Disease 23, 19260.
Malkova, et al. (2012). Maternal immune activation yields offspring displaying mouse versions of the three core symptoms of autism. Brain Behav Immun 26, 607-616.
Mandel, et al. (2011). Maternal immune stimulation during pregnancy affects adaptive immunity in offspring to promote development of TH17 cells. Brain Behav Immun 25, 863-871.
Matsumoto, et al. (2012). Impact of intestinal microbiota on intestinal luminal metabolome. Sci Rep 2, 233.
Mayer, E.A. (2011). Gut feelings: the emerging biology of gut-brain communication. Nat Rev Neurosci 12, 453-466.
Mazmanian, et al. (2008). A microbial symbiosis factor prevents intestinal inflammatory disease. Nature 453, 620-625.
Mazurek, et al. (2013). Anxiety, sensory over-responsivity, and gastrointestinal problems in children with autism spectrum disorders. J Abnorm Child Psychol 41, 165-176.
Ming, et al. (2012b). Metabolic perturbance in autism spectrum disorders: a metabolomics study. Journal of proteome research 11, 5856-5862.
Mulder, et al. (2004). Platelet serotonin levels in pervasive developmental disorders and mental retardation: diagnostic group differences, within-group distribution, and behavioral correlates. J Am Acad Child Adolesc Psychiatry 43, 491-499.
Nicholson, et al. (2012). Host-gut microbiota metabolic interactions. Science 336, 1262-1267.
Nikolov, et al. (2009). Gastrointestinal symptoms in a sample of children with pervasive developmental disorders. J Autism Dev Disord 39, 405-413.
Novarino, et al. (2012). Mutations in BCKD-kinase lead to a potentially treatable form of autism with epilepsy. Science 338, 394-397.
O'Mahony, et al. (2009). Early life stress alters behavior, immunity, and microbiota in rats: implications for irritable bowel syndrome and psychiatric illnesses. Biological psychiatry 65, 263-267.
Ochoa-Reparaz, et al. (2010). Central nervous system demyelinating disease protection by the human commensal Bacteroides fragilis depends on polysaccharide A expression. J Immunol 185, 4101-4108.
Odamaki, et al. (2008). Distribution of different species of the Bacteroides fragilis group in individuals with Japanese cedar pollinosis. Appl Environ Microbiol 74, 6814-6817.
Onore, et al. (2012). The role of immune dysfunction in the pathophysiology of autism. Brain Behav Immun 26, 383-392.
Parracho, et al. (2005b). Differences between the gut microflora of children with autistic spectrum disorders and that of healthy children. Journal of medical microbiology 54, 987-991.
Penagarikano, et al. (2011). Absence of CNTNAP2 leads to epilepsy, neuronal migration abnormalities, and core autism-related deficits. Cell 147, 235-246.
Perry, et al. (2007). Sensorimotor gating deficits in adults with autism. Biological psychiatry 61, 482-486.
Persico, A.M., and Napolioni, V. (2013). Urinary p-cresol in autism spectrum disorder. Neurotoxicology and teratology 36, 82-90.
Portfors, C.V. (2007). Types and functions of ultrasonic vocalizations in laboratory rats and mice. J Am Assoc Lab Anim Sci 46, 28-34.
Price, et al. (2009). FastTree: Computing Large Minimum Evolution Trees with Profiles instead of a Distance Matrix. Mol Biol Evol 26, 1641-1650.
Pruesse, et al. (2012). SINA: Accurate high-throughput multiple sequence alignment of ribosomal RNA genes. Bioinformatics 28, 1823-1829.
Quast, et al. (2013). The SILVA ribosomal RNA gene database project: improved data processing and web-based tools. Nucleic Acids Res 41, D590-D596.
Rao, et al. (2009). A randomized, double-blind, placebo-controlled pilot study of a probiotic in emotional symptoms of chronic fatigue syndrome. Gut Pathog 1, 6.
Resta-Lenert, S.C., and Barrett, K.E. (2009). Modulation of intestinal barrier properties by probiotics: role in reversing colitis. Ann N Y Acad Sci 1165, 175-182.
Riehle, et al. (2012). The Genboree Microbiome Toolset and the analysis of 16S rRNA microbial sequences. Bmc Bioinformatics 13.
Rossignol, D.A., and Frye, R.E. (2012). Mitochondrial dysfunction in autism spectrum disorders: a systematic review and meta-analysis. Mol Psychiatry 17, 290-314.
Round, J.L., and Mazmanian, S.K. (2009). The gut microbiota shapes intestinal immune responses during health and disease. Nat Rev Immunol 9, 313-323.
Round, J.L., and Mazmanian, S.K. (2010). Inducible Foxp3+ regulatory T-cell development by a commensal bacterium of the intestinal microbiota. Proc Natl Acad Sci U S A 107, 12204-12209.
Saldanha, A.J. (2004). Java Treeview-extensible visualization of microarray data. Bioinformatics 20, 3246-3248.
Sandler, et al. (2000). Short-term benefit from oral vancomycin treatment of regressive-onset autism. J Child Neurol 15, 429-435.
Sankoorikal, et al. (2006). A mouse model system for genetic analysis of sociability: C57BL/6J versus BALB/cJ inbred mouse strains. Biological psychiatry 59, 415-423.

(56) References Cited

OTHER PUBLICATIONS

Scattoni, et al. (2011). Unusual repertoire of vocalizations in adult BTBR T+tf/J mice during three types of social encounters. Genes, brain, and behavior 10, 44-56.
Schmeisser, et al. (2012). Autistic-like behaviours and hyperactivity in mice lacking ProSAP1/Shank2. Nature 486, 256-260.
Schwartzer, et al. (2013). Maternal immune activation and strain specific interactions in the development of autism-like behaviors in mice. Translational psychiatry 3, e240.
Segata, et al. (2011). Metagenomic biomarker discovery and explanation. Genome biology 12, R60.
Sharma, et al. (2010). Molecular modulation of intestinal epithelial barrier: contribution of microbiota. Journal of biomedicine & biotechnology 2010, 305879.
Shi, et al. (2009). Activation of the maternal immune system alters cerebellar development in the offspring. Brain Behav Immun 23, 116-123.
Silverman, et al. (2010). Behavioural phenotyping assays for mouse models of autism. Nature Reviews Neuroscience 11, 490-502.
Smith, E.A., and Macfarlane, G.T. (1997). Formation of Phenolic and Indolic Compounds by Anaerobic Bacteria in the Human Large Intestine. Microb Ecol 33, 180-188.
Smith, et al. (2007). Maternal immune activation alters fetal brain development through interleukin-6. J Neurosci 27, 10695-10702.
Sommese, et al. (2012). Evidence of Bacteroides fragilis protection from Bartonella henselae-induced damage. PLoS One 7, e49653.
Song, et al. (2004). Real-time PCR quantitation of clostridia in feces of autistic children. Appl Environ Microbiol 70, 6459-6465.
Suzuki, et al. (2011). Interleukin-6 (IL-6) regulates claudin-2 expression and tight junction permeability in intestinal epithelium. J Biol Chem 286, 31263-31271.
Tabuchi, et al. (2007). A neuroligin-3 mutation implicated in autism increases inhibitory synaptic transmission in mice. Science 318, 71-76.
Tamura, et al. (2011). Loss of claudin-15, but not claudin-2, causes Na+ deficiency and glucose malabsorption in mouse small intestine. Gastroenterology 140, 913-923.
Thomas, et al. (2009). Marble burying reflects a repetitive and perseverative behavior more than novelty-induced anxiety. Psychopharmacology 204, 361-373.
Tillisch, et al. (2013). Consumption of fermented milk product with probiotic modulates brain activity. Gastroenterology 144, 1394-1401 e1394.
Tsai, et al. (2012). Autistic-like behaviour and cerebellar dysfunction in Purkinje cell Tsc1 mutant mice. Nature 488, 647-651.
Turner, J.R. (2009). Intestinal mucosal barrier function in health and disease. Nat Rev Immunol 9, 799-809.
Wang, et al. (2012). Elevated fecal short chain fatty acid and ammonia concentrations in children with autism spectrum disorder. Dig Dis Sci 57, 2096-2102.
Wang, et al. (2011). The prevalence of gastrointestinal problems in children across the United States with autism spectrum disorders from families with multiple affected members. Journal of developmental and behavioral pediatrics : JDBP 32, 351-360.
White, J.F. (2003). Intestinal pathophysiology in autism. Exp Biol Med (Maywood) 228, 639-649.
White, et al. (2009). Statistical Methods for Detecting Differentially Abundant Features in Clinical Metagenomic Samples. Plos Comput Biol 5.
Wikoff, et al. (2009). Metabolomics analysis reveals large effects of gut microflora on mammalian blood metabolites. Proc Natl Acad Sci U S A 106, 3698-3703.
Williams, et al. (2011). Impaired carbohydrate digestion and transport and mucosal dysbiosis in the intestines of children with autism and gastrointestinal disturbances. PLoS One 6, e24585.
Williams, et al. (2012). Application of novel PCR-based methods for detection, quantitation, and phylogenetic characterization of Sutterella species in intestinal biopsy samples from children with autism and gastrointestinal disturbances. MBio 3.
Wirtz, et al. (2007). Chemically induced mouse models of intestinal inflammation. Nature protocols 2, 541-546.
Wittebolle, et al. (2009). Initial community evenness favours functionality under selective stress. Nature 458, 623-626.
Won, et al. (2012). Autistic-like social behaviour in Shank2-mutant mice improved by restoring NMDA receptor function. Nature 486, 261-265.
Yang, et al. (2011). Automated three-chambered social approach task for mice. Curr Protoc Neurosci Chapter 8, Unit 8 26.
Yap, et al. (2010). Urinary metabolic phenotyping differentiates children with autism from their unaffected siblings and age-matched controls. Journal of proteome research 9, 2996-3004.
International Search Report and Written Opinion dated Feb. 27, 2012 for International Application PCT/US2011/055159, filed Oct. 6, 2011.
Kidd, Autism, an extreme challege to integrative medicine. Part 2: medical management. Altem. Med. Rev. vol. 7, No. 6, pp. 472-499 (2002).
Ganapathy et al., "Endogenous Elevation of Homocysteine Induces Retinal Neuron Death in the Cystathionine-Beta-Synthenase Mutant Mouse," Invest. Opthamol. Vis. Sci., 50(9):4460-4470 (2009).
Hammock et al., "2003 Progress Report: Environmental Factors in the Etiology of Autism: Analytic Biomarkers (xenobiotic) Core," Extramural Research, United States Environmental Protection Agency (2003), retrieved online from EPA. <http://cfpub.epa.gov/ncer_abstracts/index.cfm/fuseaction/display.abstractDetail/abstract/7872/report/2003>.
Hsiao et al., "Microbiota modulate behavioral and physiological abnormalities associated with neurodevelopmental disorders," Cell, vol. 155, No. 7, Dec. 1, 2013.
Rong et al., "Cystathionine Beta Synthase Participates in Murine Oocyte Maturation Mediated by Homocysteine," Reprod. Toxicol., 24(1):89-96 (2007).
Wang et al., "Is Urinary Indolyl-3-Acryloylglycine a Biomarker for Autism with Gastrointestinal Symptoms?," Biomarkers, 14(8):596-603 (2009).
International Search Report dated Feb. 28, 2014 for International Patent Application No. PCT/US2013/057148 filed Aug. 28, 2013.
Extended European Search Report dated Mar. 3, 2014 for European Patent Application No. 11831629.8 filed Oct. 6, 2011.
Office Action dated Nov. 10, 2014 for European Patent Application No. 11831629.8 filed Oct. 6, 2011.
Office Action dated Aug. 18, 2015 for Japanese Patent Application No. 2013-532955 filed Oct. 6, 2011.
Office Action dated Apr. 1, 2015 for European Patent Application No. 11831 629.8-1456 filed on Oct. 6, 2011.
Office Action dated Aug. 12, 2016 for U.S. Appl. No. 14/925,510, filed Oct. 28, 2015.
Robinson, et al. "From Structure to Function: the Ecology of Host-Associated Microbial Communities" Microbiology and Molecular Biology Reviews, Sep. 2010, pp. 456-476.
Critchfield, et al., 2011, "The potential role of probiotics in the management of childhood autism spectrum disorders." Gastroenterology Research and Practice, vol. 2011, Article ID 161358, pp. 1-8.
Petra, Louis, "Does the human gut mircrobiota contribute to the etiology of autism spectrum disorders?", Digestive diseases and sciences, vol. 57, No. 8, Jun. 27, 2012, pp. 1987-1989.
Hsiao, Elaine, "Gastrointestinal Issues in Autism spectrum disorder", Harvard Review of Psychiatry, Mar.-Apr. 2014, vol. 22(2), pp. 104-111.
Partial Supplementary European Search Report dated May 2, 2016 issued in EP 13832132.8.
Office Action dated Nov. 18, 2015 in U.S. Appl. No. 13/267,748.
Notice of Allowance dated Jun. 6, 2016 in U.S. Appl. No. 13/267,748.
Extended European Search Report dated Jun. 24, 2016, issued in EP16164727.6.
International Search Report and Written Opinion dated Jun. 30, 2016 issued in PCT/US2015/57891.
International Search Report and Written Opinion dated Jan. 20, 2016 issued in PCT/US2015/57897.
International Search Report and Written Opinion dated Jan. 12, 2016 issued in PCT/US2015/57888.

(56) References Cited

OTHER PUBLICATIONS

Bailey, K.R., and Crawley, J.N. (2009). Anxiety-Related Behaviors in Mice. In Methods of Behavior Analysis in Neuroscience, J.J. Buccafusco, ed. (Boca Raton (FL)).
Caporaso et al. (2010). QIIME allows analysis of high-throughput community sequencing data. Nat Methods 7, 335-336.
Hansen et al. The colitis-associated transcriptional profile of commensal Bacteroides thetaiotaomicron enhances adaptive immune responses to a bacterial antigen. PLoS One. 2012;7(8):e42645. doi: 10.1371/journal.pone.0042645. Epub Aug. 3, 2012.
Patterson, Maternal Infection and Immune Involvement in Autism, Trends Mol Med 17, 389 (Jul. 2011).
Patterson, P. H. 2011. Modeling features of autism in animals. Pediatric Res 69:34R-40R.
Office Action dated Feb. 7, 2017 for Japanese Patent Application No. 2016-088694 filed Apr. 27, 2016.
Extended European Search Report dated Aug. 25, 2016, issued in EP13832132.8.
Chi, "Clinical, animal studies probe DISC1's role in autism" Spectrum, Mar. 1, 2010, https://spectrumnews.org/news/clinical-animal-studies-probe-disc1s-role-in-autism/.
Kilpinen, et al., Association of DISC1 with autism and Asperger syndrome Molecular Psychiatry (2008) 13, 187-196.
Penagariko et al., "What does CNTNAP2 reveal about autism spectrum disorder?" Trends in Molecular Medicine, 2012, vol. 18, pp. 156-163.
Office Action dated Oct. 7, 2016 in U.S. Appl. No. 14/925,240, filed Oct. 28, 2015.
Office Action dated Oct. 5, 2016 in U.S. Appl. No. 14/839,041, filed Aug. 28, 2015.
Yadav, et al., "Pharmacological inhibition of gut-derived serotonin synthesis is a potential bone anabolic treatment for osteoporosis", Nature Medicine 16(3):308-312, 2010.
Nemeroff et al., "Are platelets the link between depression and ischemic heart disease?", American Heat Journal 140(4): S57-S62, 2000.
American Psychiatric Association: Diagnostic and Statistical Manual of Mental Disorders, Fourth Edition, Text Revision. Washington, DC, pp. 69-84, American Psychiatric Association, 2000.
Seltzer, et al., "The Symptoms of Autism Spectrum Disorders in Adolescence and Adulthood" Journal of Autism and Developmental Disorders, vol. 33, No. 6, pp. 565-581, Dec. 2003.
Maslowski, et al., "Diet, gut microbiota and immune responses" Nature Immunology vol. 12 No. 1, pp. 5-9, Jan. 2011.
Office Action dated Jul. 20, 2017 in Canadian Application No. 2,813,606, filed Oct. 6, 2011.
Gupta, "The phylogeny of proteobacteria: relationships to other eubacterial phyla and eukaryotes.", FEMS Microbiology Reviews 24 (4):367-402, 2000.
Jandhyala et al., "Role of the normal gut microbiota", World Journal of Gastroenterology 21(9): 8787-8803, 2015.
Lopetuso et al., "Commensal Clostridia: leading players in the maintenance of gut homeostasis", Gut Pathogents 5(1): 23, 2013.
Winek et al., "The Gut Microbiome as Therapeutic Target I Central Nervous System Diseases: Implications for Stroke", Neurotherapeutics 13(4): 762-774, 2016.
International Preliminary Report on Patentability dated May 2, 2017 issued in PCT/US2015/057897.
International Preliminary Report on Patentability dated May 2, 2017 issued in PCT/US2015/057888.
International Preliminary Report on Patentability dated May 2, 2017 issued in PCT/US2015/057891.
Office Action dated Aug. 22, 2017 in U.S. Appl. No. 14/925,510.
Office Action dated Jan. 25, 2017 in U.S. Appl. No. 14/925,510.
Office Action dated Jun. 13, 2017 in Japanese Application No. 2015-530008.
Office Action dated May 25, 2017 in U.S. Appl. No. 14/839,041.
Office Action dated May 5, 2017 issued in U.S. Appl. No. 14/925,240.
Ono et al., "Antioxidant compounds have potent anti-fibrillogenic and fibril0destabilizing effects for α-synuclein fibrils in vitro", Journal of Neurochemistry, 2006, 97, 105-115.
Office Action dated Nov. 30, 2017 in U.S. Appl. No. 14/925,242.
Office Action dated Jan. 11, 2018 in European Application No. 13832132.8, filed Feb. 17, 2015.
Final Office Action dated Jan. 24, 2018 in U.S. Appl. No. 14/925,240.
Final Office Action dated Jan. 26, 2018 in U.S. Appl. No. 14/925,510.
International Search Report dated Jan. 30, 2018 issued in PCT/US17/63108 filed Nov. 22, 2017.
Office Action dated Apr. 24, 2018 in U.S. Appl. No. 15/249,870.
Beaugerie et al., 2004. Antibiotic-associated diarrhoea. Best Practice & Research Clinical Gastroenterology, vol. 18, Issue 2, pp. 337-352.
Borghi et al., Rett Syndrome: A Focus on Gut Microbiota, International Journal of Molecular Sciences, vol. 18, No. 2, pp. 1-17, Feb. 7, 2017.
De Theije, C., "Neuroimmunomodulation of the young brain: Nutrition, a Gut Feeling", The Netherlands: Utrecht University, pp. 1-78, 2014.
Extended European Search Report dated Apr. 18, 2018 in Application No. 15855495.6.
Extended European Search Report dated May 2, 2018 in Application No. 15855218.2.
Extended European Search Report dated May 14, 2018 in Application No. 15856096.1.
Gibson RG., 2004. Fibre and effects on probiotics (the prebiotic concept). Clinical Nutrition Supplements, vol. 1, Issue 2, pp. 25-31.
Guarner et al., 2003. Gut flora in health and disease. The Lancet, vol. 361, Issue 9356, Feb. 8, 2003, pp. 512-519. PMID 12583961. Accessed Sep. 15, 2007.
International Search Report and Written Opinion dated May 14, 2018 in Application No. PCT/US2018/017116.
International Search Report and Written Opinion dated Jul. 19, 2018 in Application No. PCT/US2018/018069.
Macfarlane et al., Chemotaxonomic Analysis of Bacterial Populations Colonizing the Rectal Mucosa in Patients with Ulcerative Colitis. Clinical Infectious Diseases. 2004. vol. 38, pp. 1690-1699.
McTighe et al. (2013), The BTBR mouse model of autism spectrum disorders has learning and attentional impairments and alterations in acetylcholine nad kynurenic acid in prefrontal cortext. PLoS ONE 8: e62189, 11 pages.
Meyza et al. (2013), The BRBR T+tf/J mouse model for autism spectrum disorders—in search of biomarkers. Behavioural Brain Research 251: 25-34.
Office Action dated Aug. 10, 2018 in U.S. Appl. No. 14/925,240.
Office Action dated Jun. 12, 2018 in Australian Application No. 2013308826.
Office Action dated Jul. 4, 2018 in Canadian Application No. 2,881,656.
Office Action dated Jun. 22, 2018 in Chinese Application No. 201380056909.2 with English Translation.
Office Action dated May 8, 2018 in Japanese Application No. 2015-530008 with English Translation.
Office Action dated Aug. 22, 2018 in Eurasian Patent Application No. 201790811 with English Translation.
Sears, C., A dynamic partnership: Celebrating our gut flora. Anaerobe, vol. 11, Issue 5, Oct. 2005, pp. 247-251.
Sender et al., Revised Estimates for the Number of Human and Bacteria Cells in the Body. PLOS Biology. Aug. 19, 2016. 14(8) e1002533, in 10 pages.
Steinhoff, U., Who controls the crowd? New findings and old questions about the intestinal microflora. Immunology Letters. vol. 99, Issue 1, Jun. 15, 2005, pp. 12-16.
Stephen et al., The Microbial Contribution to Human Faecal Mass. Journal of Medical Microbiology. 1980. 13: pp. 45-56.
Strati et al., "Altered gut microbiota in Rett syndrome", Microbiome, vol. 4, No. 41, pp. 1-15, Jul. 30, 2016.
Yasui et al., "115q11.2-13.3 chromatin analysis reveals epigenetic regulation of CHRNA7 with deficiencies in Rett and autism brain", Human Molecular Genetics, vol. 20, No. 22, pp. 4311-4323, Aug. 12, 2011.

(56) References Cited

OTHER PUBLICATIONS

RIA Science, 'Scientists' Bacteria in the human body are not 10 times larger than their cells.' [online], ;MIA "Russia Today", Jan. 11, 2016 [retrieved on Aug. 29, 2018], 14 pages. Retrieved from the Internet: <URL: https://ria.ru/science/20160111/1357907466.html>.

Todar, K., 'The Normal Bacterial Flora of Humans.' Todar's Online Textbook of Bacteriology [online]. 2012 [retrieved Aug. 28, 2018], 8 pages. Retrieved from the Internet: <URL: http://www.textbookofbacteriology.normalflora.html>.

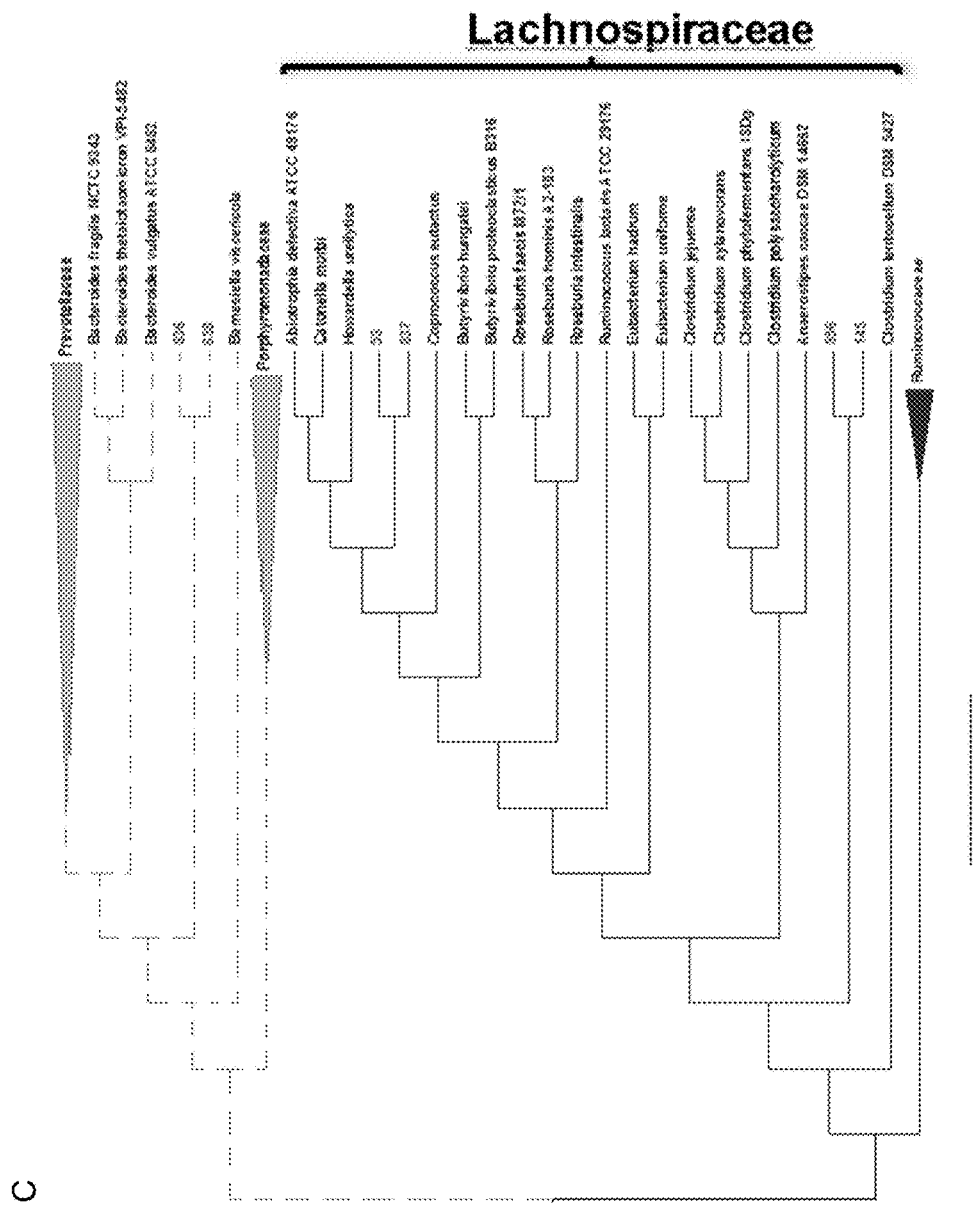
Figure 8 (continued) C

Figure 12A

| Fold change versus saline | Super Pathway | Metabolite | P | P+BF |
|---|---|---|---|---|
| < 0.5 | | | | |
| 0.5-0.6 | | | | |
| 0.6-0.7 | | | | |
| 1.0-2.0 | | | | |
| > 5.0 | | | | |

| Super Pathway | Metabolite | P | P+BF |
|---|---|---|---|
| Amino acid | sarcosine (N-Methylglycine) | | |
| | aspartate | | |
| | 3-ureidopropionate | | |
| | glutarate (pentanedioate) | | |
| | tyrosine | | |
| | 3-(4-hydroxyphenyl)lactate | | |
| | 3-phenylpropionate (hydrocinnamate) | | |
| | serotonin (5HT) | | |
| | 3-methyl-2-oxovalerate | | |
| | 3-methyl-2-oxobutyrate | | |
| | 4-methyl-2-oxopentanoate | | |
| | isobutyrylcarnitine | | |
| | 2-methylbutyroylcarnitine | | |
| | isovalerylcarnitine | | |
| | 2-hydroxybutyrate (AHB) | | |
| | arginine | | |
| | ornithine | | |
| | 2-aminobutyrate | | |
| | 4-guanidinobutanoate | | |
| | 5-oxoproline | | |
| Peptide | glycylvaline | | |
| | gamma-glutamyltryptophan | | |
| | TDTEDKGEFLSEGGGV | | |
| | TDTEDKGEFLSEGGGVR | | |
| Carbohydrate | sorbitol | | |
| | pyruvate | | |
| | ribose | | |
| | ribulose | | |
| | ribitol | | |
| | xylitol | | |
| Energy | citrate | | |
| | fumarate | | |
| | malate | | |
| Nucleotide (Purine metabolism) | hypoxanthine | | |
| | inosine | | |
| | adenosine | | |
| | adenosine 5'-monophosphate (AMP) | | |
| | guanosine 5'-monophosphate (5'-GMP) | | |
| | urate | | |
| | 2'-deoxycytidine | | |
| | uracil | | |
| | pseudouridine | | |
| Cofactors | nicotinamide | | |
| Xenobiotics | catechol sulfate | | |
| | salicylate | | |
| | equol sulfate | | |
| | erythritol | | |
| Lipid | choline | | |
| | chiro-inositol | | |
| | pinitol | | |

DIAGNOSIS AND TREATMENT OF AUTISM SPECTRUM DISORDER

RELATED APPLICATIONS

The present application claims priority under 35 U.S.C. § 119(e) to U.S. Provisional Application No. 61/694,679, filed on Aug. 29, 2012, which is herein expressly incorporated by reference in its entirety.

STATEMENT REGARDING FEDERALLY SPONSORED R&D

This invention was made with government support under grant no. W81XWH-11-0515 awarded by the Army, Graduate Training grant No. 5 T32 GM07737 awarded by National Institutes of Health, Graduate Research Fellowship No. DGE-0703267 awarded by National Science Foundation, and grant No. MH100556 awarded by National Institutes of Mental Health. The government has certain rights in the invention.

REFERENCE TO SEQUENCE LISTING

The present application is being filed along with a Sequence Listing in electronic format. The Sequence Listing is provided as a file entitled SEQLISTING.TXT, created Aug. 28, 2013, which is 4 Kb in size. The information in the electronic format of the Sequence Listing is incorporated herein by reference in its entirety.

BACKGROUND

Field of the Invention

The present application relates generally to the field of diagnosing and treatment of autism spectrum disorders (ASD).

Description of the Related Art

Autism spectrum disorder (ASD) is a serious neurodevelopmental disorder characterized by stereotypic behaviors and deficits in language and social interaction. The reported incidence of autism has rapidly increased to 1 in 88 births in the United States as of 2008 (CDC, 2012), representing a significant medical and social burden in the coming decades. Reproducible molecular diagnostics for ASD have not been developed and therapies for treating the core symptoms of ASD are limited, and reproducible molecular diagnostics have not been developed. Much research into autism spectrum disorder (ASD) has focused on genetic, behavioral and neurological aspects of disease, but primary roles for environmental risk factors (Hallmayer et al., 2011), immune dysregulation and additional peripheral disruptions in the pathogenesis of ASD have recently gained significant attention. The striking heterogeneity among individuals that share the same diagnosis is consistent with the prevailing notion that there are a variety of etiologies for ASD. Moreover, the spectrum of ASD symptoms and challenges in identifying specific causes, treatments and molecular biomarkers underscore the need to better define the clinical subtypes of ASD and provide tailored treatment to subclasses of ASD individuals.

SUMMARY

Some embodiments disclosed herein are related to a method for improving behavioral performance in a subject, where the method includes: determining the blood level of an autism spectrum disorder (ASD)-related metabolite in a subject in need of treatment; and adjusting the blood level of the ASD-related metabolite in the subject until an improvement in the behavioral performance in the subject is observed.

In some embodiments, the subject suffers from anxiety, autism spectrum disorder (ASD), or a pathological condition with one or more of the symptoms of ASD. In some embodiments, the subject suffers from ASD.

In some embodiments, adjusting the blood level of the ASD-related metabolite comprises adjusting the composition of gut microbiota in the subject. In some embodiments, adjusting the composition of gut microbiota of the subject comprises fecal transplantation. In some embodiments, adjusting the composition of gut microbiota of the subject comprises administering the subject a composition comprising *Bacteroides* bacteria. In some embodiments, the *Bacteroides* bacteria is *B. fragilis, B. thetaiotaomicron, B. vulgatus*, or a mixture thereof.

In some embodiments, the composition is a probiotic composition, a neutraceutical, a pharmaceutical composition, or a mixture thereof.

In some embodiments, adjusting the composition of gut microbiota of the subject comprises reducing the level of Clostridia bacteria in the subject. In some embodiments, the Clostridia bacteria is Lachnospiraceae. In some embodiments, adjusting the composition of gut microbiota of the subject comprises increasing the level of Ruminococcaceae, Erysipelotrichaceae, and/or Alcaligenaceae bacteria in the subject.

In some embodiments, the ASD-related metabolite is one of the metabolites listed in Table 1. In some embodiments, the ASD-related metabolite is a metabolite involved in tryptophan metabolism, a metabolite involved in fatty acid metabolism, a metabolite involved in purine metabolism, glycolate, imidazole propionate, or N-acetylserine. In some embodiments, the metabolite involved in tryptophan metabolism is 4-ethylphenylsulfate, indolepyruvate, indolyl-3-acryloylglycine, or serotonin. In some embodiments, the ASD-related metabolite is 4-ethylphenylsulfate, indolepyruvate, glycolate, or imidazole proprinate.

In some embodiments, adjusting the blood level of the ASD-related metabolite in the subject comprises administering to the subject an antibody against the ASD-related metabolite, an antibody against an intermediate for the in vivo synthesis of the ASD-related metabolite, or an antibody against a substrate for the in vivo synthesis of the ASD-related metabolite.

In some embodiments, the ASD-related metabolite is 4-ethylphenylsulfate or indolepyruvate.

In some embodiments, adjusting the blood level of the ASD-related metabolite in the subject comprises inhibiting an enzyme involved in the in vivo synthesis of the ASD-related metabolite.

In some embodiments, adjusting the blood level of the ASD-related metabolite ameliorates gastrointestinal (GI) distress of the subject. In some embodiments, the GI distress comprises abdominal cramps, chronic diarrhea, constipation, intestinal permeability, or a combination thereof. In some embodiments, adjusting the blood level of the ASD-related metabolite reduces intestinal permeability of the subject.

In some embodiments, the method includes determining the reference level of the metabolite in non-autistic subjects. In some embodiments, the method includes determining the behavioral performance of the subject prior to and after adjusting the blood level of the ASD-related metabolite in the subject.

In some embodiments, determining the behavioral performance of the subject comprises using Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS).

Also disclosed herein in some embodiments is a method for improving behavioral performance in a subject, where the method includes: determining the urine level of an autism spectrum disorder (ASD)-related metabolite in a subject in need of treatment; and adjusting the urine level of the ASD-related metabolite in the subject until an improvement in behavioral performance in the subject is observed. In some embodiments, the ASD-related metabolite is 4-methylphenyl, 4-methylphenylsulfate or indolyl-3-acryloylglycine.

In some embodiments, adjusting the urine level of the ASD-related metabolite comprises adjusting the composition of gut microbiota in the subject. In some embodiments, adjusting the composition of gut microbiota of the subject comprises administering the subject a composition comprising *Bacteroides* bacteria.

Some embodiments provided here are related to a method for assessing the susceptibility of a subject suffering from autism spectrum disorder (ASD) to probiotic treatment, where the method includes: determining the blood level of a *B. fragilis*-responsive metabolite in the subject; and comparing the blood level of the *B. fragilis*-responsive metabolite in the subject to a reference level of the metabolite in subjects suffering from ASD and one or more gastrointestinal disorders, wherein substantial identity between the blood level of the metabolites in the subject and the reference level indicates that the subject is susceptible to the probiotic treatment.

In some embodiments, the method includes adjusting the composition of gut microbiota of the subject.

In some embodiments, adjusting the composition of gut microbiota of the subject comprises administering the subject a composition comprising *Bacteroides* bacteria. In some embodiments, the *Bacteroides* bacteria is *B. fragilis, B. thetaiotaomicron, B. vulgatus*, or a mixture thereof.

In some embodiments, adjusting the composition of gut microbiota of the subject comprises fecal transplantation.

In some embodiments, the *B. fragilis*-responsive metabolite is one of the metabolites listed in Table 2.

Some embodiments disclosed herein are related to a method for relieving gastrointestinal (GI) distress of a subject suffering from autism spectrum disorder (ASD), comprising reducing intestinal permeability in the subject. In some embodiments, the GI distress comprises abdominal cramps, chronic diarrhea, constipation, intestinal permeability, or a combination thereof. In some embodiments, reducing intestinal permeability comprises adjusting the composition of gut microbiota in the subject.

Also disclosed herein in some embodiments is a method for diagnosing autism spectrum disorder (ASD) in a subject, where the method includes: determining the level of a cytokine in gut and the blood level of one or more ASD-related metabolites in the subject; and detecting whether or not there is an alteration in the level of the cytokine in gut and the blood level of at least one or more of the ASD-related metabolites in the subject as compared to a reference level of the cytokine and the metabolite in non-autistic subjects, whereby an alteration in the amount of the cytokine in gut and the blood level of at least one of the one or more metabolites indicates that the subject suffers from ASD.

Further disclosed herein in some embodiments is a method for diagnosing autism spectrum disorder (ASD) in a subject, where the method includes: determining the blood level of two or more ASD-related metabolites in the subject; and detecting whether or not there is an alteration in the blood level of the two or more ASD-related metabolites in the subject as compared to a reference level of the metabolites in non-autistic subjects, whereby an alteration in the blood level of at least two of the two or more ASD-related metabolites indicates that the subject suffers from ASD.

In some embodiments, the one or more of the ASD-related metabolites are selected from the metabolites listed in Table 1. In some embodiments, the one or more ASD-related metabolites comprises a metabolite involved in tryptophan metabolism, a metabolite involved in fatty acid metabolism, a metabolite involved in purine metabolism, glycolate, imidazole propionate, N-acetylserine, or any combination thereof. In some embodiments, the metabolite involved in tryptophan metabolism is 4-ethylphenylsulfate, indolepyruvate, indolyl-3-acryloylglycine, or serotonin. In some embodiments, the cytokine is interleukin-6 (IL-6). In some embodiments, the method includes altering the level of one or more ASD-related metabolites in the subject to improve behavioral performance in the subject if it is indicated that the subject suffers from ASD.

BRIEF DESCRIPTION OF THE DRAWINGS

FIG. 1A. Intestinal permeability assay, measuring fluorescence intensity of fluorescein isothiocyanate (FITC) detected in serum after oral gavage of FITC-dextran. DSS: n=6, S: adult n=16; adolescent n=4, P: adult n=17; adolescent n=4. Data are normalized to fluorescence intensity observed in adult saline offspring. FIG. 1B. Expression of tight junction components relative to beta-actin in colons of adult saline and poly(I:C) offspring. Data for each gene are normalized to expression levels in saline offspring. n=8. FIG. 1C. Expression of cytokines and inflammatory markers relative to beta-actin in colons of adult saline and poly(I:C) offspring. Data for each gene are normalized to expression levels in saline offspring. n=6-21. FIG. 1D. Protein levels of cytokines and chemokines relative to total protein content in colons of adult saline and poly(I:C) offspring. n=10. Data are presented as mean±SEM. *$p<0.05$, $p<0.01$, *$p<0.001$. DSS=dextran sodium sulfate, S=saline+vehicle, P=poly(I:C)+vehicle. For each experiment, adult saline and poly(I:C) offspring were treated with vehicle at 3 weeks of age, and data were collected simultaneously for poly(I:C)+*B. fragilis* treatment group.

FIG. 2A. Expression of tight junction components relative to beta-actin in small intestines of adult saline and poly(I:C) offspring. Data for each gene are normalized to expression levels in saline offspring. n=8. FIG. 2B. Quantification of the effect of *B. fragilis* treatment on expression of notable tight junction components relative to beta-actin in small intestines of MIA offspring. Data for saline and poly(I:C) are as in panel (A). n=8. FIG. 2C. Protein levels of cytokines and chemokines relative to total protein content in small intestines of adult saline, poly(I:C) and poly(I:C)+*B. fragilis* offspring. Data is normalized to expression levels in saline offspring. Asterisks directly above bars indicate significance compared to saline control (normalized to 1, as denoted by the black line), whereas asterisks at the top of the graph denote statistical significance between poly(I:C) and poly(I:C)+*B. fragilis* groups. n=8-10. Data are presented as mean±SEM. *p<0.05, **p<0.01, S=saline+vehicle, P=poly (I:C)+vehicle, P+BF=poly(I:C)+*B. fragilis*

FIG. 3A. Percent frequency of Foxp3+ CD25+ T regulatory cells from a parent population of CD4+ TCRb+ cells, measured by flow cytometry of splenocytes from adult saline, poly(I:C) and poly(I:C)+*B. fragilis* offspring. n=5. FIG. 3B. Percent frequency of CD4+ T helper cells and CD11b+ and Gr-1+ neutrophilic and monocytic cells from a parent population of TER119− cells, measured by flow cytometry of splenocytes from adult saline, poly(I:C) and poly(I:C)+*B. fragilis* offspring. n=5. FIG. 3C. Production of IL-17 and IL-6 by splenic CD4+ T cells isolated from adult saline and poly(I:C) offspring, after in vitro stimulation with PMA/ionomycin. Treatment effects were assessed by repeated measures two-way ANOVA with Bonferroni post-hoc test. n=5. FIG. 3D. Production of IL-17 and IL-6 by CD4+ T cells isolated from mesenteric lymph nodes of adult saline and poly(I:C) offspring, after in vitro stimulation with PMA/ionomycin. Treatment effects were assessed by repeated measures two-way ANOVA with Bonferroni post-hoc test. n=5. FIG. 3E. Anxiety-like and locomotor behavior in the open field exploration assay for adult MIA offspring treated with mutant *B. fragilis* lacking production of polysaccharide A (PSA). Data indicate total distance traveled in the 50×50 cm open field (right), duration spent in the 17×17 cm center square (middle) and number of entries into the center square (left) over a 10-minute trial. Data for saline, poly(I:C) and poly(I:C)+*B. fragilis* groups are as in FIG. 10. poly(I:C)+*B. fragilis* with PSA deletion: n=17. FIG. 3F. Repetitive burying of marbles in a 6×8 array in a 10-minute trial. Data for saline, poly(I:C) and poly(I:C)+*B. fragilis* groups are as in FIG. 10. poly(I:C)+*B. fragilis* with PSA deletion: n=17. Data are presented as mean±SEM. *p<0.05, p<0.01, *p<0.001. S=saline+vehicle, P=poly(I:C)+vehicle, P+BF=poly(I:C)+*B. fragilis*, P+BFΔPSA=poly(I:C)+*B. fragilis* with PSA deletion.

FIG. 4A. Richness of the gut microbiota, as illustrated by rarefaction curves plotting Faith's Phylogenetic Diversity (PD) versus the number of sequences for each treatment group. FIG. 4B. Evenness of the gut microbiota, as indicated by the Gini coefficient. FIG. 4C. Levels of *B. fragilis* 16S sequence (top) and bacterial 16S sequence (bottom) in fecal samples collected at 1, 2, and 3 weeks post treatment of adult offspring with vehicle or *B. fragilis*. Germ-free mice colonized with *B. fragilis* were used as a positive control. Data are presented as quantitative RT-PCR cycling thresholds [C(t)], where C(t)>34 (hatched line) is considered negligible, and for C(t)<34, lesser C(t) equates to stronger abundance. n=1, where each represents pooled sample from 3-5 independent cages. FIG. 4D. Levels of *B. fragilis* 16S sequence (top) and bacterial 16S sequence (bottom) in fecal samples collected at 1, 2, and 3 weeks post treatment of adult offspring with vehicle or *B. fragilis*. Germ-free mice colonized with *B. fragilis* were used as a positive control. Data are presented as quantitative RT-PCR cycling thresholds [C(t)], where C(t)>34 (hatched line) is considered negligible, and for C(t)<34, lesser C(t) equates to stronger abundance. n=1, where each represents pooled sample from 3-5 independent cages. Data are presented as mean±SEM. S=saline+vehicle, P=poly(I:C)+vehicle, P+BF=poly(I:C)+*B. fragilis*, GF+BF=germ-free+*B. fragilis*.

FIG. 5A is an unweighted UniFrac-based 3D PCoA plot based on all OTUs, illustrating global differences in the gut microbiota between adult MIA and control offspring. The percent variation explained by each principal coordinate (PC) is indicated on the axes. FIG. 5B is an unweighted UniFrac-based 3D PCoA plot based on subsampling of Clostridia and Bacteroidia OTUs (2003 reads per sample). FIG. 5C is an unweighted UniFrac-based 3D PCoA plot based on subsampling of OTUs remaining after subtraction of Clostridia and Bacteroidia OTUs (47 reads per sample). FIG. 5D is a heat-map showing the relative abundance of unique OTUs of the gut microbiota (bottom, x-axis) for individual biological replicates from adult saline and poly(I:C) offspring (right, y-axis), where red of increasing intensity denotes increasing relative abundance of a unique OTU for a particular sample. All OTUs that significantly discriminate between treatment groups are plotted. Family-level taxonomic assignments as designated by the Ribosomal Database Project are indicated for each OTU. FIG. 5E shows mean relative abundance of OTUs classified by taxonomic assignments at the class level for the most abundant taxa (left) and least abundant taxa (right). n=10. Data were simultaneously collected and analyzed for poly(I:C)+*B. fragilis* treatment group.

FIG. 6A. Intestinal permeability assay, measuring fluorescence intensity of fluorescein isothiocyanate (FITC) detected in serum after oral gavage of FITC-dextran. Data are normalized to fluorescence intensity observed in adult saline offspring. Data for DSS, saline and poly(I:C) are as in FIG. 1. poly(I:C)+*B. fragilis*: n=9. FIG. 6B. Expression of tight junction components relative to beta-actin in colons of adult saline, poly(I:C) and poly(I:C)+*B. fragilis* offspring. Data for each gene are normalized to expression levels in saline offspring. Data for saline and poly(I:C) are as in FIG. 1. Asterisks directly above bars indicate significance compared to saline control (normalized to 1, as denoted by the black line), whereas asterisks at the top of the graph denote statistical significance between poly(I:C) and poly(I:C)+*B. fragilis* groups. n=8. FIG. 6C. Immunofluorescence staining for claudin 8. Representative images for n=5. FIG. 6D. Protein levels of claudin 8 (left) and claudin 15 (right) in colons from saline, poly(I:C) and poly(I:C)+*B. fragilis* offspring, as measured by Western blot. Representative signals from the same blot are depicted below. Data are normalized to signal intensity detected in saline offspring. n=3. FIG. 6E. Expression of IL-6 relative to beta-actin in colons of adult saline, poly(I:C) and poly(I:C)+*B. fragilis* offspring. Data is normalized to expression levels in saline offspring. Data for saline and poly(I:C) are as in FIG. 1. poly(I:C)+*B. fragilis*: n=3. FIG. 6F. Protein levels of cytokines and chemokines relative to total protein content in colons of adult saline, poly(I:C) and poly(I:C)+*B. fragilis* offspring. Data is normalized to expression levels in saline offspring. Data for saline and poly(I:C) are as in FIG. 1. Asterisks directly above bars indicate significance compared to saline control (normalized to 1, as denoted by the black line), whereas asterisks at the top of the graph denote statistical significance between poly(I:C) and poly(I:C)+*B. fragilis* groups. n=10. Data are presented as mean±SEM. *p<0.05, p<0.01, *p<0.001, n.s.=not significant. DSS=dextran sodium sulfate, S=saline+vehicle, P=poly(I:C)+vehicle, P+BF=poly(I:C)+*B. fragilis*.

FIG. 7A. Dose-dependent expression of claudin 8 (left) and claudin 15 (right) relative to beta-actin in colons of adult wild-type mice cultured for 4 hours ex vivo with increasing concentrations of recombinant mouse IL-6. Data are normalized to expression levels detected in 0 ng/ml IL-6 controls. n=3. FIG. 7B. Time-dependent expression of claudin 8 (left) and claudin 15 (right) relative to beta-actin in colons of adult wild-type mice cultured with 80 ng/ml recombinant mouse IL-6. n=3. FIG. 7C. Expression of claudin 8 (top) and claudin 15 (bottom) relative to beta-actin in colons of adult wild-type mice at 12 hours post treatment with recombinant mouse IL-6. n=3. Data are presented as mean±SEM.

FIG. 8A is an unweighted UniFrac-based 3D PCoA plot based on all OTUs. The percent variation explained by each principal coordinate (PC) is indicated on the axes. Data for saline and poly(I:C) are as in FIG. 2. FIG. 8B. Relative abundance of key OTUs of the family Lachnospiraceae (top) and order Bacteroidales (bottom) that are significantly altered by MIA and completely restored by B. fragilis treatment. Data are presented as mean±SEM. FIG. 8C is a phylogenetic tree based on nearest-neighbor analysis of 16S rRNA gene sequences for key OTUs presented in panel B. Clades shown in solid lines indicate OTUs of the family Lachnospiraceae and clades showing in broken lines indicate OTUs of the order Bacteroidales. The 6 taxa labeled with numbers indicate OTUs that are significantly elevated in poly(I:C) offspring and corrected by B. fragilis treatment. n=10.

FIG. 9A. Levels of B. fragilis 16S sequence (top) and bacterial 16S sequence (bottom) in fecal samples collected at 1, 2, and 3 weeks post treatment of adult offspring with vehicle or B. fragilis. Germ-free mice colonized with B. fragilis were used as a positive control. Data are presented as quantitative RT-PCR cycling thresholds [C(t)], where C(t)>34 (hatched line) is considered negligible, and for C(t)<34, lesser C(t) equates to stronger abundance. n=1, where each represents pooled sample from 3-5 independent cages. FIG. 9B. Levels of B. fragilis 16S sequence (top) and bacterial 16S sequence (bottom) in fecal samples collected at 1, 2, and 3 weeks post treatment of adult offspring with vehicle or B. fragilis. Germ-free mice colonized with B. fragilis were used as a positive control. Data are presented as quantitative RT-PCR cycling thresholds [C(t)], where C(t)>34 (hatched line) is considered negligible, and for C(t)<34, lesser C(t) equates to stronger abundance. n=1, where each represents pooled sample from 3-5 independent cages. Data are presented as mean±SEM. S=saline+vehicle, P=poly(I:C)+vehicle, P+BF=poly(I:C)+B. fragilis, GF+BF=germ-free+B. fragilis.

FIG. 10A. Anxiety-like and locomotor behavior in the open field exploration assay, as measured by total distance traveled in the 50×50 cm open field (right), duration spent in the 17×17 cm center square (middle), and number of entries into the center of the field (left) over a 10 minute trial. n=35-75. FIG. 10B. Sensorimotor gating in the pre-pulse inhibition assay, as measured by percent difference between the startle response to pulse only and startle response to pulse preceded by a 5 db or 15 db pre-pulse. Treatment effects were assessed by repeated measures two-way ANOVA with Bonferroni post-hoc test. n=35-75. FIG. 10C. Repetitive burying of marbles in a 3×6 array during a 10 minute trial. n=16-45. FIG. 10D. Communicative behavior, as measured by total number (left), average duration (middle) and total duration (right) of ultrasonic vocalizations produced by adult male mice during a 10 minute social encounter. n=10. FIG. 10E shows deficits in sociability in B. fragilis-treated MIA offspring. FIG. 10F shows deficits in social preference in B. fragilis-treated MIA offspring. Graphs represent cumulative results obtained for 3-6 independent cohorts of mice. Data are presented as mean±SEM. *p<0.05, p<0.01, *p<0.001. S=saline+vehicle, P=poly(I:C)+vehicle, P+BF=poly(I:C)+B. fragilis. Data were collected simultaneously for poly(I:C)+B. fragilis ΔPSA and poly(I:C)+B. thetaiotaomicron treatment groups.

FIG. 11A. Anxiety-like and locomotor behavior in the open field exploration assay, as measured by total distance traveled in the 50×50 cm open field (right), duration spent in the 17×17 cm center square (middle), and number of entries into the center of the field (left) over a 10 minute trial. Poly(I:C)+B. thetaiotaomicron: n=32. FIG. 11B. Repetitive burying of marbles in a 3×6 array during a 10 minute trial. Poly(I:C)+B. thetaiotaomicron: n=32. FIG. 11C. Communicative behavior, as measured by total number (left), average duration (middle) and total duration (right) of ultrasonic vocalizations produced by adult male mice during a 10 minute social encounter. Poly(I:C)+B. thetaiotaomicron: n=10. FIG. 11D. Sensorimotor gating in the pre-pulse inhibition assay, as measured by percent difference between the startle response to pulse only and startle response to pulse preceded by a 5 db or 15 db pre-pulse. Treatment effects were assessed by repeated measures two-way ANOVA with Bonferroni post-hoc test. Poly(I:C)+B. thetaiotaomicron: n=32. For all panels, data for saline, poly(I:C) and poly(I:C)+B. fragilis are as in FIG. 10. Graphs represent cumulative results obtained for 3-6 independent cohorts of mice. Data are presented as mean±SEM. *p<0.05, p<0.01, *p<0.001. S=saline+vehicle, P=poly(I:C)+vehicle, P+BF=poly(I:C)+B. fragilis, P+BT=Poly(I:C)+B. thetaiotaomicron.

FIGS. 12A-B. B. fragilis treatment causes statistically significant alterations serum metabolites, with widespread changes in biochemicals relevant to fatty acid metabolism and purine salvage pathways. Levels of 103 metabolites that are significantly altered in sera of B. fragilis-treated MIA offspring compared to saline controls, as measured by GC/LC-MS. Colors indicate fold change relative to metabolite concentrations detected in saline offspring, where red hues represent increased levels compared to controls and green hues represent decreased levels compared to controls (see legend on top left). All changes indicated are p<0.05 by two-way ANOVA with contrasts. P=poly(I:C), P+BF=poly(I:C)+B. fragilis. n=8.

FIG. 13A shows relative quantification of metabolites detected by GC/LC-MS that were significantly altered by MIA and restored by B. fragilis treatment. n=8. FIG. 13B shows concentrations of 4EPS detected by LC-MS in sera of adult germ-free (GF) versus conventionally-colonized (specific pathogen-free, SPF) mice. U.D.=undetectable. n=1, where each represents pooled sera from 3-5 mice. FIG. 13C. Anxiety-like and locomotor behavior in the open field exploration assay for conventional wild-type mice treated with 4EPS or saline vehicle. Data indicate total distance traveled in the 50×50 cm open field (right) and duration spent in the 17×17 cm center square (left) over a 10 minute trial. There is no difference between 4EPS- and vehicle-treated mice in number of entries into the center of the field (data not shown). n=10. FIG. 13D. Potentiated startle reflex in the pre-pulse inhibition assay in 4EPS-treated mice compared to controls. Data show the average intensity of startle in response to a 120 db pulse (left) and percent inhibition of the pulse when it is preceded by a 5 db or 15 db pre-pulse (right). n=10. Data are presented as mean±SEM. *p<0.05, **p<0.01, S=saline+vehicle, P=poly(I:C)+vehicle, P+BF=poly(I:C)+B. fragilis, SPF=specific pathogen-free (conventionally-colonized), GF=germ-free, Veh.=vehicle (saline), 4EPS=4-ethylphenylsulfate.

FIG. 14A. Diagram illustrating the synthesis of 4EPS (found elevated in MIA serum and restored by B. fragilis treatment) and p-cresol (reported to be elevated in urine of individuals with ASD) by microbial tyrosine metabolism and host sulfation. FIG. 14B. Diagram illustrating the synthesis of indolepyruvate (found elevated in MIA serum and restored by B. fragilis treatment) and indolyl-3-acryloylglycine (reported to be elevated in urine of individuals with ASD) from microbial tryptophan metabolism and host glycine conjugation. Solid arrows represent known biological conversions. Dotted arrow represents predicted biological conversions.

FIG. 15A. Diagram of 4EPS synthesis by treating 4-ethylphenol with sulfur trioxide-pyridine in refluxing benzene to generate the pyridinium salt followed by ion exchange over K+ resin to generate the potassium salt. FIG. 15B. Dose-response curve and linear regression analysis for known concentrations of potassium 4EPS analyzed by LC/MS. FIG. 15C. Time-dependent increases in serum 4EPS after a single i.p. injection of 30 mg/kg potassium 4EPS into adult wild-type mice. FIG. 15D. Communicative behavior, as measured by total number (left), average duration (middle) and total duration (right) of ultrasonic vocalizations produced by adult male mice during a 10-minute social encounter. n=5. FIG. 15E. Repetitive burying of marbles in a 3×6 array during a 10-minute trial. n=10. Data are presented as mean±SEM. Veh.=vehicle (saline), 4EPS=4-ethylphenylsulfate.

DETAILED DESCRIPTION

Figure 1:
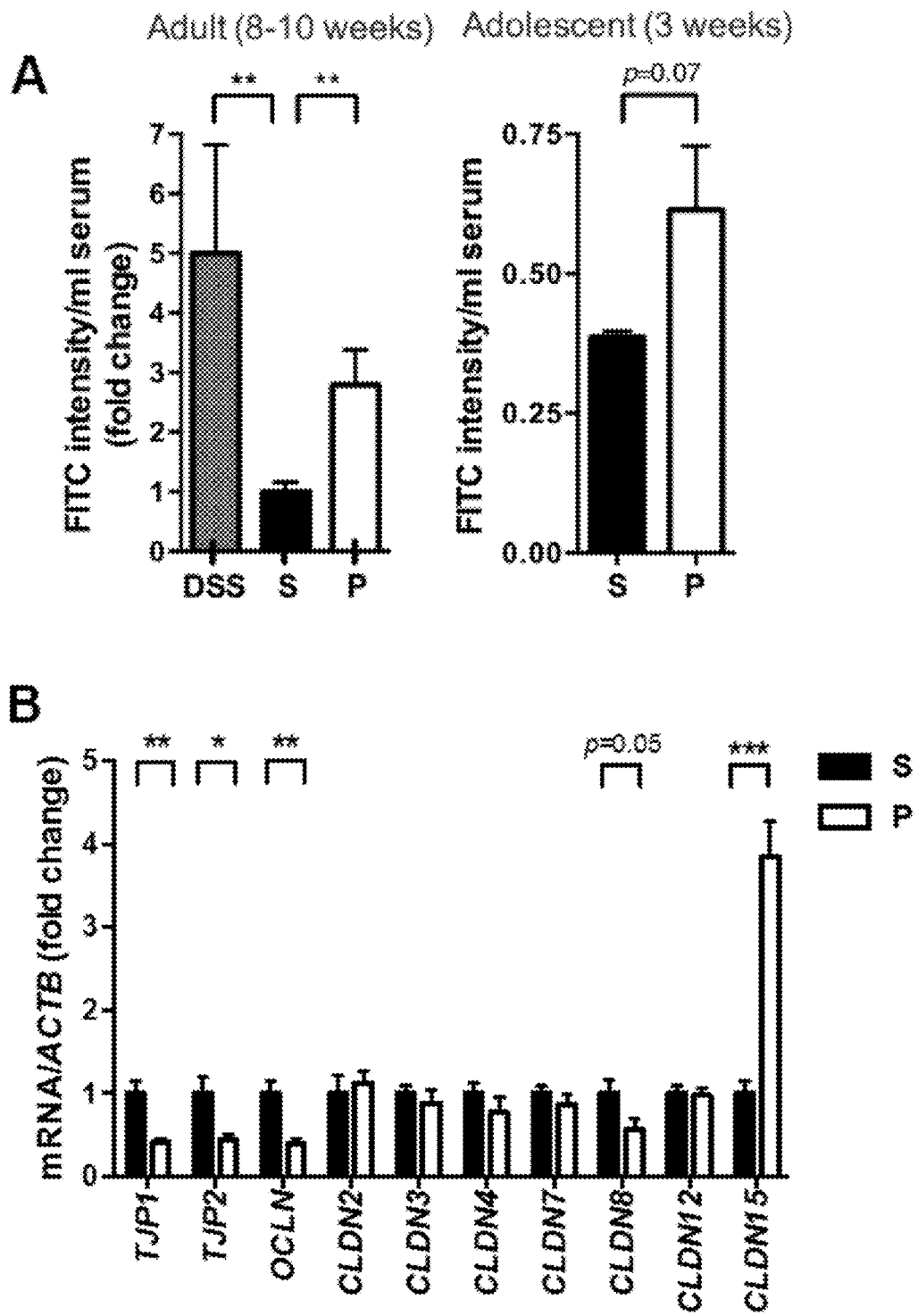
FIG. 1. MIA offspring exhibit deficient GI barrier integrity and abnormal expression of tight junction components and cytokines.
Figure 1:
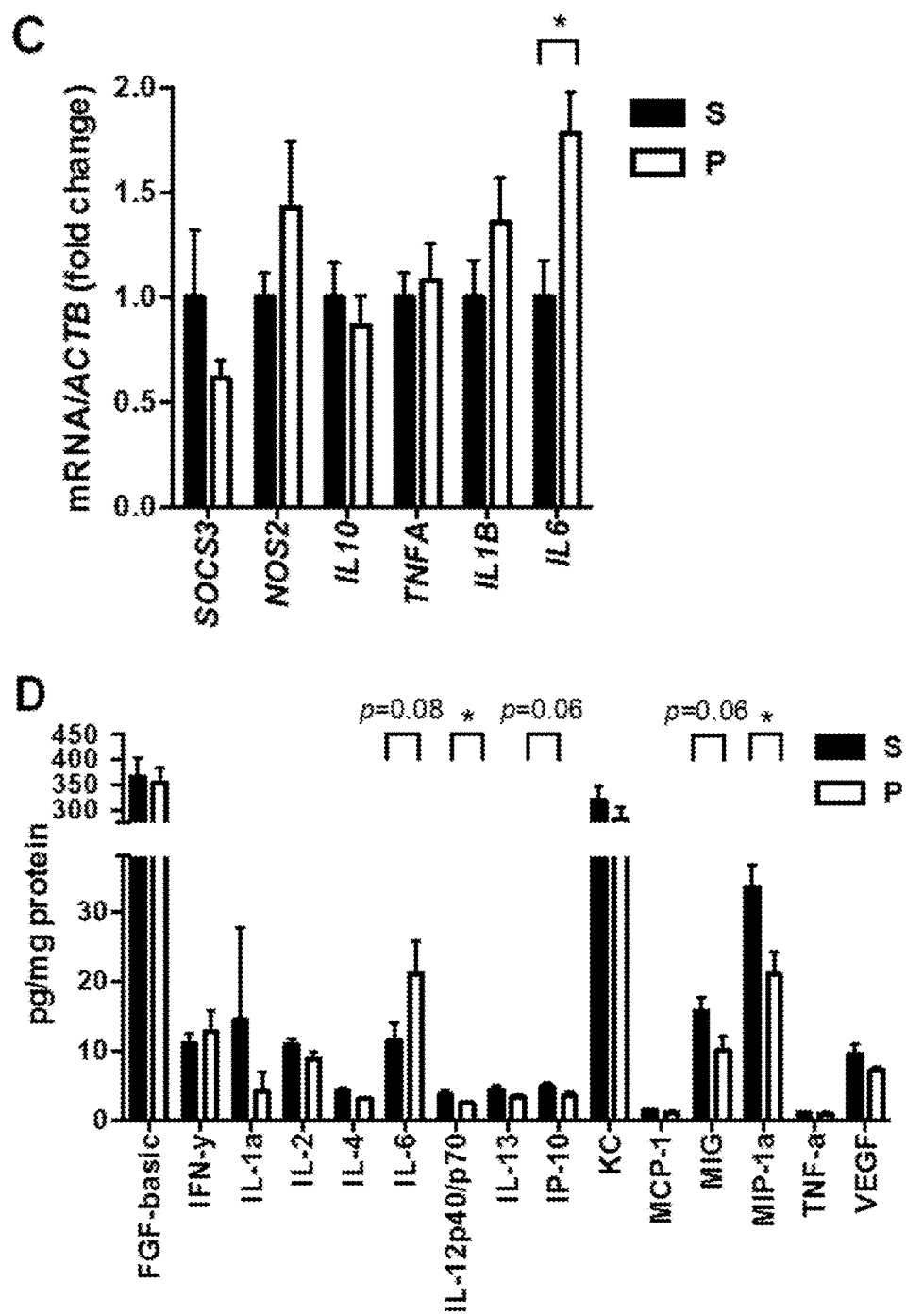

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Autism spectrum disorder (ASD) is a serious neurodevelopmental disorder characterized by stereotypic behaviors and deficits in language and social interaction. As described herein, various metabolites are related to ASD. The level of these metabolites in a subject can be determined and used to diagnose ASD, or adjusted for treating ASD, such as by improving behavioral performance of the subject. In addition, as described herein, various metabolites are responsive to B. fragilis treatment, and those metabolites can be used to assess the susceptibility of a subject suffering from ASD to probiotic treatment.

In some embodiments, the level of the metabolite in the circulation of a subject in need of treatment is determined and adjusted to improve behavioral performance in the subject. The subject in need of treatment can be a subject suffering from anxiety, ASD, or a pathological condition with one or more of the symptoms of ASD. The level of the metabolite in the circulation of the subject can be the blood level, for example the serum level or plasma level, of the metabolite. In some embodiments, the urine or fecal level of the metabolite in the subject is determined and adjusted to improve behavioral performance in the subject.

In some embodiments, the level of the metabolite in the circulation of a subject is detected and compared with a reference level of the metabolite in non-autistic population to diagnose whether the subject has ASD or not. The level of the metabolite in the circulation of the subject can be the blood level, for example the serum level or plasma level, of the metabolite.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "subject" is a vertebrate, such as a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is human.

As used herein, the term "condition/disorder/symptom" or "behavioral abnormality" refers to a symptom expressed by a subject including but not limited to anxiety, Fragile X, Rett syndrome, tuberous sclerosis, obsessive compulsive disorder, attention deficit disorder, schizophrenia, autistic disorder (classic autism), Asperger's disorder (Asperger syndrome), pervasive developmental disorder not otherwise specified (PDD-NOS), childhood disintegrative disorder (CDD), or a pathological condition with one or more of the symptoms of ASD.

As used herein, the term "subject in need of the treatment" refers to a subject expressing or suffering from one or more of the behavioral disorder/symptoms mentioned above. An appropriately qualified person is able to identify such an individual in need of treatment using standard behavioral testing protocols/guidelines. The same behavioral testing protocols/guidelines can also be used to determine whether there is improvement to the individual's disorder and/or symptoms.

As used herein, the term "improvement in behavioral performance" refers prevention or reduction in the severity or frequency, to whatever extent, of one or more of the behavioral disorders, symptoms and/or abnormalities expressed by individual suffering from anxiety, ASD, or a pathological condition with one or more of the symptoms of ASD. Non-limiting examples of the behavioral symptom include repetitive behavior, decreased prepulse inhibition (PPI), and increased anxiety. The improvement is either observed by the individual taking the treatment themselves or by another person (medical or otherwise).

As used herein, the term "treatment" refers to a clinical intervention made in response to a disease, disorder or physiological condition manifested by a patient, particularly a patient suffering from ASD. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may improve behavioral performance of the subject, including ASD-related behaviors. As used herein, the term "prevention" refers to any activity that reduces the burden of the individual later expressing those behavioral symptoms. This takes place at primary, secondary and tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The pharmaceutically acceptable or appropriate carrier may include other compounds known to be beneficial to an impaired situation of the GI tract, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

As used herein, the term "neutraceutical" refers to a food stuff (as a fortified food or a dietary supplement) that provides health benefits. Nutraceutical foods are not subject to the same testing and regulations as pharmaceutical drugs.

As used herein, the term "probiotic" refers to live microorganisms, which, when administered in adequate amounts, confer a health benefit on the host. The probiotics may be available in foods and dietary supplements (for example, but not limited to capsules, tablets, and powders). Non-limiting examples of foods containing probiotic include dairy products such as yogurt, fermented and unfermented milk, smoothies, butter, cream, hummus, kombucha, salad dressing, miso, tempeh, nutrition bars, and some juices and soy beverages.

As used herein, the term "metabolite" refers to any molecule involved in metabolism. Metabolites can be products, substrates, or intermediates in metabolic processes. For example, the metabolite can be a primary metabolite, a secondary metabolite, an organic metabolite, or an inorganic metabolite. Metabolites include, without limitation, amino acids, peptides, acylcarnitines, monosaccharides, lipids and phospholipids, prostaglandins, hydroxyeicosatetraenoic acids, hydroxyoctadecadienoic acids, steroids, bile acids, and glycolipids and phospholipids.

As used herein, the term "cytokine" refers to a secreted protein or active fragment or mutant thereof that modulates the activity of cells of the immune system. Examples of cytokines include, without limitation, interleukins, interferons, chemokines, tumor necrosis factors, colony-stimulating factors for immune cell precursors, and the like.

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or $F(ab')_2$, and Fv). For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6.

Autism Spectrum Disorder (ASD)

Autism spectrum disorders (ASDs) are complex neurodevelopmental disabilities characterized by stereotypic behaviors and deficits in communication and social interaction. The term "spectrum" refers to the wide range of symptoms, skills, and levels of impairment, or disability, that patients with ASD can have. ASD is generally diagnosed according to guidelines listed in the Diagnostic and Statistical Manual of Mental Disorders, Fourth Edition—Text Revision (DSM-IV-TR). The manual currently defines five disorders, sometimes called pervasive developmental disorders (PDDs), as ASD, including Autistic disorder (classic autism), Asperger's disorder (Asperger syndrome), Pervasive developmental disorder not otherwise specified (PDD-NOS), Rett's disorder (Rett syndrome), and Childhood disintegrative disorder (CDD). Some patients are mildly impaired by their symptoms, but others are severely disabled. ASD encompasses a set of complex disorders with poorly defined etiologies, and no targeted cure Recent studies highlight striking neural and peripheral immune dysregulation in autistic individuals. Among several comorbidities in ASD, gastrointestinal (GI) distress is of particular interest, given its prevalence and correlation with the severity of core autism behaviors (Adams et al., 2011; Buie et al., 2010; Coury et al., 2012; Gorrindo et al., 2013; Ibrahim et al., 2009; Wang et al., 2011). A significant subset of ASD children exhibit gastrointestinal (GI) complications, including increased intestinal permeability (or "leaky gut" and altered composition of intestinal microbiota (Buie et al., 2010; Coury et al., 2012; D'Eufemia et al., 1996; de Magistris et al., 2010; de Magistris et al., 2013; Ibrahim et al., 2009). Moreover, a recent multicenter study of over 14,000 ASD individuals reports a higher prevalence of inflammatory bowel disease (IBD) and other GI disorders in ASD patients compared to controls (Kohane et al., 2012). Altered nutrient intake, food allergies and metabolic disruptions are also associated with ASD, and antibiotic treatment and restricted diet are reported to provide behavioral improvements for some autistic children (Buie et al., 2010).

Maternal immune activation (MIA) is an important environmental risk factor for ASD. Several large epidemiological studies have linked maternal viral and bacterial infection with increased autism risk in the offspring ((Atladottir et al., 2010; Gorrindo et al., 2012). Modeling this risk factor in mice by injecting pregnant females with the viral mimic poly(I:C) has been show to yield offspring that exhibit the core behavioral symptoms of autism, including the hallmark symptoms of repetitive/compulsive behaviors, as well as a common autism neuropathology (spatially restricted deficits in Purkinje cells) ((Boksa, 2010; Malkova et al., 2012; Schwartzer et al., 2013; Shi et al., 2009). Recently, MIA offspring have also been found to exhibit abnormalities in the immune system and the gastrointestinal tract.

Humans are colonized with a great abundance and diversity of microbes, which play a critical role in regulating health and disease. Dysbiosis of the commensal microbiota is implicated in the pathogenesis of several human ailments, including IBD, obesity and cardiovascular disease (Blumberg and Powrie, 2012; Clemente et al., 2012). Commensal bacteria also affect a variety of complex behaviors, including social, emotional, nociceptive and anxiety-like behaviors (Amaral et al., 2008; Bravo et al., 2011; Desbonnet et al., 2013; Heijtz et al., 2011), and contribute to brain development and function in mice (Al-Asmakh et al., 2012; Collins et al., 2012; Cryan and Dinan, 2012) and humans (Tillisch et al., 2013). Long-range interactions between the gut microbiota and brain underlie the ability of microbe-based therapies to treat symptoms of multiple sclerosis and depression in mice (Bravo et al., 2011; Hooper et al., 2012; Ochoa-Reparaz et al., 2010) and the reported efficacy of probiotics in treating emotional symptoms of chronic fatigue syndrome and psychological distress in humans (Messaoudi et al., 2011; Rao et al., 2009).

Numerous abnormalities related to the microbiota have been identified in autistic individuals, including disrupted community composition (Adams et al., 2011; Finegold, 2011; Finegold et al., 2010; Finegold et al., 2012; Gondalia et al., 2012; Parracho et al., 2005b; Williams et al., 2011; Williams et al., 2012) and altered peripheral levels of microbially-derived metabolites (Altieri et al., 2011; Frye et al., 2013; MacFabe, 2012; Ming et al., 2012b; Yap et al., 2010a).

Methods for Improving Behavioral Performance

Methods for improving behavioral performance in a subject in need of treatment are provided herein. The subject in need of treatment can be a subject suffering from anxiety, ASD, or a pathological condition with one or more of the symptoms of ASD.

The methods, in some embodiments, include: determining the blood level of an ASD-related metabolite in a subject in need of treatment; and adjusting the blood level of the ASD-related metabolite in the subject until an improvement in the behavioral performance in the subject is observed.

The methods, in some embodiments, include: determining the level of an autism spectrum disorder (ASD)-related metabolite in a subject in need of treatment; and adjusting the level of the ASD-related metabolite in the subject so that the level of the metabolite in the subject is substantially the same as a reference level of the metabolite in non-autistic subjects, thereby improving behavioral performance in the subject. In some embodiments, the methods can further include determining a reference level of the ASD-related metabolite in a population of non-autistic subjects.

In some embodiments, the methods include: determining the level of an autism spectrum disorder (ASD)-related metabolite in a subject in need of treatment; and adjusting the level of the ASD-related metabolite in the subject so that the level of the metabolite in the subject is substantially the same as a reference level of the metabolite in a population of subjects that do not suffer ASD, anxiety or any pathological condition with one or more of the symptoms of ASD, thereby improving behavioral performance in the subject. In some embodiments, the methods can further include determining a reference level of the ASD-related metabolite in subjects that do not suffer from ASD, anxiety or any pathological condition with one or more of the symptoms of ASD.

The methods disclosed herein, in some embodiments, can also include measuring a baseline of behavioral performance prior to adjusting the level of the ASD-related metabolite in the subject in need of treatment and/or measuring the behavioral performance after adjusting the level of the ASD-related metabolite in the subject in need of treatment. In some embodiments, the methods can include comparing the behavioral performance prior to and after adjusting the level of the ASD-related metabolite in the subject in need of treatment, and the comparison can be used to determine if and to what extent the behavioral performance in the subject is improved.

In the method disclosed herein, behavioral performance can be measured and evaluated using various parameters and methods. For example, behavioral test can be conducted to determine the presence and/or extent of restricted repetitive behavior and/or stereotyped behavior patterns of the subject under test. In some embodiments, the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS) is used for the behavioral test. The behavioral test can include, but is not limited to, detecting the presence and/or extent of 1) preoccupation with one or more stereotyped and restricted patterns of interest that is abnormal in either intensity or focus, 2) inflexible adherence to specific, nonfunctional routines or rituals, c) stereotyped and repetitive motor mannerisms (such as hand flapping, finger flapping etc.), and/or d) persistent preoccupation with parts of objects. Non-limiting examples of behavior that can be included in a behavioral test and suggest a need for improving behavioral performance in the subject under the test include: a) sensory behaviors, including poor use of visual discrimination when learning, seems not to hear, so that a hearing loss is suspected, sometimes shows no "startle response" to loud noise", sometimes painful stimuli such as bruises, cuts, and injections evoke no reaction, often will not blink when bright light is directed toward eyes, covers ears at many sounds, squints, frowns, or covers eyes when in the presence of natural light, frequently has no visual reaction to a "new" person, stares into space for long periods of time; b) relating behaviors: frequently does not attend to social/environmental stimuli, has no social smile, does not reach out when reached for, non-responsive to other people's facial expressions/feelings, actively avoids eye contact, resists being touched or held, is flaccid when held in arms, is stiff and hard to held, does not imitate other children at play, has not developed any friendships, often frightened or very anxious, "looks through" people; c) body and object use behaviors: whirls self for long periods of time, does not use toys appropriately, insists on keeping certain objects with him/her, rocks self for long periods of time, does a lot of lunging and darting, flaps hands, walks on toes, hurts self by banging head, biting hand, etc. . . . , twirls, spins, and bangs objects a lot, will feel, smell, and/or taste objects in the environment, gets involved in complicated "rituals" such as lining things up, etc. . . . , is very destructive; and d) language behaviors: does not follow simple commands given once, has pronoun reversal, speech is atonal, does not respond to own name when called out among two others, seldom says "yes" or "I", does not follow simple commands involving prepositions, gets desired objects by gesturing, repeats phrases over and over, cannot point to more than five named objects, uses 0-5 spontaneous words per day to communicate wants and needs, repeats sounds or words over and over, echoes questions or statements made by others, uses at least 15 but less than 30 spontaneous phrases daily to communicate, learns a simple task but "forgets" quickly, strong reactions to changes in routine/environment, has "special abilities" in one area of development, which seems to rule out mental retardation, severe temper tantrums and/or frequent minor tantrums, hurts others by biting, hitting, kicking, etc. . . . , does not wait for needs to be met, difficulties with toileting, does not dress self without frequent help, frequently unaware of surroundings, and may be oblivious to dangerous situations, prefers to manipulate and be occupied with inanimate things, and A developmental delay was identified at or before 30 months of age. One of ordinary skill in the art would appreciate that the attending physician would know how to identify a subject in need of treatment disclosed herein.

After adjustment, the level of the ASD-related metabolite in the subject can about 50%, about 60%, about 70%, about 80%, about 90%, about 95%, about 98%, about 99%, about 100%, about 101%, about 102%, about 105%, about 110%, about 120%, about 130%, about 140%, about 150%, or a range between any two of these values of the reference level of the metabolite in non-autistic subjects. In some embodiments, the level of the ASD-related metabolite in the subject is about 80%, about 90%, about 95%, about 98%, about 99%, about 100%, about 101%, about 102%, about 105%, about 110%, about 120%, or a range between any two of these values of the reference level of the metabolite in non-autistic subjects. In some embodiments, the level of the ASD-related metabolite in the subject is about 95%, about 98%, about 99%, about 100%, about 101%, about 102%, about 105%, or a range between any two of these values of the reference level of the metabolite in non-autistic subjects. The level of the metabolite can be the level of the metabolite in circulation of the subject. For example, the level of the metabolite can be the level of the metabolite in blood or other body fluids (e.g., cerebrospinal fluid, pleural fluid, amniotic fluid, semen, or saliva) of the subject. In some embodiments, the level of the metabolite is the blood level of the metabolite in the subject. The blood level of the metabolite can be, for example, serum level or plasma level of the metabolite. In some embodiments, the level of the metabolite is the urine level of the metabolite in the subject.

In some embodiments, the subject suffers from anxiety, ASD, or a pathological condition with one or more of the symptoms of ASD. Non-limiting examples of ASD include Autistic disorder (classic autism), Asperger's disorder (Asperger syndrome), Pervasive developmental disorder not otherwise specified (PDD-NOS), Rett's disorder (Rett syndrome), and Childhood disintegrative disorder (CDD). In some embodiments, the subject suffers from ASD. In some embodiments, the subject suffers from autism.

Various methods can be used to adjust the level, for example blood level, of the ASD-related metabolite in the subject. In some embodiments, the level, for example blood level, of the metabolite is adjusted by adjusting the composition of gut microbiota in the subject. Adjustment of the composition of gut microbiota in the subject can be achieved by, for example, fecal transplantation (also known as fecal microbiota transplantation (FMT), fecal bacteriotherapy or stool transplant). Fecal transplantation can include a process of transplantation of fecal bacteria from a healthy donor, for example a non-autistic subject, to a recipient (e.g., a subject suffering from autism). The procedure of fecal transplantation can include single or multiple infusions (e.g., by enema) of bacterial fecal flora from the donor to the recipient.

In some embodiments, adjusting the composition of gut microbiota in the subject includes administering the subject a composition comprising bacteria, for example, a composition comprising *Bacteroides* bacteria. The *Bacteroides* bacteria that can be used in the method disclosed herein is not particularly limited. In some embodiments, the *Bacteroides* bacteria comprise *B. fragilis, B. thetaiotaomicron, B. vulgatus*, or a mixture thereof. In some embodiments, the *Bacteroides* bacteria can be *B. fragilis*. The composition comprising bacteria, for example a composition comprising *Bacteroides* bacteria, can be administered to the subject via various routes. For example, the composition can be administered to the subject via oral administration, rectum administration, transdermal administration, intranasal administration or inhalation. In some embodiments, the composition is administered to the subject orally. The composition comprising bacteria, such as *Bacteroides* bacteria, can also be in various forms. For example, the composition can be a probiotic composition, a neutraceutical, a pharmaceutical composition, or a mixture thereof. In some embodiments, the composition is a probiotic composition. Each dosage for human and animal subjects preferably contains a predetermined quantity of the bacteria calculated in an amount sufficient to produce the desired effect. The actual dosage forms will depend on the particular bacteria employed and the effect to be achieved. The composition comprising bacteria, for example, a composition comprising *Bacteroides* bacteria, can be administered alone or in combination with one or more additional probiotic, neutraceutical, or therapeutic agents. Administration "in combination with" one or more further additional probiotic, neutraceutical, or therapeutic agents includes both simultaneous (at the same time) and consecutive administration in any order. Administration can be chronic or intermittent, as deemed appropriate by the supervising practitioner, particularly in view of any change in the disease state or any undesirable side effects. "Chronic" administration refers to administration of the composition in a continuous manner while "intermittent" administration refers to treatment that is done with interruption.

In some embodiments, adjusting the composition of gut microbiota in the subject includes reducing the level of one or more bacterial species in the subject. For example, the level of Clostridia bacteria (such as Lachnospiraceae) in the subject can be reduced to adjust the composition of gut microbiota in the subject. In some embodiments, the Lachnospiraceae is *Roseburia*. The level of Bacterioidia bacteria (such as Bacteroidales 524-7) can also be reduced to adjust the composition of gut microbiota in the subject. In some embodiments, the Clostridia bacteria is Lachnospiraceae. Various methods can be used to reduce the level of one or more bacteria species in the subject. For example, a reduced carbohydrate diet can be provided to the subject to reduce one or more intestinal bacterial species. Without being bound to any specific theory, it is believed that a reduced carbohydrate diet can restrict the available material necessary for bacterial fermentation to reduce intestinal bacterial species.

In some embodiments, adjusting the composition of gut microbiota in the subject includes increasing the level of one or more bacterial species in the subject. For example, the level of Ruminococcaceae, Erysipelotrichaceae, and/or Alcaligenaceae bacteria in the subject can be increased to adjust the composition of gut microbiota in the subject.

ASD-Related Metabolites

As used herein, the term "autism spectrum disorder (ASD)-related metabolite" refers to a metabolite whose level is altered in a subject suffering from ASD, anxiety, and/or any pathological condition with one or more of the symptoms of ASD as compared to a non-autistic subject and/or a subject that does not suffer from ASD, anxiety or any pathological condition with one or more of the symptoms of ASD. For example, the level of the metabolite may be altered in circulation of the subject suffering from ASD as compared to a non-autistic subject. In some embodiments, the level of the metabolite is altered in blood, serum, plasma, body fluids (e.g., cerebrospinal fluid, pleural fluid, amniotic fluid, semen, or saliva), urine, and/or feces of the subject suffering from ASD as compared to a non-autistic subject. In some instances, the ASD-related metabolite plays a causative role in the development of ASD-related behaviors in the subject suffering from ASD. In some instances, the alteration in the level of ASD-related metabolite is caused by ASD. The ASD-related metabolite can have an increased or decreased level in the subject suffering from ASD as compared to a non-autistic subject or a subject that does not suffer from ASD, anxiety or any pathological condition with one or more of the symptoms of ASD.

One of ordinary skill in the art will appreciate that variability in the level of metabolites may exist between individuals, and a reference level can be established as a value representative of the level of the metabolites in a non-autistic population, or a population of subjects that do not suffer from ASD, anxiety or any pathological condition with one or more of the symptoms of ASD, for the comparison. Various criteria can be used to determine the inclusion and/or exclusion of a particular subject in the reference population, including age of the subject (e.g. the reference subject can be within the same age group as the subject in need of treatment) and gender of the subject (e.g. the reference subject can be the same gender as the subject in need of treatment). In some embodiments, the ASD-related metabolite has an increased level in the subject suffering from ASD as compared to the reference level. In some embodiments, the ASD-related metabolite has a decreased level in the subject suffering from ASD as compared to the reference level. In some embodiments, the alteration in the level of ASD-related metabolite can be restored partially or fully by adjusting the composition of gut microbiota in the subject suffering from ASD.

Non-limiting examples of ASD-related metabolites are provided in Table 1.

TABLE 1

Exemplary ASD-related metabolites

| | | |
|---|---|---|
| N-acetylserine | beta-alanine | 4-methyl-2-oxopentaoate |
| imidazole propionate | phenol sulfate | 5-methylthioadenosine |
| serotonin | 3-methyl-2-oxovalerate | docosapentaenoate (n3 DPA; 22:5n3) |
| arginine | ornithine | docosapentaenoate (n6 DPA; 22:5n6) |
| glycylvaline | eicosenoate | dihomo-linoleate (20:2n6) |
| xylose | octadecanedioate | docosahexaenoate (DHA; 22:6n3) |
| stearate | pantothenate | 1-pentadecanoylglycerophosphocholine |
| 13-HODE + 9-HODE | ergothioneine | 1-oleoylglycerophosphoethanolamine |
| bilirubin (E,E) | glycolate (hydroxyacetate) | 4-ethylphenylsulfate |
| equol sulfate | transurocanate | 1-palmitoylglycerophosphoethanolamine |
| glutamine | indolepyruvate | 1-stearoylglycerophosphoinositol |
| adrenate | 3-phosphoglycerate | 1-palmitoleoylglycerophosphocholine |
| myo-inositol | phenylacetylglycine | 1-palmitoylplasmenylethanolamine |
| cysteine | phosphoenolpyruvate | Peptide TDTEDKGEFLSEGGGVR (SEQ ID NO. 5) |
| ribose | 12-HETE | 4-methylphenylsulfate |
| 4-methylphenyl | Indolyl-3-acryloylglycine | 4-ethylphenyl |

The ASD-related metabolites are involved in various metabolic pathways. Examples of metabolic pathways that the ASD-related metabolite can be involved in include, but are not limited to, amino acid metabolism, protein metabolism, carbohydrate metabolism, lipid metabolism, and metabolism of cofactors and vitamins. For example, the ASD-related metabolite can be a metabolite involved in glycine, serine and threonine metabolism; alanine and aspartate metabolism; glutamate metabolism; histidine metabolism; phenylalanine and tyrosine metabolism; tryptophan metabolism; valine, leucine and isoleucine metabolism; cysteine, methionine, SAM, and taurine metabolism; urea cycle; arginine-, proline-metabolism; and/or polyamine metabolism. The ASD-related metabolite can also be a dipeptide or fibrinogen cleavage peptide. In addition, the ASD-related metabolite can be a metabolite involved in glycolysis, gluconeogenesis, pyruvate metabolism; and/or nucleotide sugars, pentose metabolism. The ASD-related metabolite can also be a metabolite involved in essential fatty acid, long chain fatty acid, monohydroxy and/or dicarboxylate fatty acid, eicosanoid, inositol, and/or lysolipid metabolism. The ASD-related metabolite can be a metabolite involved in hemoglobin and porphyrin metabolism, pantothenate and CoA metabolism, and/or benzoate metabolism.

In some embodiments, an ASD-related metabolite is a metabolite involved in tryptophan metabolism, a metabolite involved in fatty acid metabolism, or a metabolite involved in purine metabolism. In some embodiments, an ASD-related metabolite is glycolate, imidazole propionate, or N-acetylserine. In some embodiments, an ASD-related metabolite is 4-ethylphenylsulfate (4EPS), 4-ethylphenyl, indolepyruvate, indolyl-3-acryloylglycine, or serotonin. In some embodiments, an ASD-related metabolite is 4-methylphenylsulfate or 4-methylphenyl.

In some embodiments, the level of one ASD-related metabolite is adjusted or improving behavioral performance in the subject. For example, the level of 4EPS or indolepyruvate in the subject, for example the blood level (e.g., serum level) of 4EPS and indolepyruvate, can be adjusted for improving behavioral performance of the subject. In some embodiments, the level of two or more ASD-related metabolites is adjusted for improving behavioral performance in the subject. For example, the level of 4EPS and indolepyruvate in the subject, for example the blood level (e.g., serum level) of 4EPS and indolepyruvate, can be adjusted for improving behavioral performance of the subject.

Various methods can be used to adjust the level, for example blood level (e.g., serum level) or urine level, of the ASD-related metabolite in the subject for improving behavioral performance of the subject. For example, an antibody that specifically binds the ASD-related metabolite, an intermediate for the in vivo synthesis of the ASD-related metabolite, or a substrate for the in vivo synthesis of the ASD-related metabolite can be administered to the subject to adjust the level of the ASD-related metabolite in the subject. For example, an antibody that specifically binds 4EPS and/or one or more of the substrates and intermediates in the in vivo 4EPS synthesis can be used to reduce the level of 4EPS in the subject. In some embodiments, an antibody that specifically binds tyrosine, hydroxyphenylpyruvic acid, p-coumaric acid, p-vinylphenynol, hydroxyphenylpropionate, and/or 4-ethylphenol is administered to the subject to reduce the level of 4EPS in the subject. In some embodiments, an antibody that specifically binds 4EPS is administered to the subject to reduce the level of 4EPS in the subject. As another example, an antibody that specifically binds 4-methylphenylsulfate and/or one or more of the substrates and intermediates in the in vivo 4-methylphenylsulfate synthesis can be used to reduce the level of 4-methylphenylsulfate in the subject. In some embodiments, an antibody that specifically binds tyrosine, hydroxyphenylpyruvic acid, hydroxyphenylpropionate, hydroxyphenylacetate, and/or p-cresol is administered to the subject to reduce the level of 4-methylphenylsulfate, e.g., the urine level of 4-methylphenylsulfate, in the subject. In some embodiments, an antibody that specifically binds 4-methylphenylsulfate is administered to the subject to reduce the level of 4-methylphenylsulfate in the subject. As yet another example, an antibody that specifically binds indolyl-3-acryloylglycine and/or one or more of the substrates and intermediates in the in vivo indolyl-3-acryloylglycine synthesis can be used to reduce the level of indolyl-3-acryloylglycine in the subject. In some embodiments, an antibody that specifically binds tryptophan, indolepyruvate, and/or indoleacrylic acid is administered to the subject to reduce the level of indolyl-3-acryloylglycine in the subject. In some embodiments, an antibody that specifically binds indolyl-3-acryloylglycine is administered to the subject to reduce the level of indolyl-3-acryloylglycine in the subject. As still yet another example, an antibody that specifically binds tryptophan and indolepyruvate can be used to reduce the level of indolepyruvate in the subject.

Methods for generating antibodies that specifically bind small molecules have been developed in the art. For example, generation of monoclonal antibodies against small molecules has been described in Rufo et al., J. Ag. Food Chem. 52:182-187 (2004), which is hereby incorporated by reference. For example, an animal such as a guinea pig or rat, preferably a mouse, can be immunized with a small molecule conjugated to a hapten (e.g., KLH), the antibody-producing cells, preferably splenic lymphocytes, can be collected and fused to a stable, immortalized cell line, preferably a myeloma cell line, to produce hybridoma cells which are then isolated and cloned. See, e.g., U.S. Pat. No. 6,156,882, which is hereby incorporated by reference. In addition, the genes encoding the heavy and light chains of a small molecule-specific antibody can be cloned from a cell, e.g., the genes encoding a monoclonal antibody can be cloned from a hybridoma and used to produce a recombinant monoclonal antibody.

The level, for example blood level (e.g., serum level) or urine level, of the ASD-related metabolite in the subject can also be adjusted by inhibiting an enzyme involved in the in vivo synthesis of the ASD-related metabolite for improving behavioral performance of the subject.

As described herein, adjusting the level, for example blood level (e.g., serum level), of the ASD-related metabolite in the subject can ameliorate gastrointestinal (GI) distress of the subject suffering from ASD. The GI distress can be abdominal cramps, chronic diarrhea, constipation, intestinal permeability, or a combination thereof. As disclosed herein, amelioration is used in a broad sense to refer to at least a reduction in the magnitude of a parameter, e.g., symptom, associated with the pathological condition being treated. In some embodiments, the method can completely inhibited, e.g., prevented from happening, or stopped, e.g., terminated, such that the host no longer suffers from the pathological condition, or at least one or more of the symptoms that characterize the pathological condition. In some embodiments, the method can delay or slowing of disease progression, amelioration or palliation of the disease state, and remission (whether partial or total), whether detectable or undetectable.

As discussed above, gastrointestinal (GI) distress is an important comorbidity in ASD, given its prevalence and correlation with the severity of core autism behaviors. Also disclosed herein are methods for relieving gastrointestinal (GI) distress of a subject suffering from ASD. The methods can include reducing intestinal permeability in the subject. In some embodiments, the GI distress comprises abdominal cramps, chronic diarrhea, constipation, intestinal permeability, or a combination thereof. Reducing intestinal permeability can be achieved by altering the composition of gut microbiota in the subject. In some embodiments, altering the composition of gut microbiota in the subject comprises administering the subject a composition comprising bacteria, such as *Bacteroides* bacteria. In some embodiments, altering the composition of gut microbiota in the subject comprises fecal transplantation. In some embodiments, altering the composition of gut microbiota in the subject comprises probiotic treatment.

A variety of subjects are treatable. Generally, such subjects are mammals, where the term is used broadly to describe organisms which are within the class mammalia, including the orders carnivore (for example, dogs and cats), rodentia (for example, mice, guinea pigs and rats), and primates (for example, humans, chimpanzees and monkeys). In preferred embodiments, the subjects are humans.

In the methods disclosed herein, the amount of bacteria, for example Bacteroides bacteria (e.g., B. fragilis), administered to the subject in need of treatment can be determined according to various parameters such as the age, body weight, response of the subject, condition of the subject to be treated; the type and severity of the anxiety, ASD, or the pathological conditions with one or more symptoms of ASD; the form of the composition in which the bacteria is included; the route of administration; and the required regimen. The severity of the condition may, for example, be evaluated, in part, by standard prognostic evaluation methods. A program comparable to that discussed above may be used in veterinary medicine. For example, the amount of bacteria can be titrated to determine the effective amount for administering to the subject in need of treatment. One of ordinary skill in the art would appreciate that the attending physician would know how to and when to terminate, interrupt or adjust administration of bacteria due to toxicity or organ dysfunctions. Conversely, the attending physician would also know to adjust treatment to higher levels if the clinical response were not adequate (precluding toxicity).

Methods for Assessing the Susceptibility of an ASD Subject to Probiotic Treatment Methods for assessing the susceptibility of a subject suffering from ASD to probiotic treatment are provided herein. The methods can include: determining the level of a B. fragilis-responsive metabolite in the subject; and comparing the level of the B. fragilis-responsive metabolite in the subject to a reference level of the metabolite in subjects suffering from ASD and one or more gastrointestinal disorders, wherein substantial identity between the blood level of the metabolites in the subject and the reference level indicates that the subject is susceptible to the probiotic treatment, for example B. fragilis probiotic treatment. In some embodiments, the method includes determining the level of two or more B. fragilis-responsive metabolites in the subject; and comparing the level of each of the two or more B. fragilis-responsive metabolites in the subject to the reference level of each of the two or more B. fragilis-responsive metabolites, wherein substantial identity between the blood levels of the metabolites in the subject and the reference levels indicates an increased susceptibility of the subject to the probiotic treatment.

The level of the metabolite can be the level of the metabolite in circulation of the subject. For example, the level of the metabolite is the level of the metabolite in blood or other body fluids (e.g., cerebrospinal fluid, pleural fluid, amniotic fluid, semen, or saliva) of the subject. In some embodiments, the level of the metabolite is the blood level of the metabolite in the subject. The blood level of the metabolite can be, for example, serum level or plasma level of the metabolite. In some embodiments, the level of the metabolite is the urine level of the metabolite in the subject.

B. fragilis-Responsive Metabolites

As used herein, the term "B. fragilis-responsive metabolite" refers to a metabolite whose level has been determined to be altered by B. fragilis treatment. For example, the level of the metabolite may be altered in circulation of the subject after B. fragilis treatment. In some embodiments, the level of the metabolite is altered in blood, serum, plasma, body fluids (e.g., cerebrospinal fluid, pleural fluid, amniotic fluid, semen, or saliva), urine, and/or feces of the subject after B. fragilis treatment. The B. fragilis-responsive metabolite can be increased or decreased in level after B. fragilis treatment. In some instances, the ASD-related metabolite plays a causative role in the improvement of behavioral performance in the ASD subject treated with B. fragilis. In some instances, a B. fragilis-responsive metabolite is also an ASD-related metabolite. In some instances, an ASD-related metabolite is also a B. fragilis-responsive metabolite.

As disclosed herein, B. fragilis-responsive metabolite can be determined by comparing the pre-treatment level of a metabolite in a subject, for example a subject suffering from ASD, with the level of a metabolite in the subject after B. fragilis treatment. One of ordinary skill in the art will appreciate that variability in the level of metabolites may exist between individuals, and a reference level for a B. fragilis-responsive metabolite can be established as a value representative of the level of the metabolites in a population for ASD subjects suffering from one or more GI disorders for the comparison. In some embodiments, the B. fragilis-responsive metabolite has an increased level in the subject suffering from ASD as compared to the reference level. In some embodiments, the B. fragilis-responsive metabolite has a decreased level in the subject suffering from ASD as compared to the reference level.

Non-limiting examples of B. fragilis-responsive metabolites are provided in Table 2.

TABLE 2

| Exemplary B. fragilis-responsive metabolites | |
|---|---|
| sarcosine (N-Methylglycine) | inosine |
| aspartate | adenosine |
| 3-ureidopropionate | adenosine 5'-monophosphate (AMP) |
| glutarate (pentanedioate) | guanosine 5'- monophosphate (5'-GMP) |
| tyrosine | urate |
| 3-(4-hydroxyphenyl)lactate | 2'-deoxycytidine |
| 3-phenylpropionate (hydrocinnamate) | uracil |
| serotonin (5HT) | pseudouridine |
| 3-methyl-2-oxobutyrate | nicotinamide |
| 3-methyl-2-oxovalerate | catechol sulfate |
| 4-methyl-2-oxopentanoate | salicylate |
| isobutyrylcarnitine | equol sulfate |
| 2-methylbutyroylcarnitine | erythritol |
| isovalerylcarnitine | dodecanedioate |
| 2-hydroxybutyrate (AHB) | tetradecanedioate |
| arginine | hexadecanedioate |
| ornithine | octadecanedioate |
| 2-aminobutyrate | undecanedioate |
| 4-guanidinobutanoate | 12-HETE |
| 5-oxoproline | propionylcarnitine |
| glycylvaline | butyrylcarnitine |

TABLE 2-continued

Exemplary *B. fragilis*-responsive metabolites

| | |
|---|---|
| gamma-glutamyltryptophan | valerylcarnitine |
| TDTEDKGEFLSEGGGV | 3-dehydrocarnitine |
| TDTEDKGEFLSEGGGVR | hexanoylcarnitine |
| sorbitol | octanoylcarnitine |
| pyruvate | choline |
| ribitol | chiro-inositol |
| ribose | pinitol |
| ribulose | 3-hydroxybutyrate (BHBA) |
| xylitol | 1,2-propanediol |
| citrate | 1-linoleoylglycerophosphoethanolamine |
| fumarate | 1-arachidonoylglycerophosphoethanolamine |
| malate | 2-arachidonoylglycerophosphoethanolamine |
| linoleate (18:2n6) | 1-stearoylglycerophosphoinositol |
| linolenate [alpha or gamma; (18:3n3 or 6)] | 1-linoleoylglycerophosphoinositol |
| dihomo-linolenate (20:3n3 or n6) | 1-arachidonoylglycerophosphoinositol |
| docosapentaenoate (n3 DPA; 22:5n3) | 1-palmitoylplasmenylethanolamine |
| docosapentaenoate (n6 DPA; 22:5n6) | hypoxanthine |
| docosahexaenoate (DHA; 22:6n3) | eicosenoate (20:1n9 or 11) |
| heptanoate (7:0) | dihomo-linoleate (20:2n6) |
| pelargonate (9:0) | mead acid (20:3n9) |
| laurate (12:0) | adrenate (22:4n6) |
| myristate (14:0) | 8-hydroxyoctanoate |
| palmitate (16:0) | 3-hydroxydecanoate |
| palmitoleate (16:1n7) | 16-hydroxypalmitate |
| margarate (17:0) | 13-HODE + 9-HODE |
| stearate (18:0) | 12,13-hydroxyoctadec-9(Z)-enoate |
| oleate (18:1n9) | 9,10-hydroxyoctadec-12(Z)-enoic acid |
| stearidonate (18:4n3) | adipate |
| suberate (octanedioate) | 2-hydroxyglutarate |
| sebacate (decanedioate) | pimelate (heptanedioate) |
| azelate (nonanedioate) | |

Diagnosis of ASD

Also disclosed herein are methods for diagnosing ASD in a subject. In some embodiments, the methods include: determining the level of a cytokine in gut and the level of one or more ASD-related metabolites in the subject; and detecting whether or not there is an alteration in the level of the cytokine in gut and the level of at least one or more of the ASD-related metabolites in the subject as compared to a reference level of the cytokine and the metabolite in non-autistic subjects, whereby an alteration in the amount of the cytokine in gut and the level of at least one of the one or more metabolites indicates that the subject suffers from ASD.

In some embodiments, the method include: determining the level of an ASD-related metabolite in the subject; and detecting whether or not there is an alteration in the level of the ASD-related metabolite in the subject as compared to a reference level of the metabolite in non-autistic subjects, whereby an alteration in the level of the ASD-related metabolite indicates that the subject suffers from ASD. In some embodiments, the method include: determining the level of two or more ASD-related metabolites in the subject; and detecting whether or not there is an alteration in the level of the two or more ASD-related metabolites in the subject as compared to a reference level of the metabolites in non-autistic subjects, whereby an alteration in the level of at least two of the two or more ASD-related metabolites indicates that the subject suffers from ASD.

As disclosed herein, the level of the ASD-metabolite can be the level of the metabolite in circulation of the subject. For example, the level of the metabolite can be the level of the metabolite in blood or other body fluids (e.g., cerebrospinal fluid, pleural fluid, amniotic fluid, semen, or saliva) of the subject. In some embodiments, the level of the metabolite is the blood level of the metabolite in the subject. The blood level of the metabolite can be, for example, serum level or plasma level of the metabolite. In some embodiments, the level of the metabolite is the urine level of the metabolite in the subject.

One of ordinary skill in the art will appreciate that variability in the level of metabolites and/or the level of cytokines may exist between individuals in a non-autistic population. And thus, a reference level for the metabolite can be established as a value representative of the level of the metabolites in a non-autistic population for the comparison, and a reference level for the cytokine can be established as a value representative of the level of the cytokine in a non-autistic population for the comparison. In some embodiments, the ASD-related metabolite has an increased level in the subject suffering from ASD as compared to the reference level of the ASD-related metabolite. In some embodiments, the ASD-related metabolite has a decreased level in the subject suffering from ASD as compared to the reference level of the ASD-related metabolite. In some embodiments, the level of the cytokine is increased in the subject suffering from ASD as compared to the reference level of the cytokine. In some embodiments, the level of the cytokine is decreased in the subject suffering from ASD as compared to the reference level of the cytokine. The ASD-related metabolites are described herein, and non-limiting examples of the ASD-related metabolites that can be used in the methods are provided in Table 1.

In some embodiments, the cytokine is interleukin-6 (IL-6). In some embodiments, the one or more ASD-related metabolites comprises a metabolite involved in tryptophan metabolism, a metabolite involved in fatty acid metabolism, a metabolite involved in purine metabolism, glycolate, imidazole propionate, N-acetylserine, or any combination thereof. Non-limiting examples of metabolites involved in tryptophan metabolism include 4-ethylphenylsulfate, indolepyruvate, indolyl-3-acryloylglycine, or serotonin. In some embodiments, the ASD-related metabolite is 4-ethylphenylsulfate, indolepyruvate, indolyl-3-acryloylglycine, or serotonin.

In the methods disclosed in the present disclosure, the level of a metabolite in the subject can be determined by any conventional methods known in the art, including but not limited to chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microfluidic chip-based assay, detection of fluorescence, detection of chemiluminescence, or a combination thereof.

EXAMPLES

Some aspects of the embodiments discussed above are disclosed in further detail in the following examples, which are not in any way intended to limit the scope of the present disclosure.

Experimental Material and Methods

The following experimental methods were used for Examples 1-8 described below.

Animals and MIA

Pregnant C57BL/6N (Charles River; Wilmington, Mass.) were selected at random from a larger cohort of pregnant females, and injected i.p. on E12.5 with saline or 20 mg/kg poly(I:C) according to the methods described in Smith et al., 2007. All animal experiments were approved by the Caltech IACUC.

B. fragilis Treatment

At 3 weeks of age, saline and poly(I:C) offspring across individual litters were weaned into cages of 4 non-littermate offspring of the same treatment group to generate a randomized experimental design (Lazic, 2013). Cages within the poly(I:C) versus saline treatment groups were selected at random for treatment with B. fragilis or vehicle, every other day for 6 days. To preclude any confounding effects of early life stress on neurodevelopment and behavior, suspensions were not administered by oral gavage. For B. fragilis treatment, $10^{10}$ cfu freshly grown B. fragilis was suspended in 1 mL 1.5% sodium bicarbonate, mixed with 4 ml sugar-free applesauce and spread over four standard food pellets. For vehicle treatment, saline and poly(I:C) animals were fed 1.5% sodium bicarbonate in applesauce over food pellets. Applesauce and pellets were completely consumed by mice of each treatment group by 48 hours after administration. The same procedure was used for treatment with mutant B. fragilis lacking PSA and B. thetaiotaomicron.

Intestinal Permeability Assay

Adult mice were fasted for 4 hours before oral gavage with 0.6 g/kg 4 kDa FITC-dextran (Sigma Aldrich). 4 hours later, blood samples were collected by cardiac puncture and spun through SST vacutainers (Becton Dickinson). FITC-dextran standards and 3×-diluted sera were immediately read for FITC fluorescence intensity at 521 nm using an xFluor4 spectrometer (Tecan). Mice were fed 3% dextran sulfate sodium salt (DSS; MP Biomedicals) in drinking water for 7 days to chemically induce colitis.

In Vitro Immune Assays

Methods for Treg and Gr-1 flow cytometry and CD4+ T cell in vitro stimulation are described in Hsiao et al., 2012. Briefly, cells were harvested in complete RPMI from spleens and mesenteric lymph nodes. For subtyping of splenocytes, cells were stained with Gr-1 APC, CD11b-PE, CD4-FITC and Ter119-PerCP-Cy5.5 (Biolegend). For detection of Tregs, splenocytes were stimulated for 4 hours with PMA/ionomycin in the presence of GolgiPLUG (BD Biosciences), blocked for Fc receptors and labeled with CD4-FITC, CD25-PE, Foxp3-APC and Ter119-PerCP-Cy5.5. Samples were processed using the FACSCalibur cytometer (BD Biosciences) and analyzed using FlowJo software (TreeStar). For CD4+ T cell stimulation assays, $10^{6}$ CD4+ T cells were cultured in complete RPMI with PMA (50 ng/ml) and ionomycin (750 ng/ml) for 3 days at 37° C. with 5% (vol/vol) $CO_2$. Each day, supernatant was collected for ELISA assays to detect IL-6 and IL-17, according to the manufacturer's instructions (eBioscience).

IL-6 Oral Gavage and In Vitro Colon Culture

For in vivo assays, adult mice were gavaged with 5 ug carrier-free recombinant mouse IL-6 (eBioscience) in 1.5% sodium bicarbonate. At 4 hours post-gavage, 1 cm regions of distal, medial and proximal colon were dissected, washed in HBSS and processed for qRT-PCR, as described above. For in vitro assays, adult mice were sacrificed and 1 cm regions of distal, medial and proximal colon were dissected, washed and bisected for colon culture with 0-80 ng/ml IL-6 in complete RPMI media. After 4 hours of culture, colon pieces were harvested and processed for qRT-PCR, as described above.

Intestinal qRT-PCR, Western Blots, and Cytokine Profiles 1 cm regions of the distal, medial and proximal colon and small intestine were washed in HBSS and either a) homogenized in ice-cold Trizol for RNA isolation and reverse transcription according to Hsiao and Patterson, 2011, or b) homogenized in Tissue Extraction Reagent I (Invitrogen) containing EDTA-free protease inhibitors (Roche) for protein assays. For SYBR green qRT-PCR, validated primer sets were obtained from Primerbank (Harvard). For cytokine profiling, mouse 20-plex cytokine arrays (Invitrogen) were run on the Luminex FLEXMAP 3D platform by the Clinical Immunobiology Correlative Studies Laboratory at the City of Hope (Duarte, Calif.). Western blots were conducted according to standard methods and probed with rabbit anti-claudin 8 or rabbit anti-claudin 15 (Invitrogen) at 1:100 dilution.

Microbial DNA Extraction, 16S rRNA Gene Amplification and Pyrosequencing

Bacterial genomic DNA was extracted from mouse fecal pellets using the MoBio PowerSoil Kit following protocols benchmarked as part of the NIH Human Microbiome Project. The V3-V5 regions of the 16S rRNA gene were PCR amplified using individually barcoded universal primers containing linker sequences for 454-pyrosequencing. Sequencing was performed at the Human Genome Sequencing Center at Baylor College of Medicine using a multiplexed 454-Titanium pyrosequencer.

16S rRNA Gene Sequence Analysis

FASTA and quality files were obtained from the Alkek Center for Metagenomics and Microbiome Research at the Baylor College of Medicine and quality filtered. Sequences <200 bp and >1000 bp, and sequences containing any primer mismatches, barcode mismatches, ambiguous bases, homopolymer runs exceeding six bases, or an average quality score of below 30 were discarded. Quality filtered sequences were then analyzed using the QIIME 1.6 software package (Caporaso et al., 2010b). Sequences were then checked for chimeras and clustered to operational taxonomic units (OTUs) using the USearch pipeline (Edgar, 2010; Edgar et al., 2011) with a sequence similarity index of 97%. OTUs were subsequently assigned taxonomic classification using the basic local alignment search tool (BLAST) classifier (Altschul et al, 1990), based on the small subunit non-redundant reference database release 111 (Quest et al, 2013) with 0.001 maximum e-value. These taxonomies were then used to generate taxonomic summaries of all OTUs at different taxonomic levels. For tree-based alpha- and beta diversity analyses, representative sequences for each OTU were aligned using PyNAST (Caporaso et al., 2010a) and a phylogenetic tree was constructed based on this alignment using FastTree (Price et al., 2009). Alpha diversity estimates (by Observed Species and Faith's phylogenetic diversity [PD]; (Faith, 1992)) and evenness (by Simpson's evenness and Gini Coefficient; (Wittebolle et al., 2009)) were calculated and compared between groups using a nonparametric test based on 100 iterations using a rarefaction of 2082 sequences from each sample. For beta diversity, even sampling of 2160 sequences per sample was used, and calculated using weighted and unweighted UniFrac (Lozupone and Knight, 2005). Beta Diversity was compared in a pairwise fashion (Saline (S) vs Poly(I:C) (P), Poly(I:C) (P) vs Poly (I:C)+B. fragilis treatment (P+BF)) using the Analysis of Similarity (ANOSIM; Fierer et al 2010) with 999 permutations to determine statistical significance.

Identification of Differences in Specific OTUs

Figure 6:
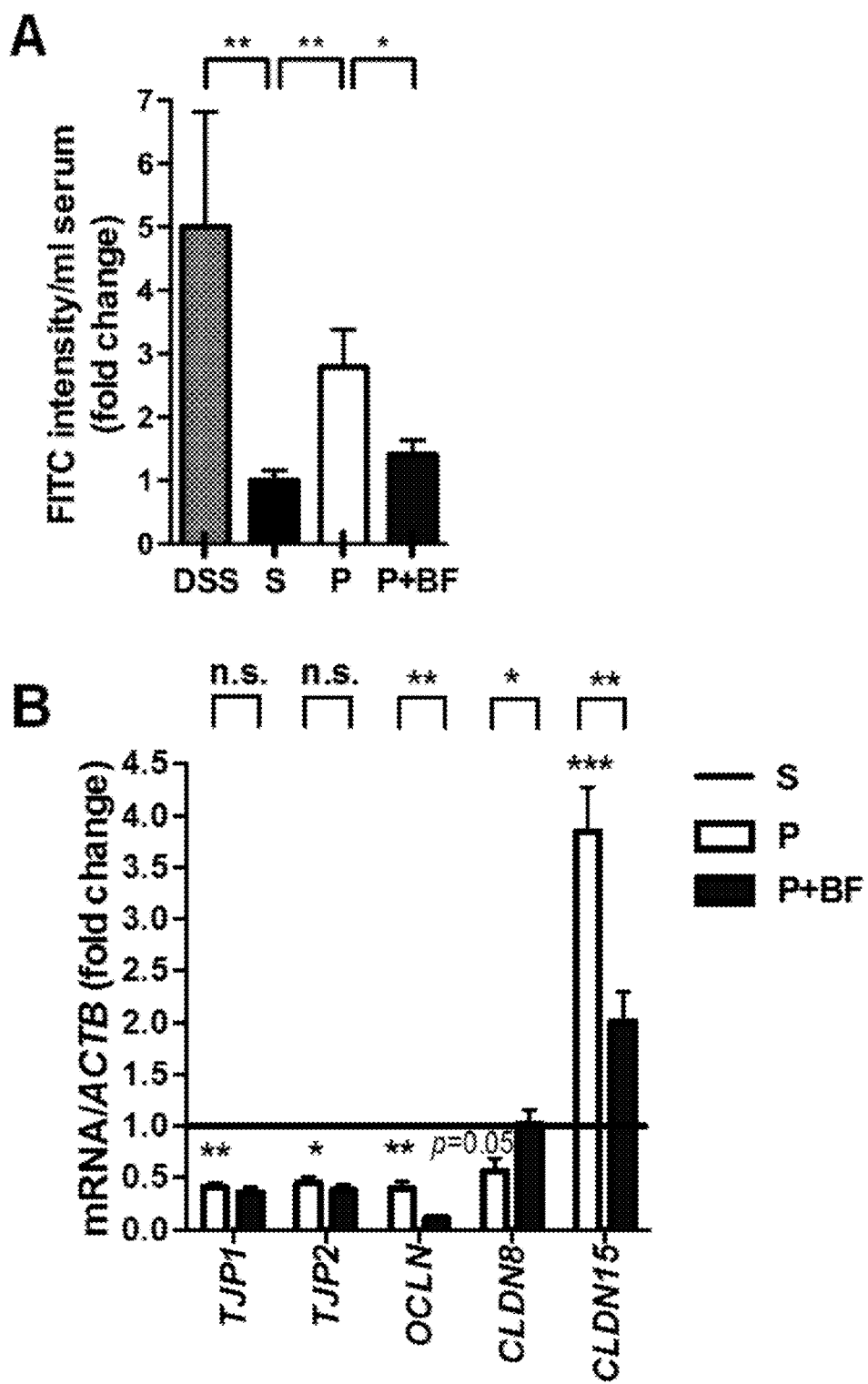
FIG. 6. *B. fragilis* treatment corrects deficits in GI barrier integrity and colon expression of tight junction components and cytokines in MIA offspring.
Figure 6:
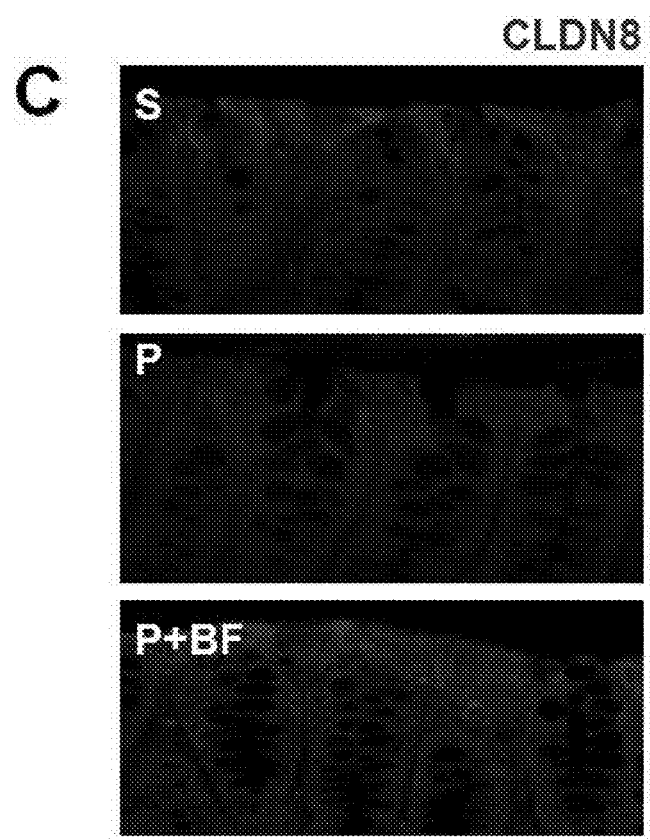
Figure 6:
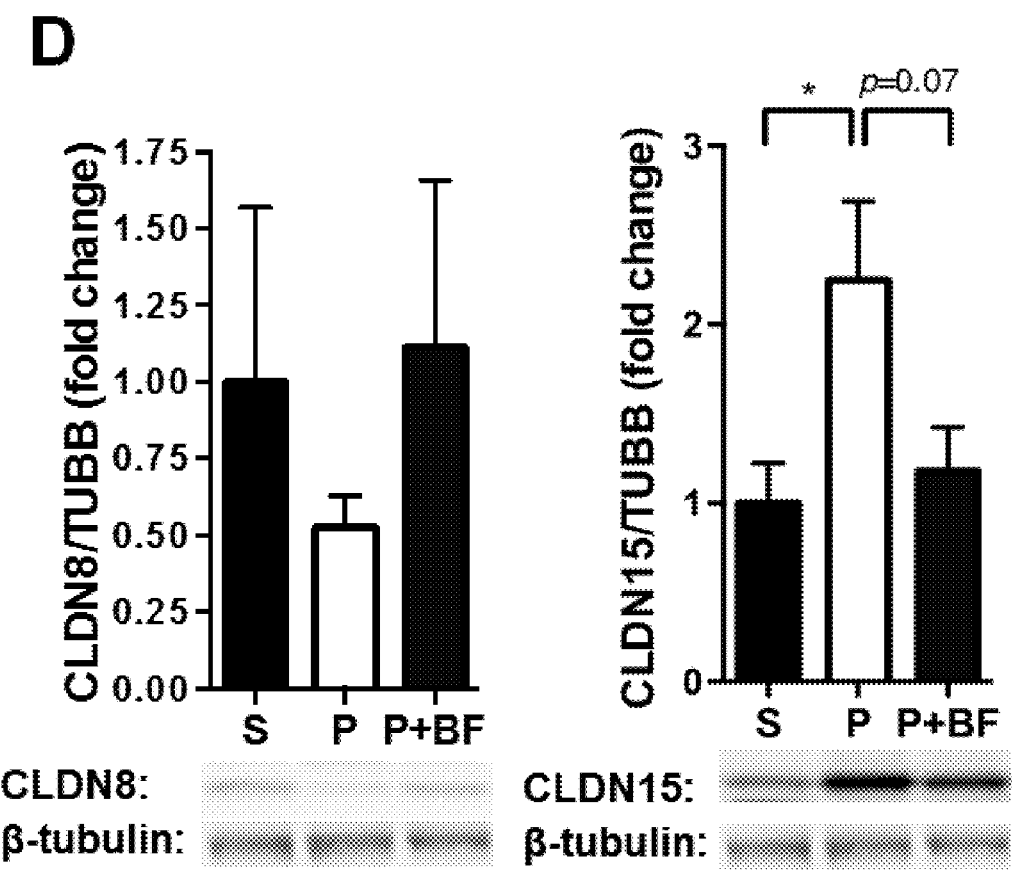
Figure 6:
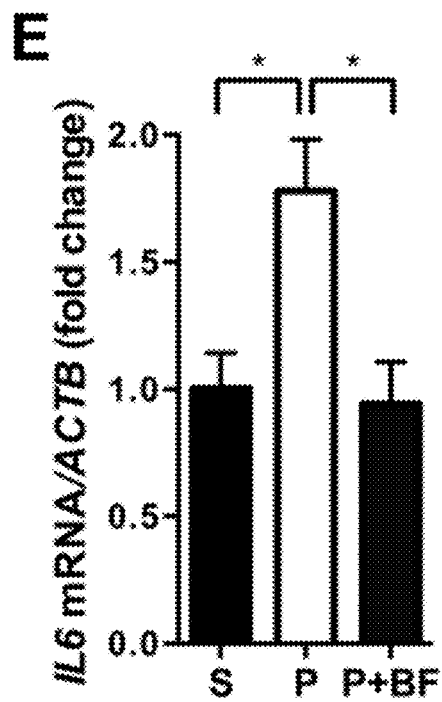
Figure 6:
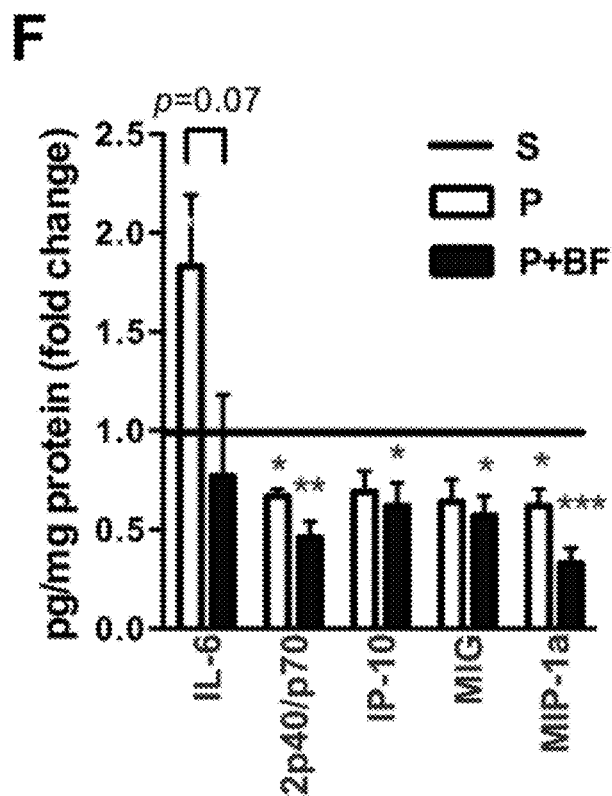

Key OTUs, that discriminate between Saline and Poly(I:C) treatment groups, and between Poly(I:C) and Poly(I:C)+B. fragilis treatment groups, were identified using an unbiased method from OTU tables, generated by QIIME, using three complimentary analyses: (1) Metastats comparison (White et al., 2009), (2) the Random Forests algorithm, first under QIIME (Knights et al., 2011) and subsequently coupled with Boruta feature selection, in the Genboree microbiome toolset (Riehle et al., 2012), and (3) the Galaxy platform-based LDA Effect Size analysis (LEfSe; (Segata et al., 2011)). Only OTUs that differ significantly between treatment groups were candidates for further analyses ($p<0.05$ for (1) and (3), and $>0.0001$ mean decrease in accuracy for Random Forests and subsequent identification by the Boruta algorithm). Metastats analyses were done using the online interface (http://metastats.cbcb.umd.edu) with QIIME-generated OTU tables of any two treatment groups. The Random Forests algorithm was used to identify discriminatory OTUs in the QIIME software package (Breiman, 2001; Knights et al., 2011), comparing two treatment groups at a time, based on 1000 trees and a 10-fold cross-validation, and was further validated and coupled with the Boruta feature selection algorithm, as implemented in the Genboree Microbiome toolset (Kursa and Rudnicki, 2010; Riehle et al., 2012). Only those OTUs that were confirmed by the Boruta algorithm were defined as discriminatory. The ratio between observed and calculated error rates was used as a measure of confidence for Random Forests Analyses: this ratio was 5.0 for saline vs. poly(I:C) (with an estimated error of $0.1\pm0.21$) and 2.86 for poly(I:C) vs. poly(I:C)+B. fragilis (with an estimated error of $0.23\pm0.22$). In order to overcome any mislabeling by any one of the three methods only OTUs that were identified by at least two of the three above methods were defined as discriminatory. For the analyses in FIG. 1, OTUs that were significantly altered by MIA were identified by comparing the saline vs. poly(I:C) groups. For the analyses in FIG. 6, the poly(I:C) vs. poly (I:C)+B. fragilis groups were compared, and only report only those OTUs that have also been identified by the analyses in FIG. 1.

Key OTUs were than aligned using the SINA aligner (http://www.arb-silva.de/aligner/; Pruesse et al., 2012), compared to the SILVA reference database release 111 (Quast et al., 2013) using Arb (Ludwig et al., 2004) and visualized using FigTree (http://tree.bio.ed.ac.uk/software/figtree/). Heat maps of key OTUs were generated by extracting their relative abundance from the OTU table. These data were then normalized (so that the sum of squares of all values in a row or column equals one), first by OTU and subsequently by sample, and clustered by correlation using Cluster 3.0 (de Hoon et al., 2004). Finally, abundance data was visualized using Java TreeView (Saldanha, 2004).

B. fragilis Colonization Assay

Fecal samples were sterilely collected from MIA and control offspring at 1, 2 and 3 weeks after the start of treatment with B. fragilis or vehicle. Germ-free mice were treated with B. fragilis as described above to serve as positive controls. DNA was isolated fecal samples using the QJAamp DNA Stool Mini Kit (Qiagen). 50 ng DNA was used for qPCR with B. fragilis-specific, 5' TGATTCCG-CATGGTTTCATT 3' (SEQ ID NO: 1) and 5' CGAC-CCATAGAGCCTTCATC 3' (SEQ ID NO: 2), and universal 16S primers 5' ACTCCTACGGGAGGCAGCAGT 3' (SEQ ID NO: 3) and 5' ATTACCGCGGCTGCTGGC 3' (SEQ ID NO: 4) according to Odamaki et al., 2008.

Behavioral Testing

Figure 10:
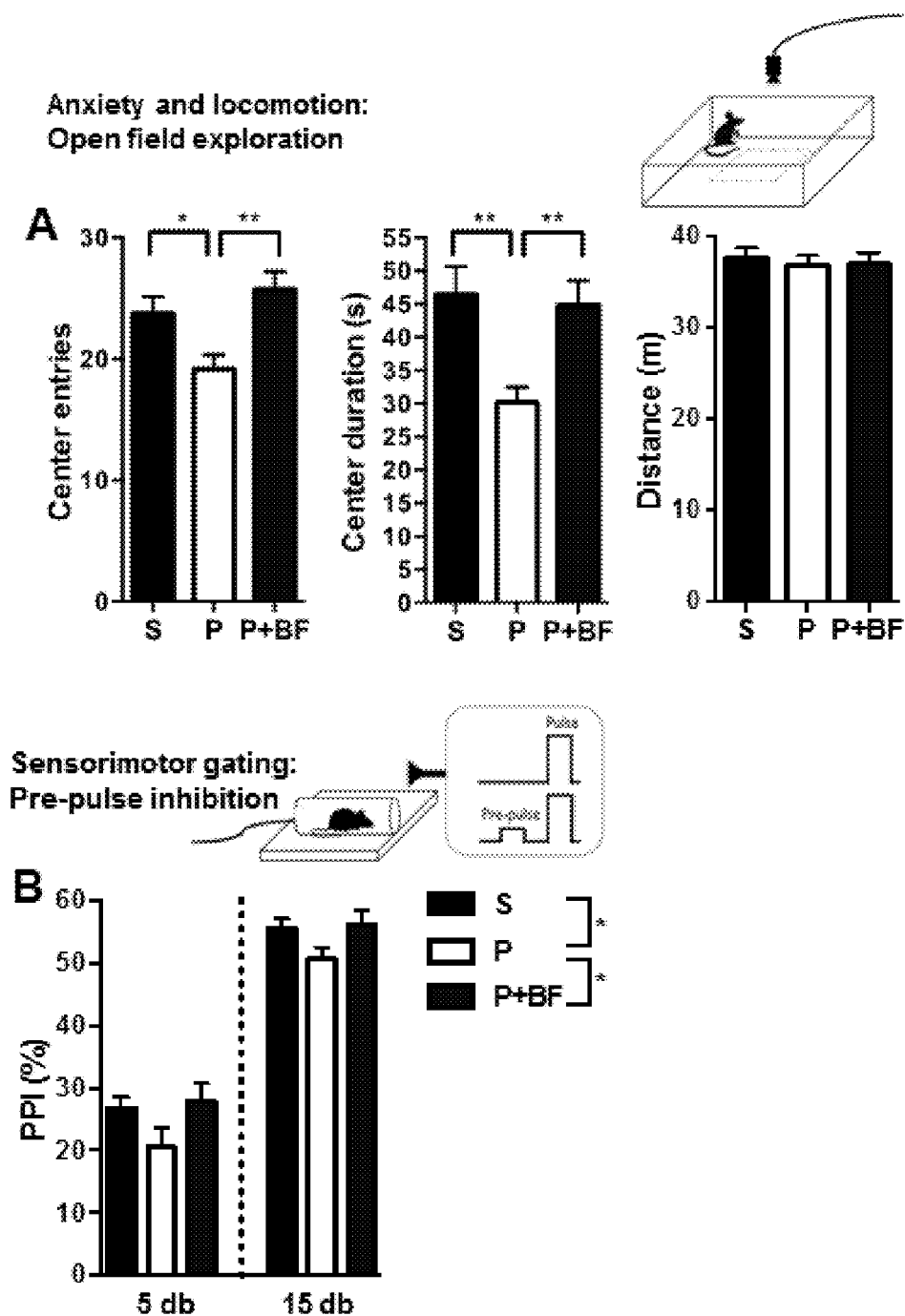
FIG. 10. B. fragilis treatment ameliorates autism-related behavioral abnormalities in MIA offspring.
Figure 10:
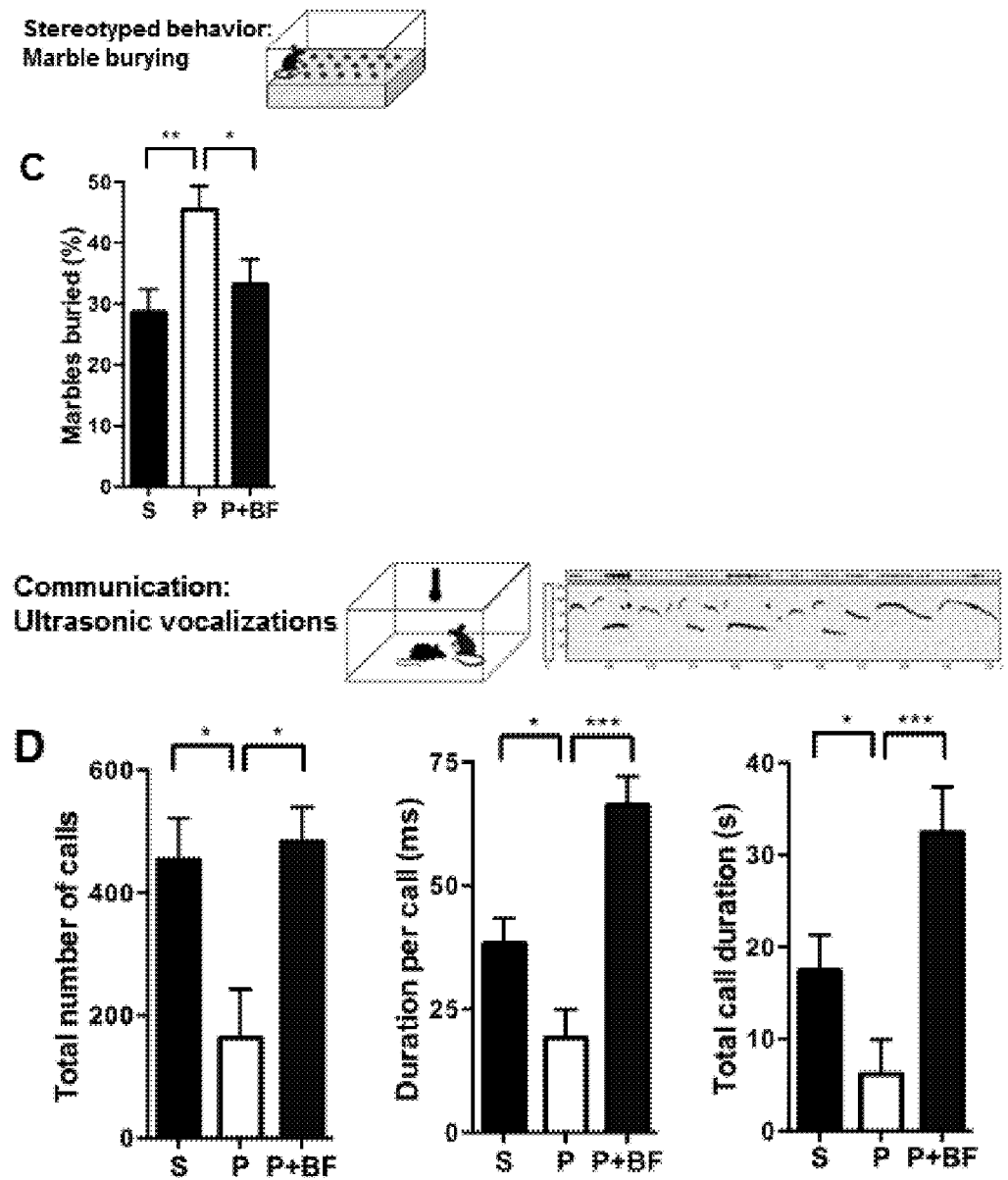
Figure 10:
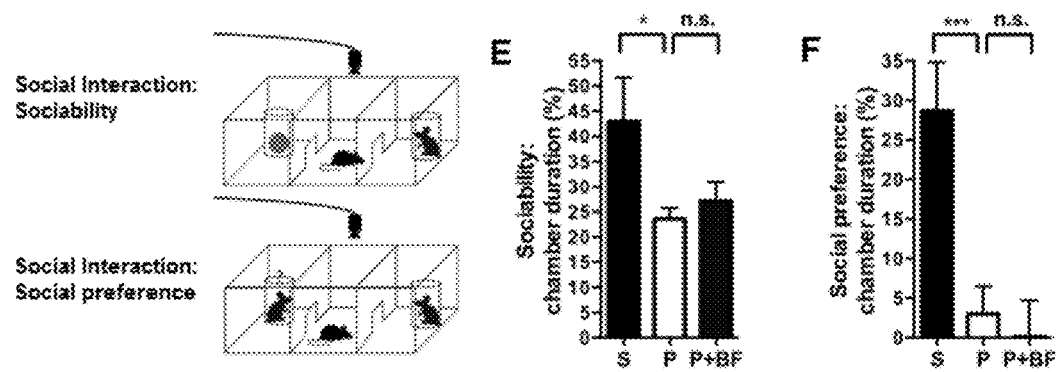
Figure 11:
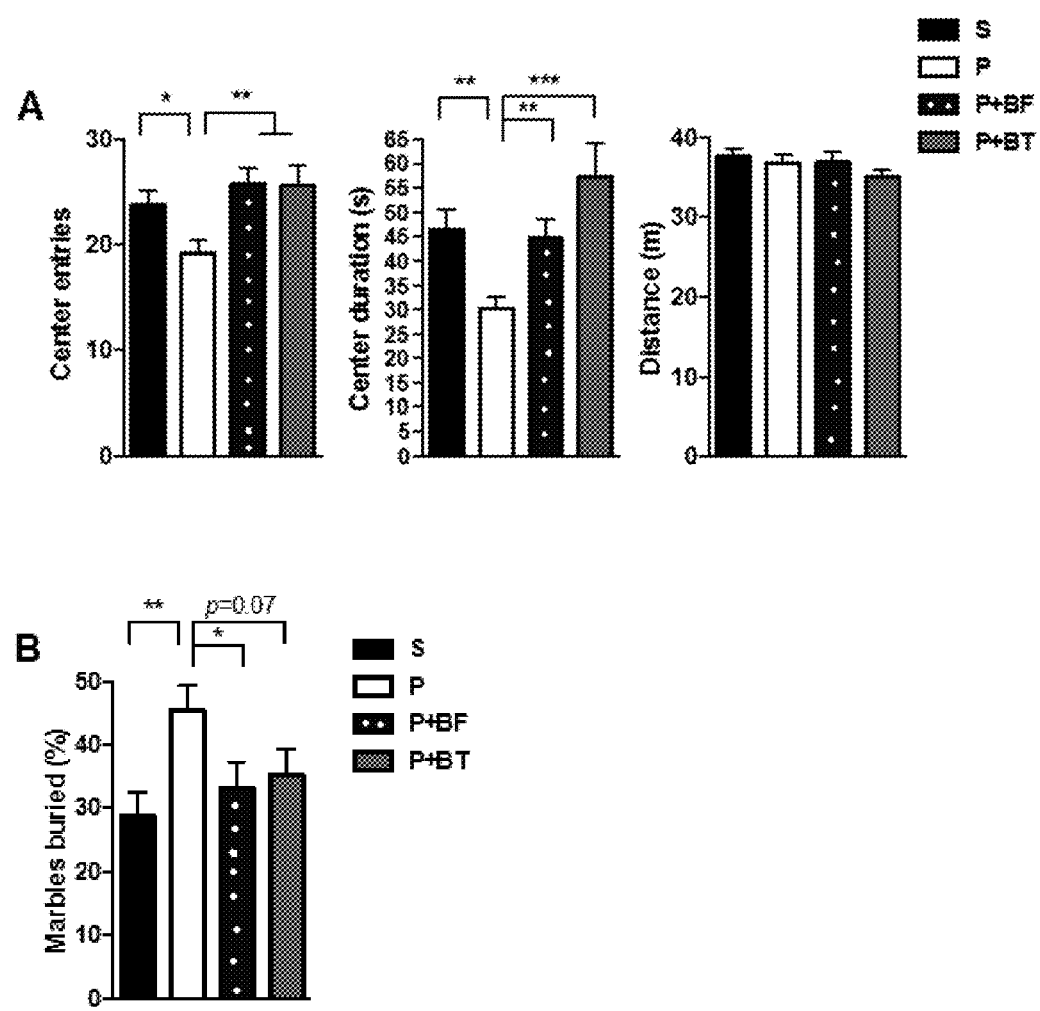
FIG. 11. Amelioration of autism-related behaviors in MIA offspring is not specific to B. fragilis treatment.
Figure 11:
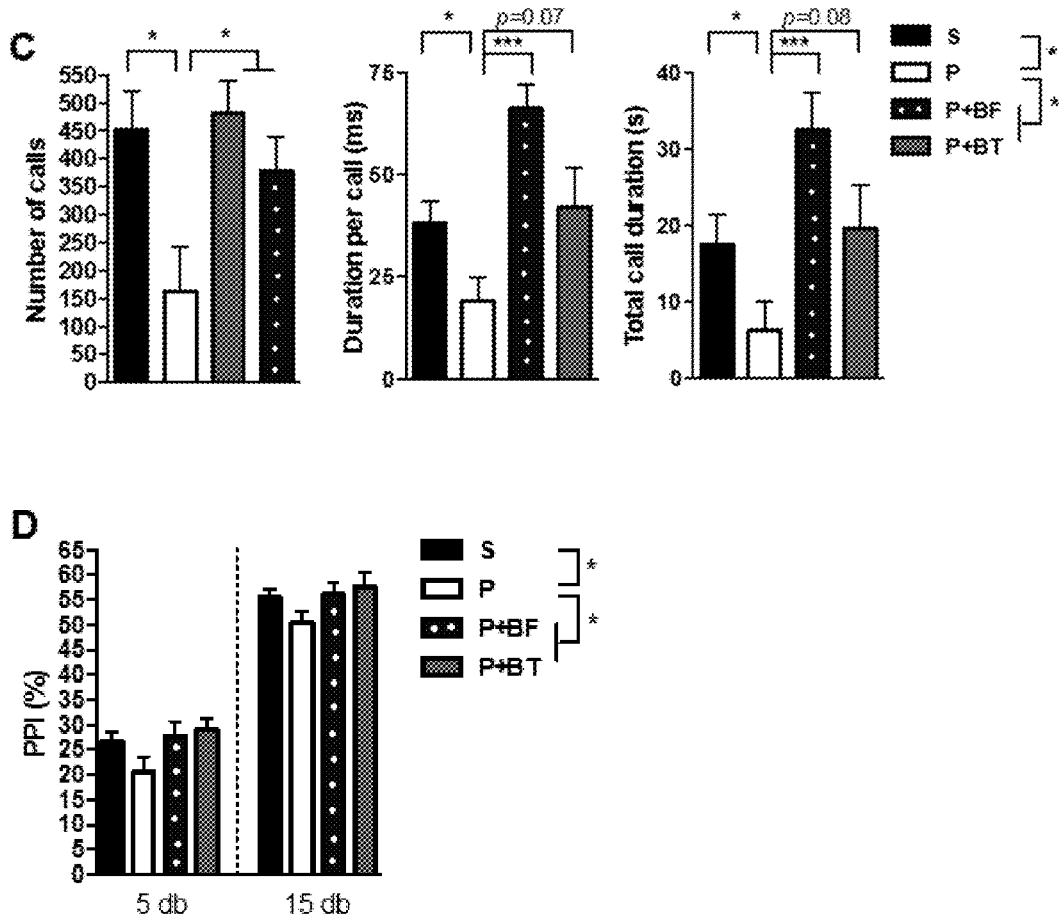

Adult MIA and control offspring were behaviorally tested as described in Hsiao et al., 2012 and Malkova et al., 2012. Mice were tested beginning at 6 weeks of age for pre-pulse inhibition, open field exploration, marble burying, social interaction and adult ultrasonic vocalizations, in that order, with at least 5 days between behavioral tests. Behavioral data for B. fragilis treatment and control groups (FIG. 10) represent cumulative results collected from multiple litters of 3-5 independent cohorts of mice for PPI and open field tests, 2-4 cohorts for marble burying, 2 cohorts for adult male ultrasonic vocalization and 1 cohort for social interaction. Discrepancies in sample size across behavioral tests reflect differences in when during our experimental study a particular test was implemented.

Pre-Pulse Inhibition.

PPI tests are used as a measure of sensorimotor gating and were conducted and analyzed according to the procedure described in Geyer and Swerdlow, 2001 and Smith et al., 2007. Briefly, mice were acclimated to the testing chambers of the SR-LAB startle response system (San Diego Instruments) for 5 minutes, presented with six 120 db pulses of white noise (startle stimulus) and then subjected to 14 randomized blocks of either no startle, startle stimulus only, 5 db prepulse with startle or 15 db prepulse with startle. The startle response was recorded by a pliezo-electric sensor, and the percent PPI is defined as: [((startle stimulus only—5 or 15 db prepulse with startle)/startle stimulus only)*100].

Open Field Exploration.

The open field test is widely used to measure anxiety-like and locomotor behavior in rodents. Mice were placed in 50×50 cm white Plexiglas boxes for 10 minutes. An overhead video camera recorded the session, and Ethovision software (Noldus) was used to analyze the distance traveled, and the number of entries and duration of time spent in the center arena (central 17 cm square).

Marble Burying.

Marble burying is an elicited repetitive behavior in rodents analogous to those observed in autistic individuals (Silverman et al., 2010b). This test was conducted and analyzed according to methods described in Thomas et al., 2009 and Malkova et al., 2012. Mice were habituated for 10 minutes to a novel testing cage containing a 4 cm layer of chipped cedar wood bedding and then transferred to a new housing cage. 18 glass marbles (15 mm diameter) were aligned equidistantly 6×3 in the testing cage. Mice were returned to the testing cage and the number of marbles buried in 10 minutes was recorded.

Sociability and Social Preference.

Social interaction tests were conducted and analyzed according to methods adopted from Sankoorikal et al., 2006 and Yang et al., 2011. Briefly, testing mice were habituated for 10 minutes to a 40×60 cm Plexiglas three-chambered apparatus containing clear interaction cylinders in each of the side chambers. Sociability was tested in the following 10 minute session, where the testing mouse was given the opportunity to explore a novel same-sex, age-matched mouse in one interaction cylinder (social object) versus a novel toy (green sticky ball) in the other interaction cylinder of the opposite chamber. Social preference was tested in the final 10 minute session, where the testing mouse was given the opportunity to explore a now familiar mouse (stimulus mouse from the previous sociability session) versus a novel unfamiliar same-sex, age-matched mouse. In each session, the trajectory of the testing mouse was tracked with Ethovision software (Noldus). Sociability data is presented as preference for the mouse over the toy: percent of time in the social chamber—percent of time in the nonsocial chamber, and social preference data is presented as preference for the unfamiliar mouse over the familiar mouse: percent of time in the unfamiliar mouse chamber—percent of time in the familiar mouse chamber. Similar indexes were measured for chamber entries, and entries into and duration spent in the contact zone (7×7 cm square surrounding the interaction cylinder).

Adult Ultrasonic Vocalizations.

Male mice produce USVs in response to female mice as an important form of communication (Portfors, 2007). Adult male USV production in response to novel female exposure was measured according to methods described in Grimsley et al., 2011; Scattoni et al., 2011; and Silverman et al., 2010a. Adult males were single-housed one week before testing and exposed for 20 minutes to an unfamiliar adult female mouse each day starting four days prior to testing in order to provide a standardized history of sexual experience and to adjust for differences in social dominance. On testing day, mice were habituated to a novel cage for 10 minutes before exposure to a novel age-matched female. USVs were recorded for 3 minutes using the UltraSoundGate microphone and audio system (Avisoft Bioacoustics). Recordings were analyzed using Avisoft's SASLab Pro software after fast Fourier transformation at 512 FFT-length and detection by a threshold-based algorithm with 5 ms hold time. Data presented reflect duration and number of calls produced in the 3 minute session.

Metabolomics Screening

Sera were collected by cardiac puncture from behaviorally validated adult mice. Samples were extracted and analyzed on GC/MS, LC/MS and LC/MS/MS platforms by Metabolon, Inc. Protein fractions were removed by serial extractions with organic aqueous solvents, concentrated using a TurboVap system (Zymark) and vacuum dried. For LC/MS and LC/MS/MS, samples were reconstituted in acidic or basic LC-compatible solvents containing >11 injection standards and run on a Waters ACQUITY UPLC and Thermo-Finnigan LTQ mass spectrometer, with a linear ion-trap front-end and a Fourier transform ion cyclotron resonance mass spectrometer back-end. For GC/MS, samples were derivatized under dried nitrogen using bistrimethyl-silyl-trifluoroacetamide and analyzed on a Thermo-Finnigan Trace DSQ fast-scanning single-quadrupole mass spectrometer using electron impact ionization. Chemical entities were identified by comparison to metabolomic library entries of purified standards. Following log transformation and imputation with minimum observed values for each compound, data were analyzed using two-way ANOVA with contrasts.

4EPS Synthesis and Detection

Figure 15A:
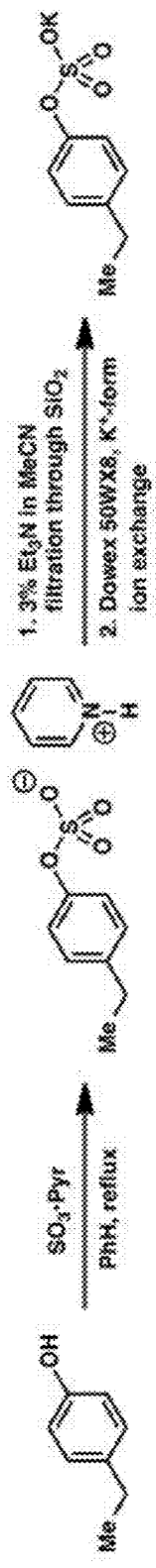
FIGS. 15A-E. 4-ethylphenylsulfate (4EPS) synthesis, detection and in vivo experiments.

Potassium 4-ethylphenylsulfate was prepared using a modification of a procedure reported for the synthesis of aryl sulfates in Burlingham et al., 2003 and Grimes, 1959 (FIG. 15A). 4-ethylphenol (Sigma-Aldrich, 5.00 g, 40.9 mmol) was treated with sulfur trioxide-pyridine complex (Sigma-Aldrich, 5.92 g, 37.2 mmol) in refluxing benzene (20 ml, dried by passing through an activated alumina column). After 3.5 hours, the resulting solution was cooled to room temperature, at which point the product crystallized. Isolation by filtration afforded 7.93 g of crude pyridinium 4-ethylphenylsulfate as a white crystalline solid. 1.00 g of this material was dissolved in 10 mL of 3% triethylamine in acetonitrile and filtered through a plug of silica gel (Silicycle, particle size 32-63 µm), eluting with 3% triethylamine in acetonitrile. The filtrate was then concentrated, and the resulting residue was dissolved in 20 mL of deionized water and eluted through a column of Dowex 50WX8 ion exchange resin ($K^+$ form), rinsing with 20 mL of deionized water. The ion exchange process was repeated once more, and the resulting solution concentrated under vacuum to afford 618 mg (55% overall yield) of potassium 4-ethylphenylsulfate as a white powder (FIG. 15A).

$^1H$ and $^{13}C$ NMR spectra of authentic potassium 4-ethylphenylsulfate were recorded on a Varian Inova 500 spectrometer and are reported relative to internal DMSO-$d_5$ ($^1H$, δ=2.50; $^{13}C$, δ=39.52). A high-resolution mass spectrum (HRMS) was acquired using an Agilent 6200 Series TOF with an Agilent G1978A Multimode source in mixed ionization mode (electrospray ionization (ESI) and atmospheric pressure chemical ionization (APCI)). Spectroscopic data for potassium 4-ethylphenylsulfate are as follows: $^1H$ NMR (DMSO-$d_6$, 500 MHz) δ 7.11-7.04 (m, 4H), 2.54 (q, J=7.6 Hz, 2H), 1.15 (t, J=7.6 Hz, 3H); $^{13}C$ NMR (DMSO-$d_6$, 126 MHz) δ 151.4, 138.3, 127.9, 120.6, 27.5, 16.0; HRMS (Multimode-ESI/APCI) calculated for $C_8H_9O_4S$ [M−K]$^-$ 201.0227, found 201.0225.

Figure 15B:
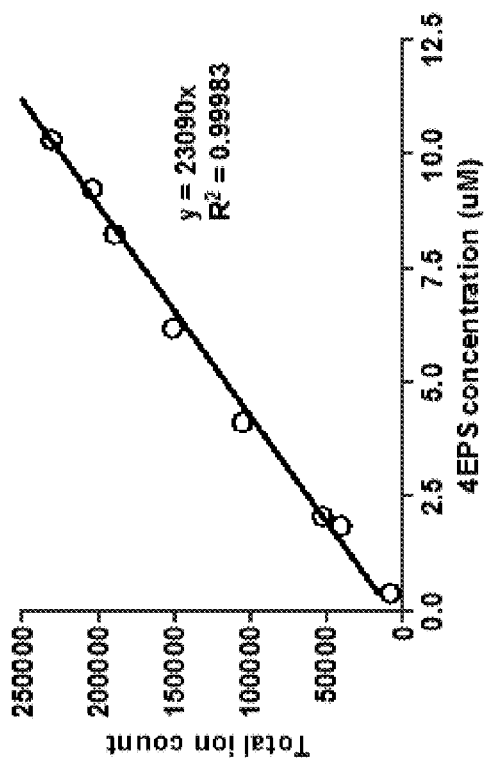

Authentic 4EPS and serum samples were analyzed by LC/MS using an Agilent 110 Series HPLC system equipped with a photodiode array detector and interfaced to a model G1946C single quadrupole expectospray mass spectrometer. HPLC separations were obtained at 25° C. using an Agilent Zorbax XDB-C18 column (4.6 mm×50 mm×5 um particle size). The 4EPS ion was detected using selected ion monitoring for ions of m/z 200.9 and dwell time of 580 ms/ion, with the electrospray capillary set at 3 kV. Authentic potassium 4EPS was found to possess a retention time of 6.2 minutes when eluted in 0.05% trifluoroacetic acid and acetonitrile, using a 10-minute linear gradient from 0-50% acetonitrile. For quantification of 4EPS in mouse sera, a dose-response curve was constructed by plotting the total ion count peak area for known concentrations of authentic potassium 4EPS against the analyte concentration ($R^2$=0.9998; FIG. 15B). Mouse serum samples were diluted four-fold with acetonitrile and centrifuged at 10,000 g at 4° C. for 3 minutes. 10 ul of supernatant was injected directly into the HPLC system.

4EPS Sufficiency Experiments

Figure 15C:
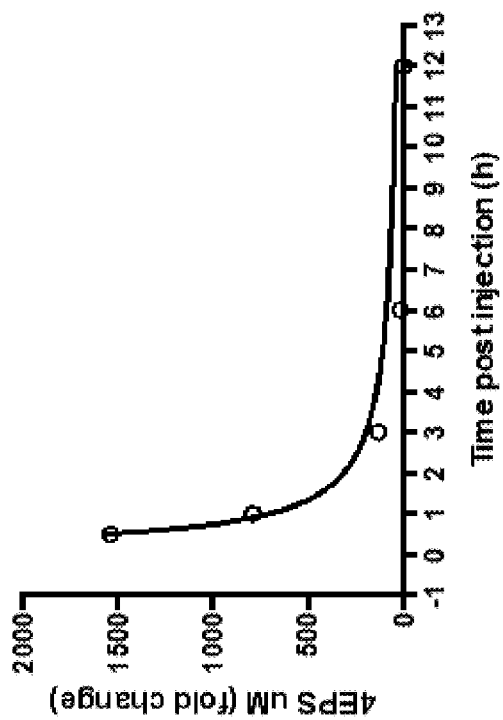

Wildtype mice were injected i.p. with saline or 30 mg/kg 4EPS potassium salt daily from 3 to 6 weeks of age. A dose-response curve was generated by measuring serum 4EPS levels at various times after i.p. injection of 30 mg/kg 4EPS (FIG. 15C). Mice were behaviorally tested as described above from 6 to 9 weeks of age.

Statistical Analysis

Statistical analysis was performed using Prism software (Graphpad). Data were assessed for normal distribution and plotted in the figures as mean±SEM. Differences between two treatment groups (i.e. control versus 4EPS) were assessed using two-tailed, unpaired Student t test with Welch's correction. Differences among multiple groups (saline versus poly(I:C) versus poly(I:C)+*B. fragilis/B. thetaiotaomicron*) were assessed using one-way ANOVA with Bonferroni post hoc test. Two-way repeated measures ANOVA with Bonferroni post hoc test was used for analysis of PPI and CD4+ T-cell stimulation data. Two-way ANOVA with contrasts was used for analysis of the metabolite data. Sample sizes denote the number of individual mice per treatment group, given the individual randomization design of the study (Lazic, 2013). Significant differences emerging from the above tests are indicated in the figures by *$p<0.05$, $p<0.01$, *$p<0.001$. Notable near-significant differences ($0.5<p<0.1$) are indicated in the figures. Notable non-significant (and non-near significant) differences are indicated in the figures by "n.s.".

Example 1

Offspring of Immune-Activated Mothers Exhibit GI Symptoms of Human ASD

Adult MIA offspring, which exhibit cardinal behavioral and neuropathological symptoms of ASD (Malkova et al., 2012), were also found to display a significant deficit in intestinal barrier integrity, as reflected by increased translocation of orally administered FITC-dextran across the intestinal epithelial layer and into the circulation (FIG. 1A, left panel). This MIA-associated increase in intestinal permeability is similar to what's seen in mice treated with dextran sodium sulfate (DSS), a chemical used to induce experimental colitis (FIG. 1A, left panel) (Wirtz et al., 2007). Deficits in intestinal integrity were detectable in 3-week-old MIA offspring (FIG. 1A, right panel), indicating that the abnormality was established during early life. To assess the molecular basis for increased intestinal permeability in MIA offspring, colons of MIA offspring were examined for the tight junction components ZO-1 (TJP1), ZO-2 (TJP2), ZO-3 (TJP3), occludin and claudins (CLDN) 1, 2, 3, 4, 7, 8, 12, 13 and 15 (Holmes et al., 2006). Consistent with the leaky gut phenotype found in subsets of ASD children displaying GI abnormalities, colons from adult MIA offspring exhibited decreased expression of transcripts for ZO-1, ZO-2, occludin and claudin 8, and increased expression of claudin 15 mRNA (FIG. 1B). Deficient expression of ZO-1 is also observed in small intestines of adult MIA offspring (FIG. 2A), demonstrating a widespread defect in intestinal barrier integrity.

Figure 2:
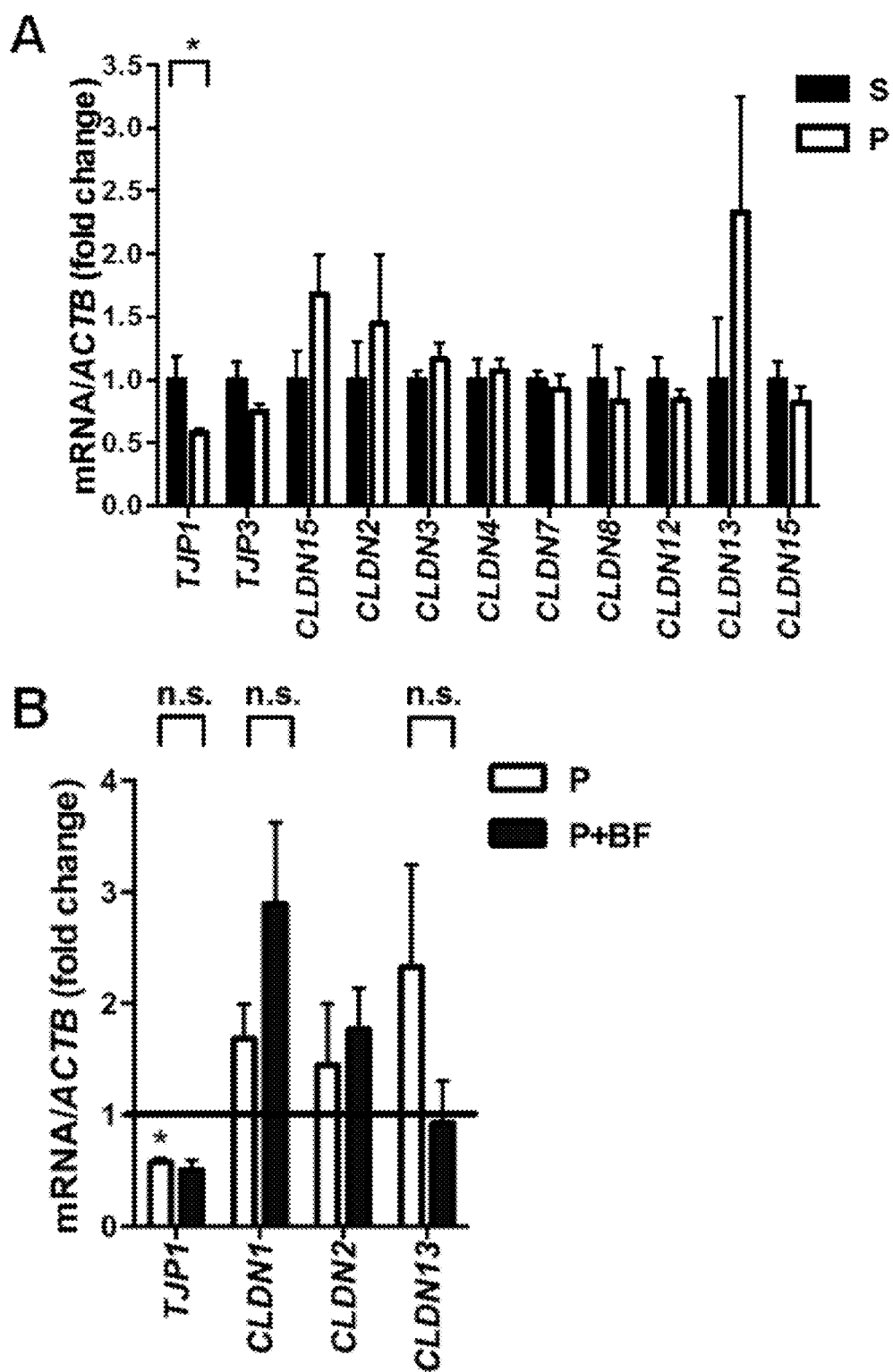
FIG. 2. *B. fragilis* treatment has little effect on tight junction expression and cytokine profiles in the small intestine.
Figure 2:
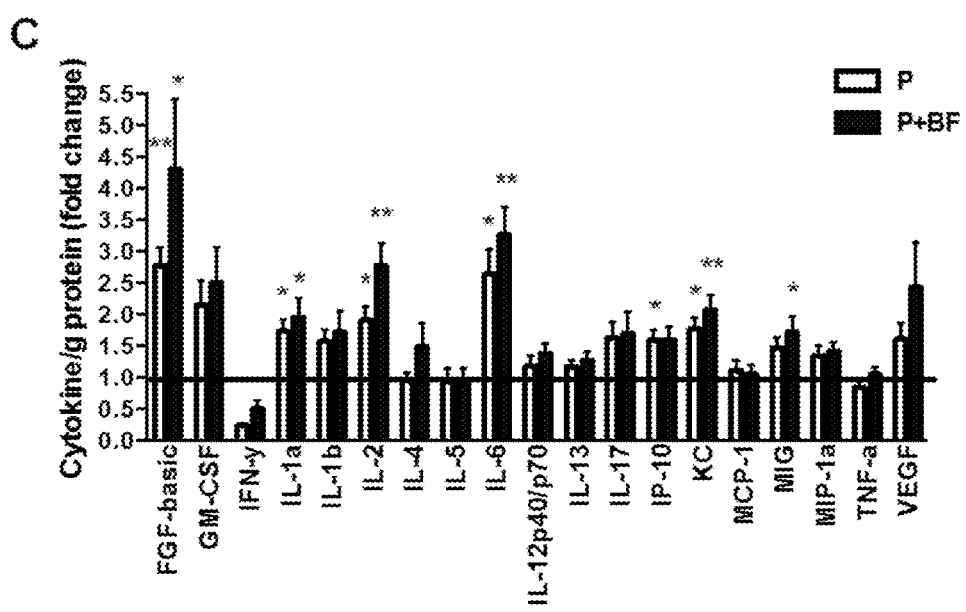
Figure 3:
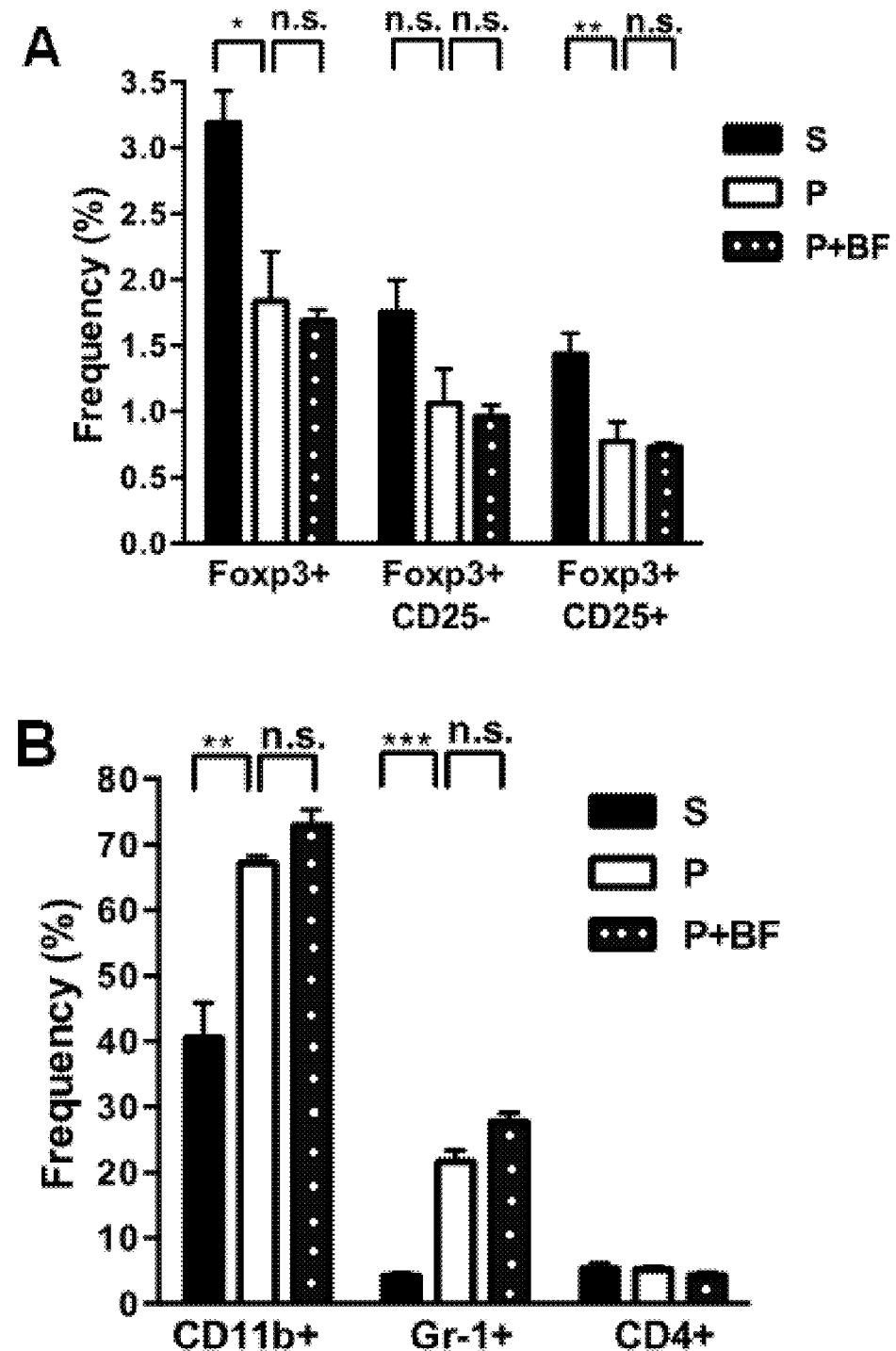
FIG. 3. *B. fragilis* treatment has no effect on systemic immune dysfunction in MIA offspring.
Figure 3:
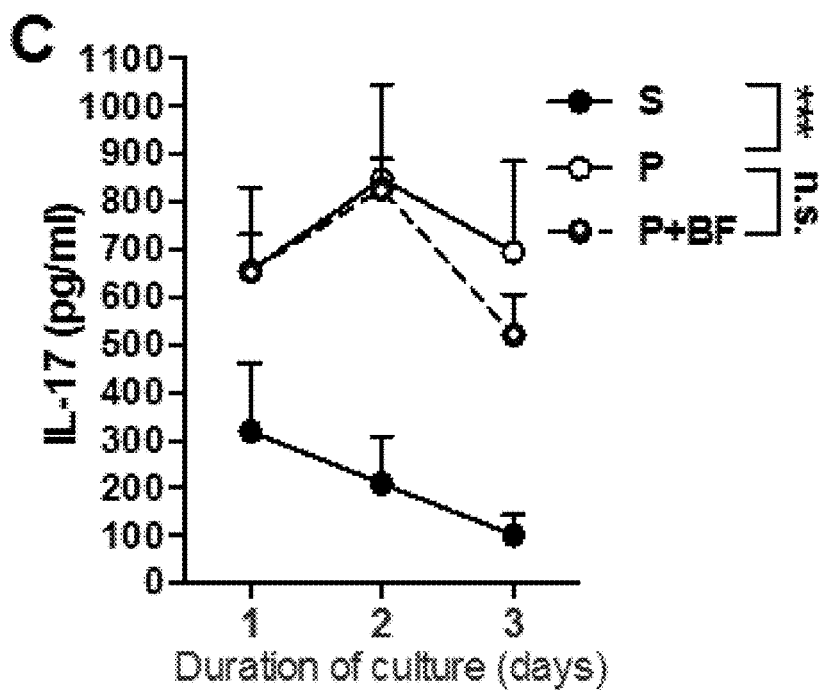
Figure 3:
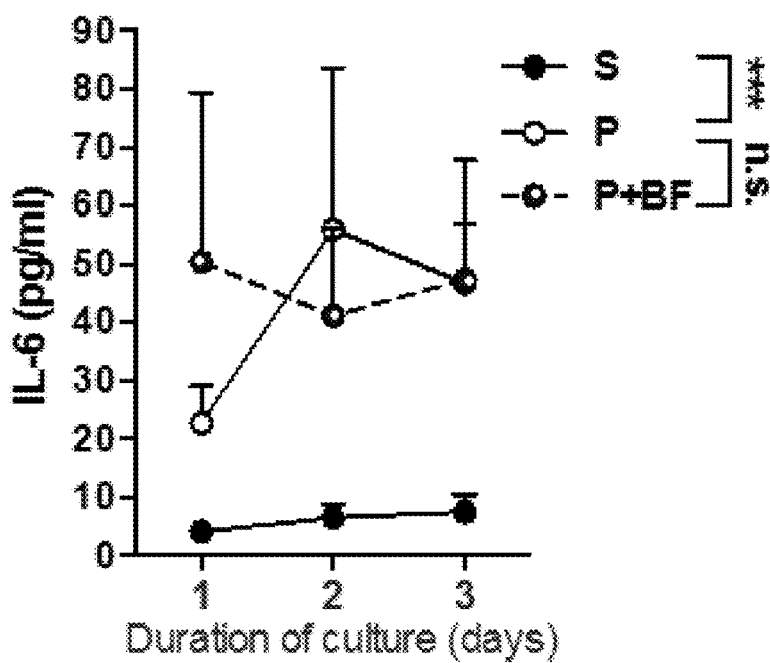
Figure 3:
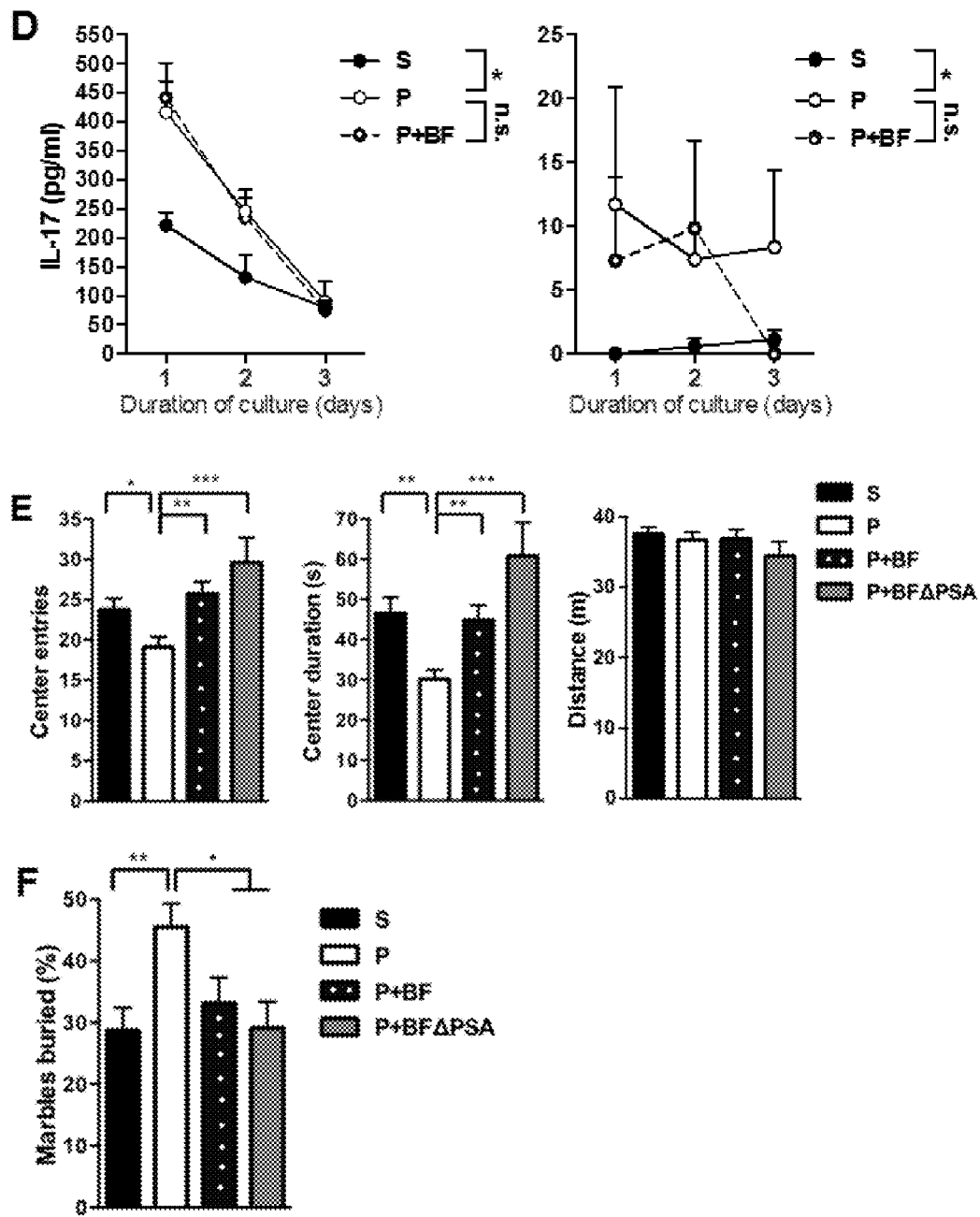

Increased permeability is observed in several intestinal diseases, as well as subsets of ASD, and is commonly associated with signs of inflammation (Hering et al., 2012; Turner, 2009; White, 2003). In addition to changes in expression of tight junction components, colons from adult MIA offspring were found to display increased levels of interleukin-6 (IL-6) mRNA and protein (FIGS. 1C and 1D) and decreased levels of the cytokines/chemokines IL-12p40/p70, IP-10, MIG and MIP-1a (FIG. 1D). Small intestines from MIA offspring also exhibit altered cytokine/chemokine profiles (FIG. 2C). Changes in intestinal cytokines were not accompanied by overt GI pathology, as assessed by histological examination of gross epithelial morphology from hematoxylin- and eosin-stained sections. Consistent with the alterations in immune-related signaling factors, however, mesenteric lymph nodes and spleens from adult MIA offspring were found to contain decreased levels of regulatory T cells and hyper-responsive production of IL-6 and IL-17 by CD4+ T helper cells, suggestive of a pro-inflammatory phenotype (FIG. 3A-D) (Hsiao et al., 2012). Similar findings supporting enteric immune activation are seen in subsets of ASD individuals (Onore et al., 2012).

In view of the foregoing, this examples shows that adult offspring of immune-activated mothers exhibit increased gut permeability and abnormal intestinal cytokine profiles, recapitulating ASD-related GI symptoms in a mouse model.

Example 2

MIA Offspring Display Dysbiosis of the Gut Microbiota

The potential link between disruption of the normal gut microbiota and GI dysfunction in an ASD mouse model was examined in this example.

Figure 4:
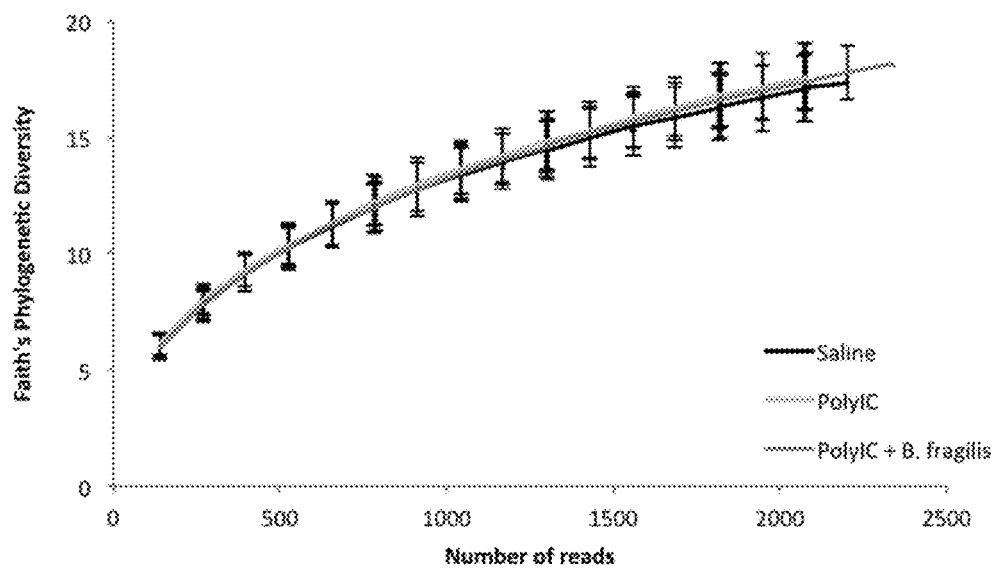
FIG. 4. MIA induces alterations in the composition of the intestinal microbiota.
Figure 4:
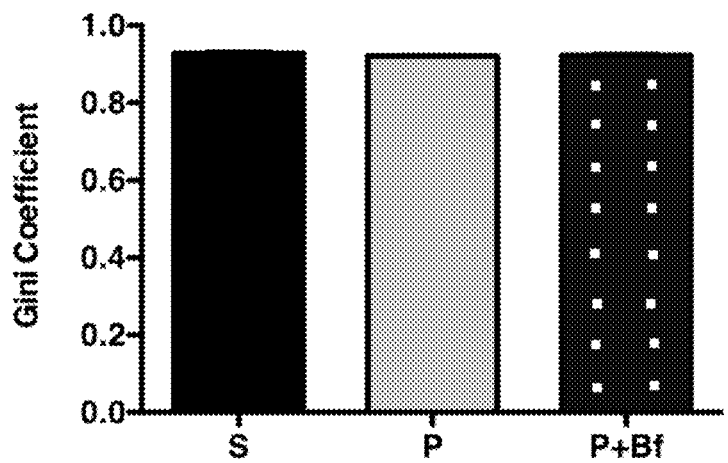
Figure 4:
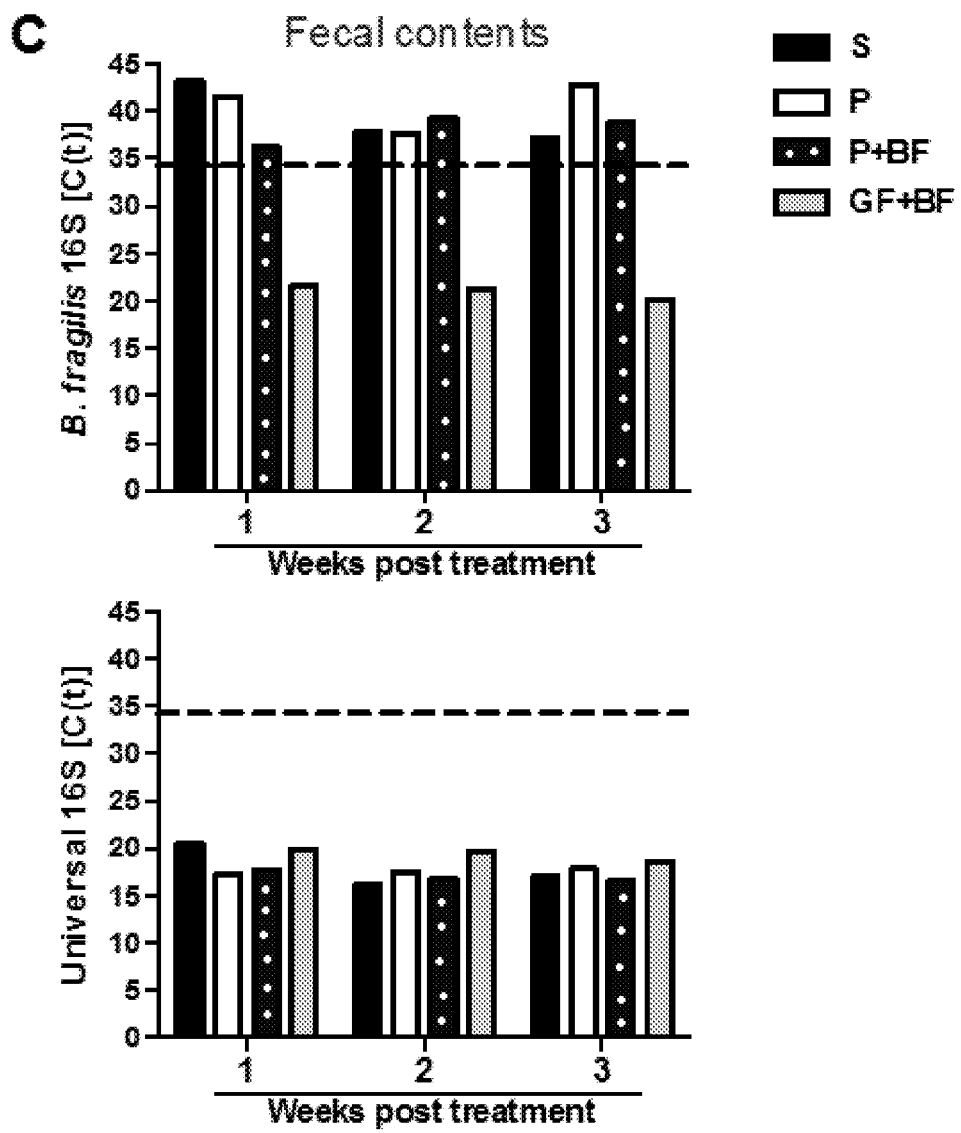
Figure 4:
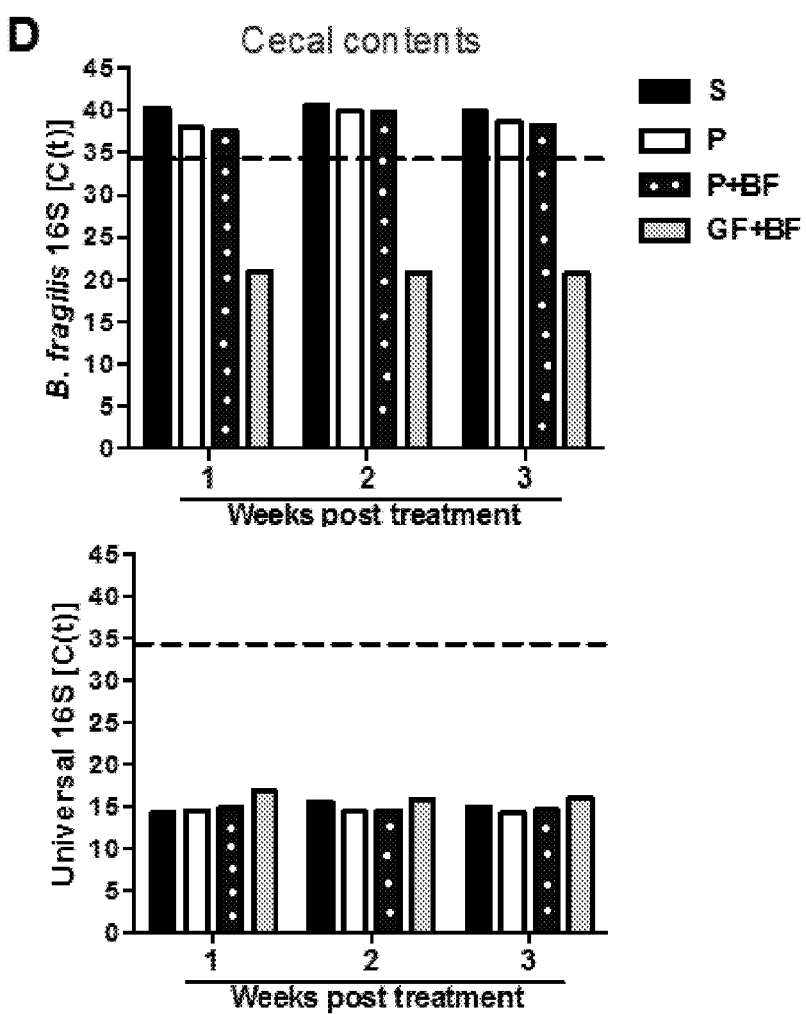
Figure 5A:
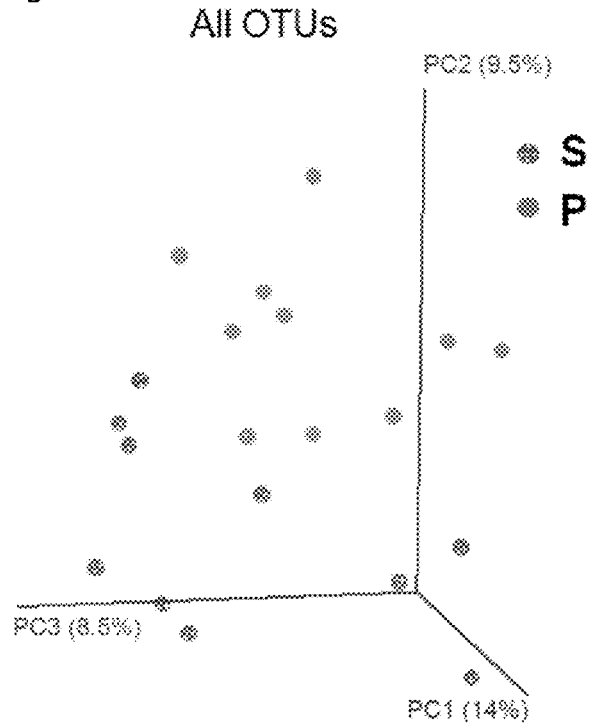
FIGS. 5A-E. MIA offspring exhibit dysbiosis of the intestinal microbiota.
Figure 5B:
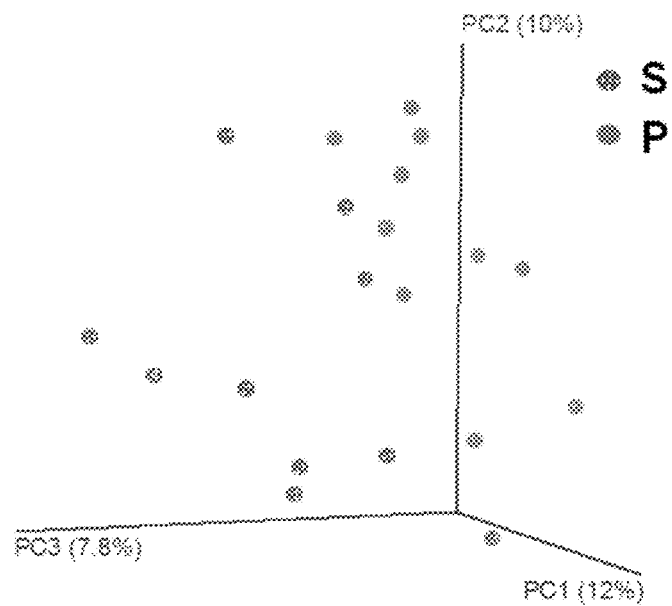
Figure 5C:
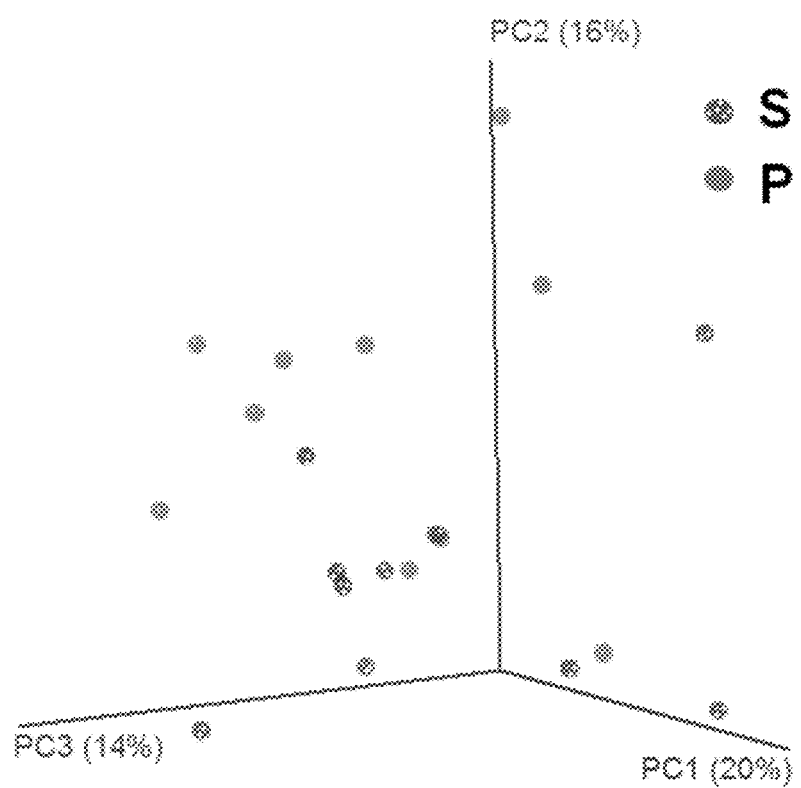

To evaluate whether MIA induces microbiota alterations, the fecal bacterial population was surveyed by 16S rRNA gene sequencing of samples isolated from adult offspring of mothers treated with poly(I:C) or saline. Alpha diversity, i.e., species richness and evenness, did not differ significantly between control and MIA offspring, as measured by Faith's phylogenetic diversity (PD) index, and number of Observed Species (p=1.0000 and 0.2790, respectively) and the Gini coefficient and Simpson evenness index (p=0.5430 and p=0.2610, respectively; FIGS. 4A and 4B). In contrast, unweighted UniFrac analysis, which measures the degree of phylogenetic similarity between microbial communities, reveals a strong effect of MIA on the gut microbiota of adult offspring (FIG. 5A-E). MIA samples cluster distinctly from controls by principal coordinate analysis (PCoA; ANOSIM R=0.2829, p=0.0030), indicating robust changes in the membership of gut bacteria from MIA offspring compared to controls (FIG. 5A). The effect of MIA on altering the composition of the gut microbiota is further evident when sequences from the classes Clostridia and Bacteroidia, which account for approximately 90.1% of the total reads in our survey (46,484 reads out of 51,586 in the S and P groups), were exclusively examined by PCoA (R=0.2331, p=0.0070; FIG. 5B), but not when Clostridia and Bacteroidia sequences were specifically excluded from PCoA of all other bacterial classes (R=0.1051, p=0.0700; FIG. 5C). This indicates that changes in the diversity of Clostridia and Bacteroidia operational taxonomic units (OTUs) are the primary drivers of gut microbiota differences between MIA offspring and controls.

Figure 5D:
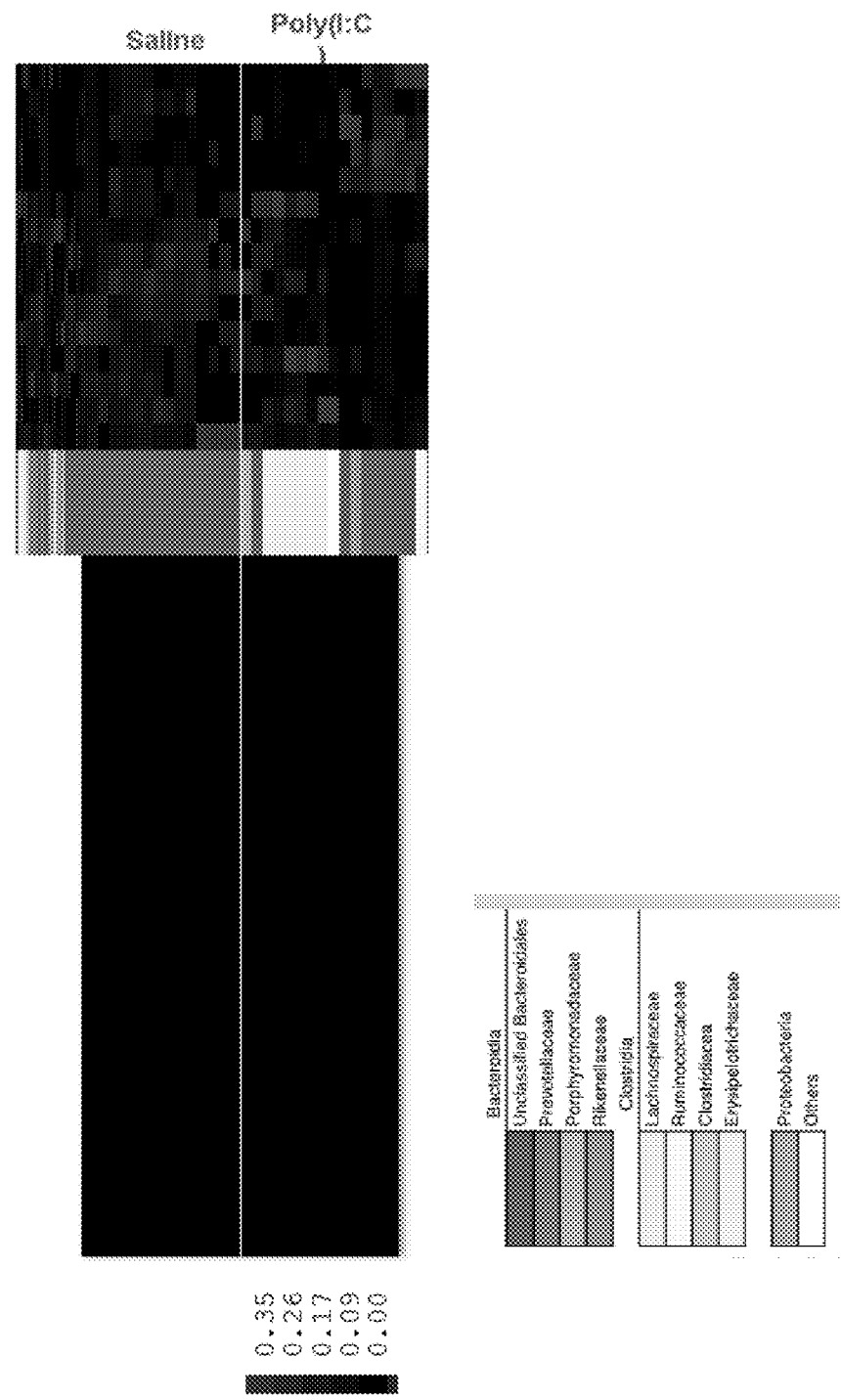

67 OTUs out of the 1474 OTUs detected across any of the samples discriminate between treatment groups, including those assigned to the bacterial families Lachnospiraceae, Ruminococcaceae, Erysipelotrichaceae, Alcaligenaceae, Porphyromonadaceae, Prevotellaceae, and Rikenellaceae, and unclassified Bacteroidales (FIG. 5D). Of these 67 discriminatory OTUs, 19 are more abundant in control samples and 48 are more abundant in MIA samples. Consistent with the PCoA results (FIGS. 5A-C), the majority of OTUs that discriminate MIA offspring from controls are assigned to the classes Bacteroidia (45 of 67 OTUs; 67.2%) and Clostridia (17 of 67 OTUs; 25.4%), whereas the few remaining discriminatory OTUs belong to Proteobacteria (3 OTUs; 4.5%) and other classes (Tenericutes and unclassified, 1 OTU each; 3.0%). Interestingly, Porphyromonadaceae, Prevotellaceae, and many unclassified Bacteriodales (36 of the 45 discriminatory Bacteroidial OTUS; 80%), and Lachnospiriceae (8 of the 14 discriminatory Clostridial OTUs; 57%) were more abundant in MIA offspring. Conversely, Ruminococcaceae (2 OTUs), Erysipelotrichaceae (2 OTUs), and the beta Proteobacteria family Alcaligenaceae (2 OTUs) were more abundant in control offspring (FIG. 5D). These data indicate that specific Lachnospiraceae, along with other Bacteroidial species, play an important role in MIA pathogenesis, while other taxa may have a protective role. Importantly, there is no significant difference in the overall relative abundance of Clostridia (13.63±2.54% vs 14.44±2.84% mean±SEM; Student's t-test p=0.8340) and Bacteroidia (76.25±3.22% vs 76.22±3.46% mean±SEM; Student's t-test p=0.9943) between MIA offspring and controls (FIG. 5E, left panel), indicating that alterations in the membership of rare OTUs drive major changes in the gut microbiota between experimental groups.

Figure 5E:
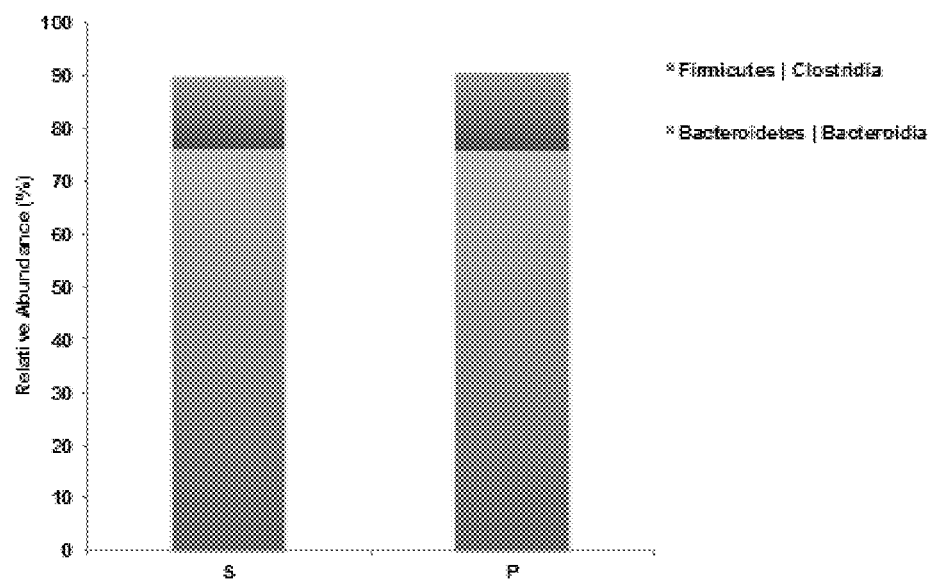
Figure 5E:
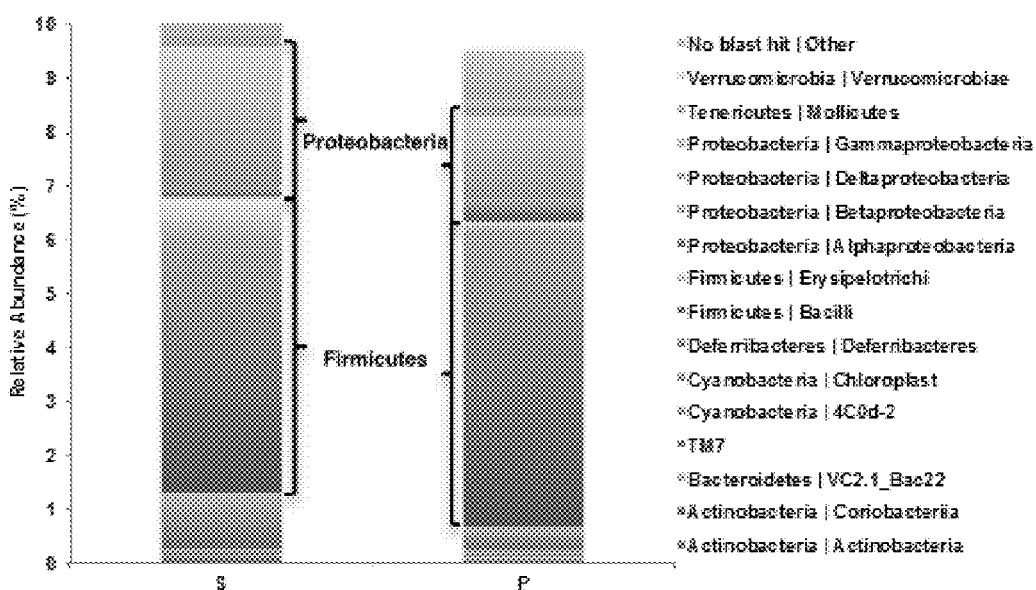

Differences in taxonomic diversity was also seen in less prominent bacterial classes, with MIA offspring displaying significantly decreased relative abundance of Erysipelotrichi (0.15±0.03% v.s. 0.74±0.25% mean±SEM; Student's t-test p-value=0.0334) compared to controls (FIG. 5E, right panel). Overall, MIA was found to lead to dysbiosis of the gut microbiota, driven primarily by alterations in specific OTUs of the bacterial classes Clostridia and Bacteroidia. Changes in OTUs classified as Lachnospiraceae and Ruminococcaceae of the order Clostridiales parallel reports of increased *Clostridium* species in the feces of subjects with ASD (Finegold et al., 2012). Altogether, modeling MIA as a primary autism risk factor in mice induces not only behavioral and neuropathological features of ASD (Boksa, 2010), but also GI symptoms analogous to those described in subsets of ASD individuals. The data presented herein shows that MIA can be used as a model for human ASD with comorbid GI issues.

Example 3

*B. fragilis* Treatment Improves Gut Barrier Integrity in MIA Offspring

Gut microbes play an important role in the development, maintenance and repair of the intestinal epithelium (Sharma et al., 2010; Turner, 2009). To determine whether targeting the gut microbiota could impact the development or persistence of MIA-associated GI abnormalities, offspring was treated with the human commensal bacterium *B. fragilis* at weaning, and then tested for GI abnormalities at 8 weeks of age. Remarkably, *B. fragilis* treatment corrected intestinal permeability in MIA offspring (FIG. 6A). In addition, *B. fragilis* treatment ameliorated MIA-associated changes in gene expression of CLDNs 8 and 15, but had no significant effect on expression levels of TJP1, TJP2 or OCLN mRNA (FIG. 6B). Similar changes are observed in protein levels of claudin 8 and 15 in the colon, with restoration by *B. fragilis* treatment (FIGS. 6C-D). No such effects of *B. fragilis* on tight junction expression are observed in small intestines from MIA offspring (FIG. 2B), consistent with the fact that *Bacteroides* species are predominantly found in the colon. Also, the presence of GI defects prior to probiotic administration (FIG. 1A, right panel) suggests that *B. fragilis* can treat ASD-related pathology in MIA offspring.

Figure 7:
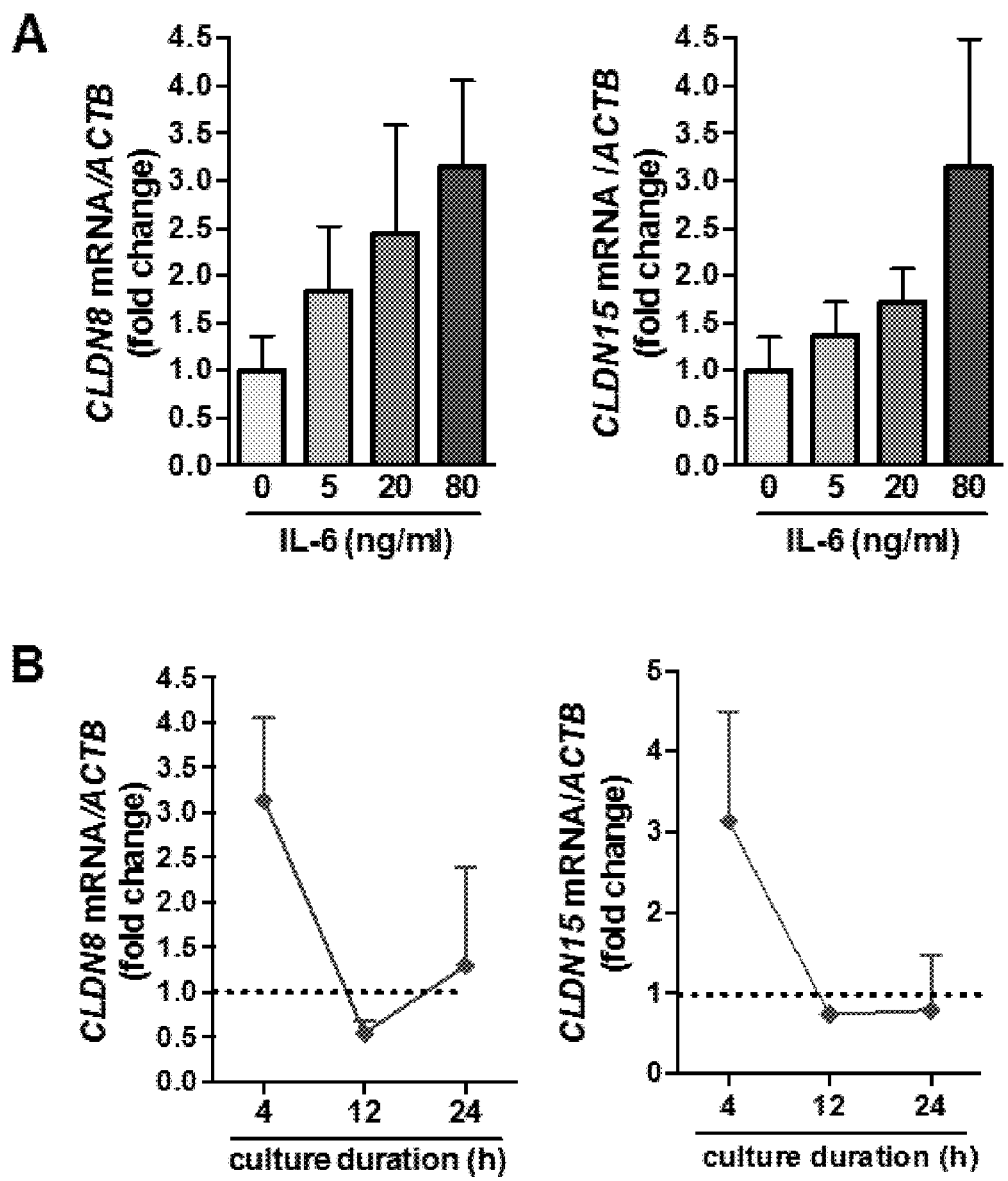
FIG. 7. IL-6 modulates colon expression of claudin 8 and 15.
Figure 7:
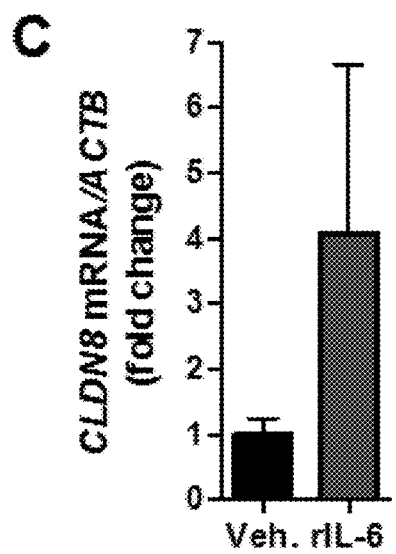
Figure 7:
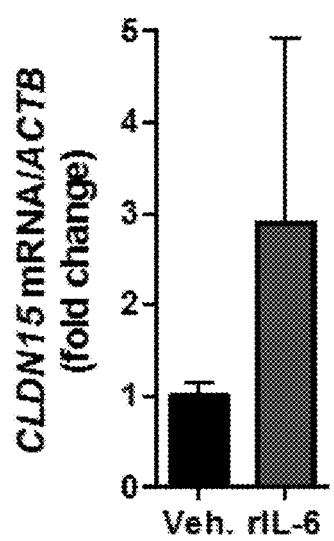

*B. fragilis* treatment also restored MIA-associated increases in colon IL-6 mRNA and protein levels to those found in control mice (FIGS. 6E-F). Levels of other cytokines were altered in both colons and small intestines of MIA offspring (FIGS. 1D and 2C), but these were not affected by *B. fragilis* treatment, revealing specificity for IL-6. This finding is consistent with a critical role for IL-6 in the MIA model (Smith et al., 2007). Altered intestinal cytokine profiles may form the basis for the increased intestinal permeability observed in MIA offspring, as several cytokines including IL-6 are reported to modulate tight junctions and regulate intestinal barrier integrity (Suzuki et al., 2011; Turner, 2009). It was further found that recombinant IL-6 treatment can modulate colon levels of both claudin 8 and claudin 15 in vivo and in in vitro colon organ cultures (FIG. 7A-C), suggesting that *B. fragilis*-mediated restoration of colonic IL-6 levels could underlie its effects on gut permeability. Collectively, these findings demonstrate that *B. fragilis* treatment of MIA offspring reverses defects in GI barrier integrity, and corrects alterations in tight junction and cytokine expression.

Example 4

*B. fragilis* Treatment Restores Microbiota Changes in MIA Offspring

Figure 8:
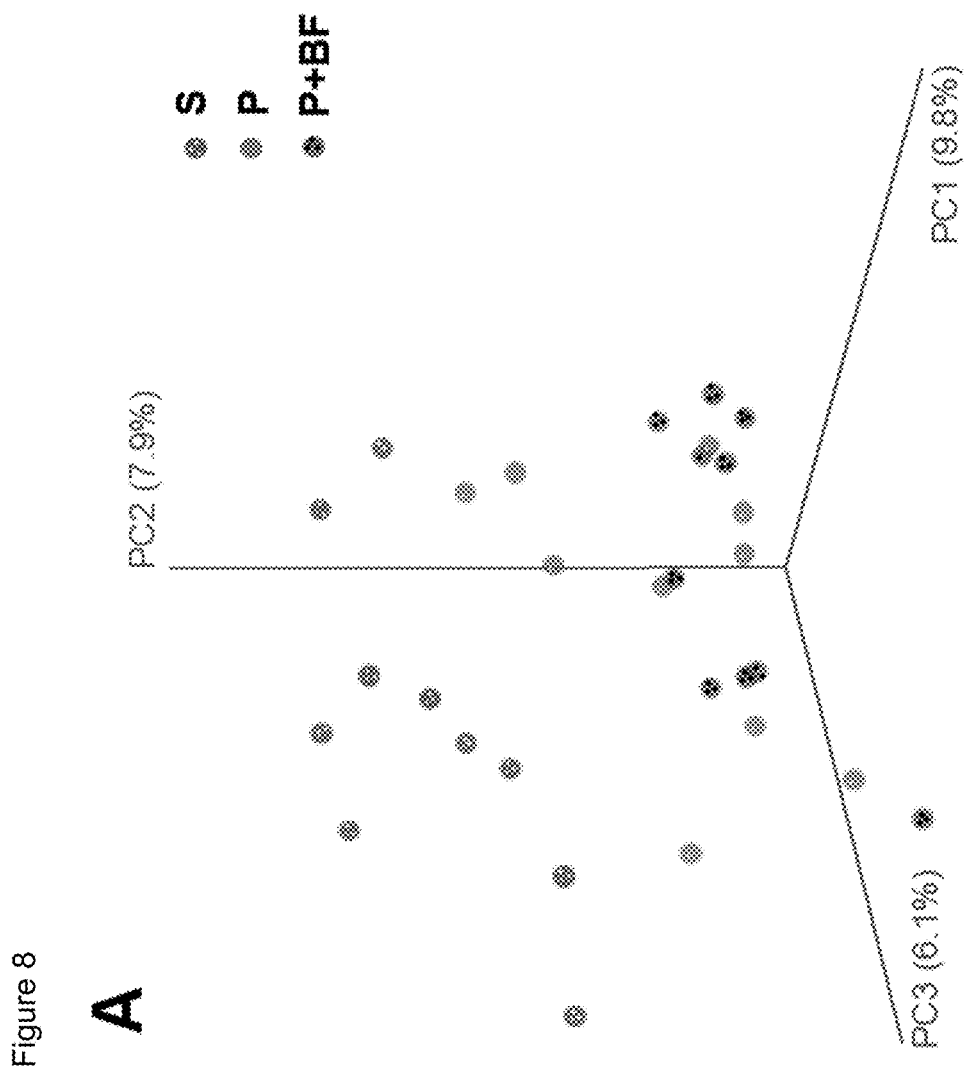
FIG. 8. B. fragilis treatment alters the composition of the intestinal microbiota and corrects species-level abnormalities in MIA offspring.
Figure 8:
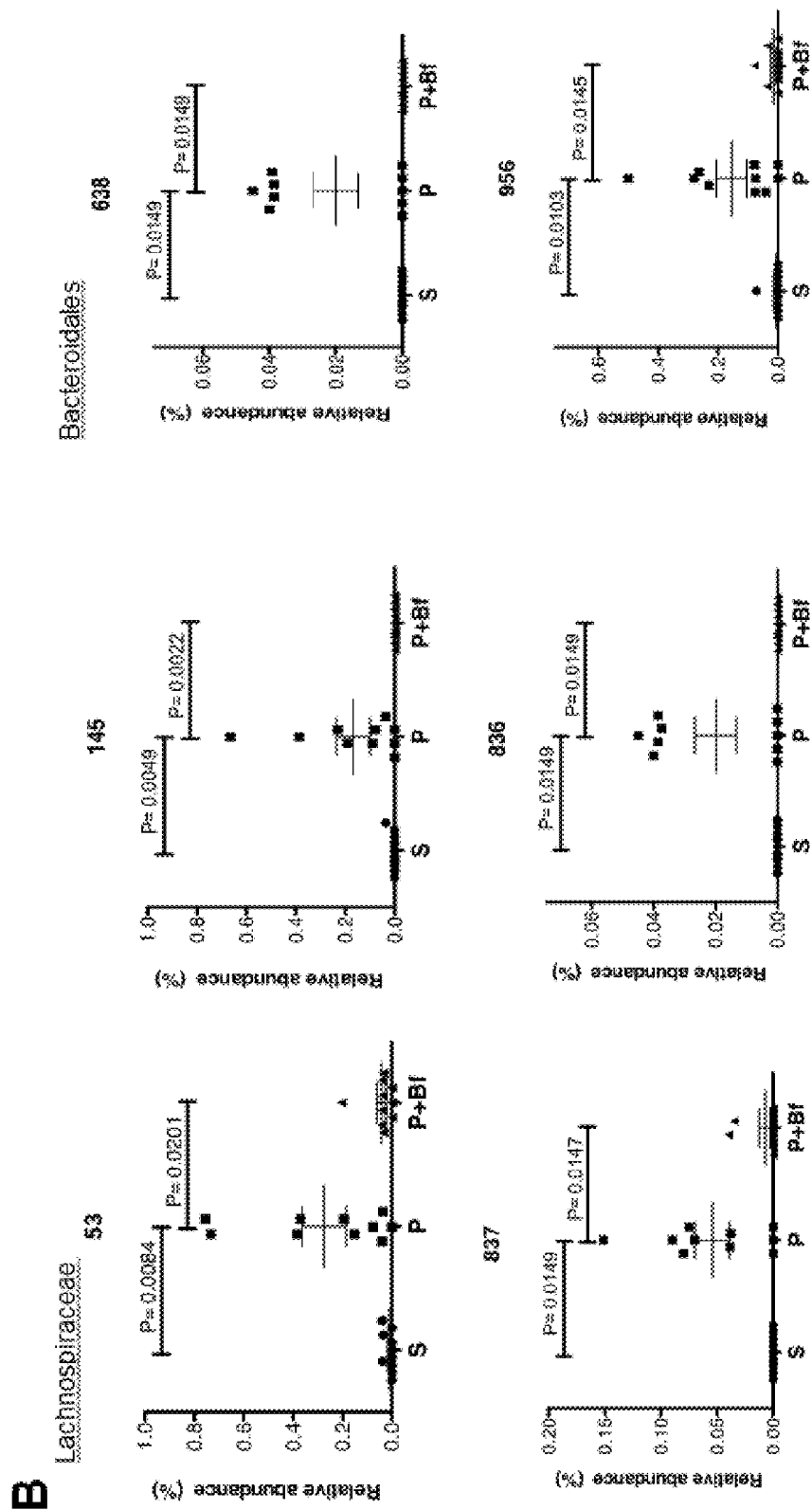
Figure 9:
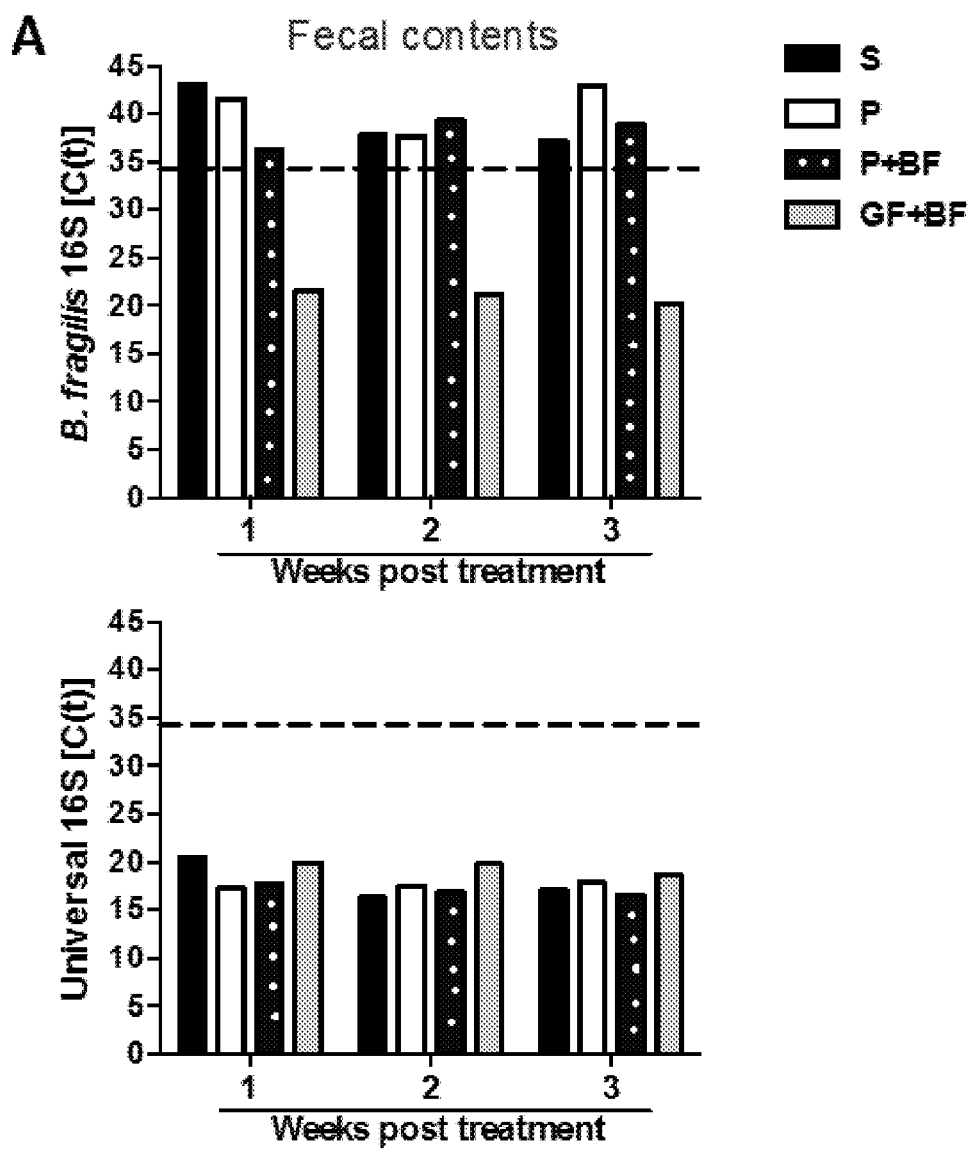
FIG. 9. There is no evidence for persistent colonization of B. fragilis after treatment of MIA offspring.
Figure 9:
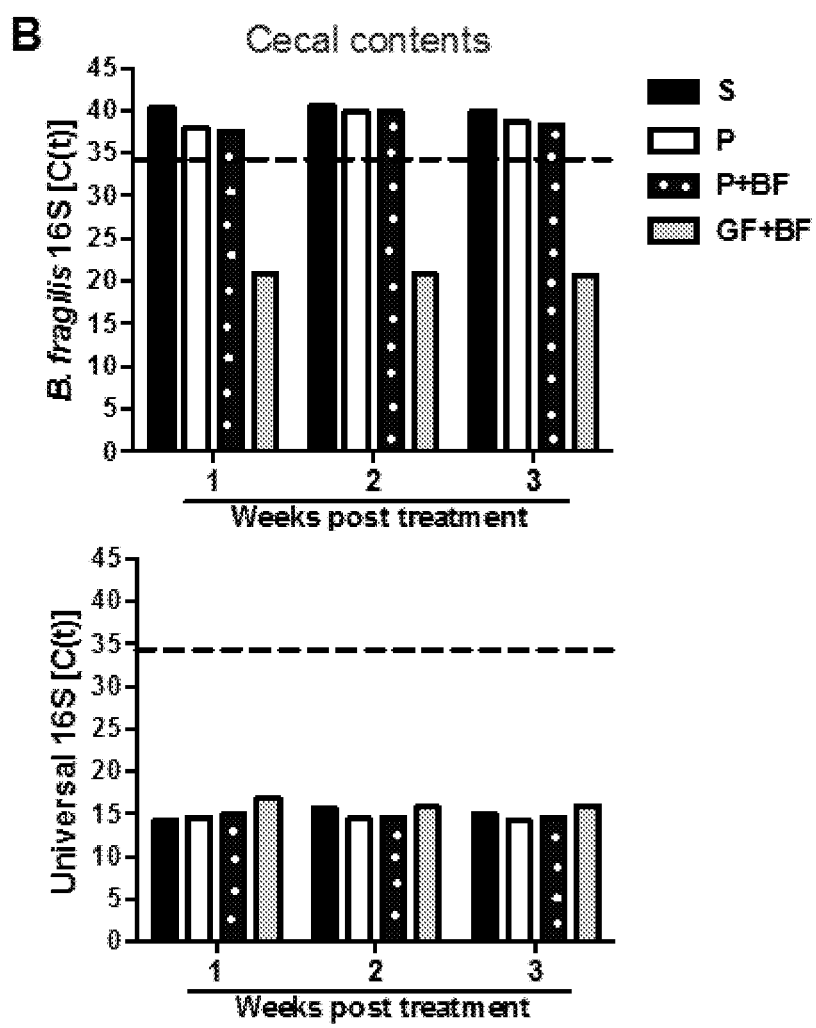

In addition to ameliorating GI physiology in MIA offspring, *B. fragilis* treatment induces long-term effects on the composition of the intestinal microbiota. No significant differences were observed at the global level by PCoA (ANOSIM R=0.0060 p=0.4470) or in microbiota richness (PD: p=0.2980, Observed Species: p=0.5440) and evenness (Gini: p=0.6110, Simpson Evenness: p=0.5600; FIGS. 8A, 4A-B). However, corrective effects of *B. fragilis* treatment were apparent upon evaluating specific key OTUs that discriminate adult MIA offspring from controls (FIG. 8B). Specifically, MIA offspring treated with *B. fragilis* displayed complete restoration in the relative abundance of 6 out of the 67 OTUs discriminate MIA from control offspring (28 other OTUs, not identified as discriminatory between MIA and control offspring, could discriminate between MIA offspring and those that have been treated with *B. fragilis*). These 6 OTUs are taxonomically assigned as unclassified Bacteroidia and Clostridia of the family Lachnospiraceae (FIG. 8B). Notably, these alterations occurred in the absence of persistent colonization of *B. fragilis*, which remains undetectable in fecal and cecal samples isolated from treated MIA offspring, as assessed by quantitative real-time PCR (FIG. 9A-B). Interestingly, 4 of the 10 Lachnospiraceae elevated in MIA offspring were corrected by *B. fragilis* treatment (FIGS. 5D and 8A-C). In addition, *B. fragilis* treatment restored the relative abundance of 2 Bacteroidia OTUs to levels observed in controls (FIG. 8B). Phylogenetic reconstruction of the 6 OTUs that were altered by MIA and restored by *B. fragilis* treatment reveals that the two Bacteroidia OTUs cluster together into a monophyletic group (FIG. 8D). In addition, the Lachnospiraceae OTUs that were significantly altered by MIA and corrected by *B. fragilis* cluster into 2 separate monophyletic groups (FIG. 8D). These results indicate that, although treatment of MIA offspring with *B. fragilis* may not lead to persistent colonization of *B. fragilis* itself, it can correct the relative abundance of specific groups of related microbes of the Lachnospiraceae family as well as unclassified Bacteriodales.

Altogether, this example demonstrates that treatment of MIA offspring with *B. fragilis* can ameliorate particular changes involved in MIA-associated dysbiosis of the commensal microbiota and correct GI abnormalities similar to those observed in subsets of autistic individuals.

Example 5

*B. fragilis* Treatment Corrects ASD-Related Behavioral Abnormalities

To explore the potential impact of GI dysfunction on core ASD behavioral abnormalities, the question whether *B. fragilis* treatment impacts ASD-related behaviors in MIA offspring was investigated.

Adult MIA offspring were found to display cardinal behavioral features of ASD in a variety of behavioral assays. Open field exploration involves mapping an animal's movement in an open arena to measure of locomotion and anxiety (Bailey and Crawley, 2009). MIA offspring displayed decreased entries and time spent in the center of the arena, but no difference in the total distance traveled, which is indicative of anxiety-like behavior (FIG. 10A; compare saline (S) to poly(I:C) (P)). The pre-pulse inhibition (PPI) task measures the ability of an animal to inhibit its startle in response to an acoustic tone ("pulse") when it is preceded by a lower-intensity stimulus ("pre-pulse"). Deficiencies in PPI are a measure of impaired sensorimotor gating, and are observed in several neurodevelopmental disorders, including autism (Perry et al., 2007). MIA offspring exhibited decreased PPI in response to 5 or 15 db pre-pulses (FIG. 10B). The marble burying test measures the propensity of mice to engage repetitively in a natural digging behavior that is not confounded by anxiety (Thomas et al., 2009). MIA offspring displayed increased stereotyped marble burying compared to controls (FIG. 10C), which models repetitive behavior as a core ASD symptom. Ultrasonic vocalizations are used to measure communication by mice, given that several types of calls are produced and used in structured motifs that vary across different social paradigms (Grimsley et al., 2011; Scattoni et al., 2011; Silverman et al., 2010b). MIA offspring exhibited ASD-related deficits in communication, as indicated by reduced number and duration of ultrasonic vocalizations produced in response to a social encounter (FIG. 10D). Finally, the three-chamber social test is used to measure ASD-related impairments in social interaction (Silverman et al., 2010a). Sociability is exemplified by a mouse's preference to interact with a novel mouse over a novel object, while social novelty (social preference) is characterized by preference to interact with an unfamiliar versus a familiar mouse. MIA offspring exhibited deficits in both sociability and social preference (FIG. 10E-F). Altogether, there behavioral assays evaluate the cardinal diagnostic symptoms of ASD, in addition to ASD-associated anxiety and deficient sensorimotor gating, have been broadly used to phenotype ASD mouse models (Han et al., 2012; Novarino et al., 2012; Schmeisser et al., 2012; Silverman et al., 2010a; Tabuchi et al., 2007; Tsai et al., 2012; Won et al., 2012).

Remarkably, oral treatment with *B. fragilis* ameliorated many of these ASD-related behavioral abnormalities. *B. fragilis*-treated MIA offspring did not exhibit anxiety-like behavior in the open field (FIG. 10A; compare poly(I:C) (P) to poly(I:C)+*B. fragilis* (P+BF)), as shown by restoration in the number of center entries and duration of time spent in the center of the open field. *B. fragilis* improved sensorimotor gating in MIA offspring, as indicated by increased combined PPI in response to 5 and 15 db pre-pulses (FIG. 10B), with no significant effect on the intensity of startle to the acoustic stimulus (data not shown). *B. fragilis*-treated MIA offspring also exhibited decreased levels of stereotyped marble burying and restored communicative behavior, as illustrated by increased number and duration of ultrasonic vocalizations (FIG. 10C-D). Interestingly, *B. fragilis* treatment raised the duration per call produced by MIA offspring to levels that exceed that observed in saline controls (FIG. 10D), suggesting that despite normalization of the propensity to communicate (no difference compared to controls in the number of calls produced), there is a qualitative difference in the types of calls generated with enrichment of longer syllables.

Although *B. fragilis*-treated MIA offspring exhibited improved communicative, repetitive, anxiety-like and sensorimotor behavior, they retain deficits in sociability and social preference (FIG. 10E). Interestingly, this parallels the inability to improve social behavior by administration of risperidone to ASD individuals (Canitano and Scandurra, 2008) and to CNTNAP2 knockout mice, a genetic mouse model for ASD (Penagarikano et al., 2011). These data indicate that there are fundamental differences in the circuitry or circuit plasticity governing social behavior as compared to the other behaviors, and that *B. fragilis* treatment modulates specific brain circuits during amelioration of ASD-related behavioral defects in MIA offspring.

In addition, behavioral improvement in response to *B. fragilis* treatment was not associated with changes in systemic immunity in MIA offspring (FIGS. 3A-C) and was not dependent on polysaccharide A (PSA), a molecule previously identified to confer immunomodulatory effects by *B. fragilis* (FIG. 3E) (Mazmanian et al., 2008; Ochoa-Reparaz et al., 2010; Round and Mazmanian, 2010). Furthermore, amelioration of behavior is not specific to *B. fragilis*, as similar treatment with *Bacteroides* thetaiotaomicron, also significantly improves anxiety-like, repetitive and communicative behavior in MIA offspring (FIGS. 11A-D). This is consistent with our finding that *B. fragilis* treatment does not lead to persistent colonization of *B. fragilis* in the GI tract (FIGS. 9A-B), and may be acting by causing long-term shifts in the resident microbiota (see FIG. 4).

Example 6

The Serum Metabolome is Modulated by MIA and *B. fragilis* Treatment

Metabolomic studies have shown that gut microbial products are found in many extra-intestinal tissues, and molecules derived from the microbiota may influence metabolic, immunologic and behavioral phenotypes in mice and humans (Bercik et al., 2011; Blumberg and Powrie, 2012; Hooper et al., 2012; MacFabe, 2012; Matsumoto et al., 2012; Nicholson et al., 2012). In this example, potential was examined.

Figure 12B:
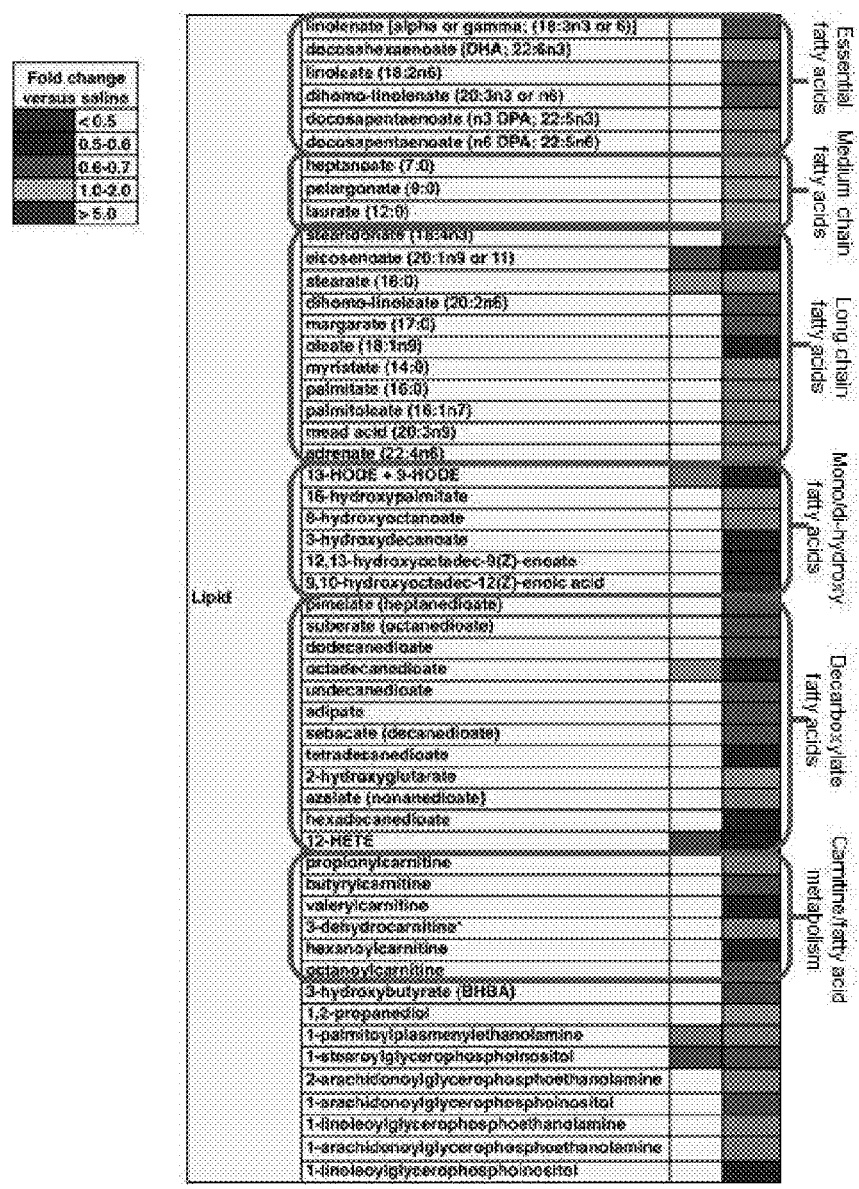

Gas chromatography/liquid chromatography with mass spectrometry (GC/LC-MS)-based metabolomic profiling was used to identify MIA-associated changes in serum metabolites. 2,400 metabolites were assayed and of these, 322 metabolites, spanning amino acid (94), peptide (15), carbohydrate (22), energy (10), lipid (128), nucleotide (23), xenobiotic (19) and cofactor and vitamin (11) super pathways were detected in sera from adult mice (Table 4)Interestingly, MIA leads to statistically significant alterations in 8% of all serum metabolites detected (Table 3). Furthermore, postnatal *B. fragilis* treatment has a significant effect on the serum metabolome, altering 34% of all metabolites detected (Table 4 and FIG. 12). .

TABLE 3

Serum Metabolites Altered in Adult Saline versus Poly(I:C) Offspring

| Super Pathway | Sub-pathway | Metabolite | Fold Change | p-value |
|---|---|---|---|---|
| Amino acid | Glycine, serine and threonine metabolism | N-acetylserine | 0.73 | 0.0354 |
| Amino acid | Alanine and aspartate metabolism | beta-alanine | 0.46 | 0.0500 |
| Amino acid | Glutamate metabolism | glutamine | 1.2 | 0.0173 |
| Amino acid | Histidine metabolism | transurocanate | 1.71 | 0.0240 |
| Amino acid | Histidine metabolism | imidazole propionate | 1.35 | 0.0161 |
| Amino acid | Phenylalanine and tyrosine metabolism | phenylacetylglycine | 0.71 | 0.0821 |
| Amino acid | Phenylalanine and tyrosine metabolism | phenol sulfate | 0.68 | 0.0092 |
| Amino acid | Tryptophan metabolism | indolepyruvate | 1.57 | 0.0240 |
| Amino acid | Tryptophan metabolism | serotonin | 1.15 | 0.0804 |
| Amino acid | Valine, leucine and isoleucine metabolism | 3-methyl-2-oxovalerate | 0.75 | 0.0152 |
| Amino acid | Valine, leucine and isoleucine metabolism | 4-methyl-2-oxopentaoate | 0.7 | 0.0072 |
| Amino acid | Cysteine, methionine, SAM, taurine metabolism | cysteine | 0.73 | 0.0582 |
| Amino acid | Urea cycle; arginine-, proline-, metabolism | arginine | 0.87 | 0.0761 |
| Amino acid | Urea cycle; arginine-, proline-, metabolism | ornithine | 0.68 | 0.0956 |
| Amino acid | Polyamine metabolism | 5-methylthioadenosine | 1.34 | 0.0425 |
| Peptide | Dipeptide | glycylvaline | 0.48 | 0.0077 |
| Peptide | Fibrinogen cleavage peptide | TDTEDKGEFLSEGGGVR | 1.8 | 0.0567 |
| Carbohydrate | Glycolysis, gluconeogenesis, pyruvate metabolism | 3-phosphoglycerate | 0.51 | 0.0265 |
| Carbohydrate | Glycolysis, gluconeogenesis, pyruvate metabolism | phosphoenolpyruvate | 0.56 | 0.0344 |
| Carbohydrate | Nucleotide sugars, pentose metabolism | ribose | 1.44 | 0.0499 |
| Carbohydrate | Nucleotide sugars, pentose metabolism | xylose | 1.34 | 0.0827 |
| Lipid | Essential fatty acid | docosapentaenoate (n3 DPA; 22:5n3) | 0.75 | 0.0988 |
| Lipid | Essential fatty acid | docosapentaenoate (n6 DPA; 22:5n6) | 0.83 | 0.0970 |
| Lipid | Essential fatty acid | docosahexaenoate (DHA; 22:6n3) | 0.8 | 0.0965 |
| Lipid | Long chain fatty acid | stearate | 0.88 | 0.0491 |
| Lipid | Long chain fatty acid | eicosenoate | 0.61 | 0.0151 |
| Lipid | Long chain fatty acid | dihomo-linoleate (20:2n6) | 0.79 | 0.0614 |
| Lipid | Long chain fatty acid | adrenate | 0.82 | 0.0923 |
| Lipid | Fatty acid, monohydroxy | 13-HODE + 9-HODE | 0.72 | 0.0489 |

TABLE 3-continued

Serum Metabolites Altered in Adult Saline versus Poly(I:C) Offspring

| Super Pathway | Sub-pathway | Metabolite | Fold Change | p-value |
|---|---|---|---|---|
| Lipid | Fatty acid, dicarboxylate | octadecanedioate | 0.83 | 0.0413 |
| Lipid | Eicosanoid | 12-HETE | 0.69 | 0.0152 |
| Lipid | Inositol metabolism | myo-inositol | 0.86 | 0.0817 |
| Lipid | Lysolipid | 1-palmitoylglycerophosphoethanolamine | 0.81 | 0.0868 |
| Lipid | Lysolipid | 1-oleoylglycerophosphoethanolamine | 0.7 | 0.0169 |
| Lipid | Lysolipid | 1-pentadecanoylglycerophosphocholine | 1.43 | 0.0505 |
| Lipid | Lysolipid | 1-palmitoleoylglycerophosphocholine | 1.49 | 0.0388 |
| Lipid | Lysolipid | 1-stearoylglycerophosphoinositol | 0.64 | 0.0059 |
| Lipid | Lysolipid | 1-palmitoylplasmenylethanolamine | 0.73 | 0.0399 |
| Cofactors and vitamins | Hemoglobin and porphyrin metabolism | bilirubin (E,E) | 2.68 | 0.0496 |
| Cofactors and vitamins | Pantothenate and CoA metabolism | pantothenate | 1.33 | 0.0643 |
| Cofactors and vitamins | Benzoate metabolism | 4-ethylphenylsulfate | 46.39 | 0.0359 |
| Cofactors and vitamins | Chemical | glycolate (hydroxyacetate) | 1.17 | 0.0498 |
| Cofactors and vitamins | Food component/Plant | ergothioneine | 0.72 | 0.0688 |
| Cofactors and vitamins | Food component/Plant | equol sulfate | 0.78 | 0.0315 |

Summary of notable changes ($p < 0.10$) in levels of serum metabolites in 10-week old offspring of poly(I:C)-injected mothers versus controls. Serum samples were extracted and analyzed by GC/LC-MS by Metabolon, Inc. Data were analyzed using two-way ANOVA with contrasts. Additional details are provided in Experimental Procedures.

TABLE 4

Serum Metabolites Altered in Saline and Poly(I:C) Offspring after *B. fragilis* Treatment

| Super Pathway | Sub Pathway | Biochemical Name | Platform | I:C-Bfrag CON |
|---|---|---|---|---|
| | | sarcosine (N-Methylglycine) | GC/MS | 0.64 |
| | Alanine and aspartate metabolism | aspartate | GC/MS | 0.76 |
| | | 3-ureidopropionate | LC/MS pos | 0.64 |
| | Lysine metabolism | glutarate (pentanedioate) | GC/MS | 0.78 |
| | | tyrosine | LC/MS pos | 0.85 |
| | | 3-(4-hydroxyphenyl)lactate | LC/MS neg | 0.81 |
| | | 3-phenylpropionate (hydrocinnamate) | LC/MS neg | 0.60 |
| | | serotonin (5HT) | LC/MS pos | 1.26 |
| | Valine, leucine and isoleucine metabolism | 3-methyl-2-oxobutyrate | LC/MS neg | 0.68 |
| | | 3-methyl-2-oxovalerate | LC/MS neg | 0.67 |
| | | 4-methyl-2-oxopentanoate | LC/MS neg | 0.63 |
| | | isobutyrylcarnitine | LC/MS pos | 0.68 |
| | | 2-methylbutyroylcarnitine | LC/MS pos | 0.66 |
| | | isovalerylcarnitine | LC/MS pos | 0.76 |
| | | 2-hydroxybutyrate (AHB) | GC/MS | 0.64 |
| | Urea cycle; arginine-, proline-, metabolism | arginine | LC/MS pos | 0.86 |
| | | ornithine | GC/MS | 0.66 |
| | Butanoate metabolism | 2-aminobutyrate | LC/MS pos | 0.76 |
| | Guanidino and acetamido metabolism | 4-guanidinobutanoate | LC/MS pos | 0.65 |
| | | 5-oxoproline | LC/MS neg | 0.80 |
| Peptide | Dipeptide | glycylvaline | LC/MS pos | 0.22 |
| | | gamma-glutamyltryptophan | LC/MS pos | 0.77 |
| | Fibrinogen cleavage peptide | TDTEDKGEFLSEGGGV* | LC/MS pos | 1.43 |
| | | TDTEDKGEFLSEGGGVR* | LC/MS pos | 3.46 |
| | | sorbitol | GC/MS | 0.63 |
| | | pyruvate | GC/MS | 0.58 |
| | | ribitol | GC/MS | 0.74 |
| | | ribose | GC/MS | 1.97 |
| | | ribulose | GC/MS | 0.68 |
| | | xylitol | GC/MS | 1.62 |

TABLE 4-continued

Serum Metabolites Altered in Saline and Poly(I:C) Offspring after *B. fragilis* Treatment

| Super Pathway | Sub Pathway | Biochemical Name | Platform | I:C-Bfrag CON |
|---|---|---|---|---|
| Energy | Krebs cycle | citrate | GC/MS | 0.80 |
| | | fumarate | GC/MS | 0.64 |
| | | malate | GC/MS | 0.69 |
| Lipid | Essential fatty acid | linoleate (18:2n6) | LC/MS neg | 0.64 |
| | | linolenate [alpha or gamma; (18:3n3 or 6)] | LC/MS neg | 0.62 |
| | | dihomo-linolenate (20:3n3 or n6) | LC/MS neg | 0.69 |
| | | docosapentaenoate (n3 DPA; 22:5n3) | LC/MS neg | 0.72 |
| | | docosapentaenoate (n6 DPA; 22:5n6) | LC/MS neg | 0.70 |
| | | docosahexaenoate (DHA; 22:6n3) | LC/MS neg | 0.77 |
| | | heptanoate (7:0) | LC/MS neg | 0.81 |
| | | pelargonate (9:0) | LC/MS neg | 0.81 |
| | | laurate (12:0) | LC/MS neg | 0.85 |
| | Long chain fatty acid | myristate (14:0) | GC/MS | 0.70 |
| | | palmitate (16:0) | LC/MS neg | 0.72 |
| | | palmitoleate (16:1n7) | GC/MS | 0.70 |
| | | margarate (17:0) | GC/MS | 0.60 |
| | | stearate (18:0) | LC/MS neg | 0.75 |
| | | oleate (18:1n9) | GC/MS | 0.56 |
| | | stearidonate (18:4n3) | LC/MS neg | 0.66 |
| | | eicosenoate (20:1n9 or 11) | LC/MS neg | 0.59 |
| | | dihomo-linoleate (20:2n6) | LC/MS neg | 0.63 |
| | | mead acid (20:3n9) | LC/MS neg | 0.74 |
| | | adrenate (22:4n6) | LC/MS neg | 0.75 |
| | | 8-hydroxyoctanoate | LC/MS neg | 0.72 |
| | | 3-hydroxydecanoate | LC/MS neg | 0.51 |
| | | 16-hydroxypalmitate | LC/MS neg | 0.70 |
| | | 13-HODE + 9-HODE | LC/MS neg | 0.50 |
| | Fatty acid, dihydroxy | 12,13-hydroxyoctadec-9(Z)-enoate | LC/MS neg | 0.54 |
| | | 9,10-hydroxyoctadec-12(Z)-enoic acid | LC/MS neg | 0.48 |
| | Fatty acid, dicarboxylate | adipate | GC/MS | 0.62 |
| | | 2-hydroxyglutarate | GC/MS | 0.83 |
| | | pimelate (heptanedioate) | GC/MS | 0.61 |
| | | suberate (octanedioate) | LC/MS pos | 0.69 |
| | | sebacate (decanedioate) | LC/MS neg | 0.64 |
| | | azelate (nonanedioate) | LC/MS neg | 0.72 |
| | | dodecanedioate | LC/MS neg | 0.65 |
| | | tetradecanedioate | LC/MS neg | 0.57 |
| | | hexadecanedioate | LC/MS neg | 0.54 |
| | | octadecanedioate | LC/MS neg | 0.53 |
| | | undecanedioate | LC/MS neg | 0.66 |
| | Eicosanoid | 12-HETE | LC/MS neg | 0.57 |
| | Fatty acid metabolism (also BCAA metabolism) | propionylcarnitine | LC/MS pos | 0.79 |
| | | butyrylcarnitine | LC/MS pos | 0.64 |
| | Fatty acid metabolism | valerylcarnitine | LC/MS pos | 0.56 |
| | | 3-dehydrocarnitine* | LC/MS pos | 0.71 |
| | | hexanoylcarnitine | LC/MS pos | 0.58 |
| | | octanoylcarnitine | LC/MS pos | 0.69 |
| | | choline | LC/MS pos | 0.79 |
| | | chiro-inositol | GC/MS | 0.66 |
| | | pinitol | GC/MS | 0.61 |
| | Ketone bodies | 3-hydroxybutyrate (BHBA) | GC/MS | 0.66 |
| | | 1,2-propanediol | GC/MS | 0.83 |
| | | 1-linoleoylglycerophosphoethanolamine* | LC/MS neg | 0.71 |
| | | 1-arachidonoylglycerophosphoethanolamine* | LC/MS neg | 0.76 |
| | | 2-arachidonoylglycerophosphoethanolamine* | LC/MS neg | 0.78 |
| | | 1-stearoylglycerophosphoinositol | LC/MS neg | 0.66 |
| | | 1-linoleoylglycerophosphoinositol* | LC/MS neg | 0.59 |
| | | 1-arachidonoylglycerophosphoinositol* | LC/MS neg | 0.61 |
| | | 1-palmitoylplasmenylethanolamine* | LC/MS neg | 0.72 |
| | | hypoxanthine | GC/MS | 8.55 |
| | | inosine | LC/MS neg | 8.36 |
| | | adenosine | LC/MS pos | 5.63 |
| | | adenosine 5'-monophosphate (AMP) | LC/MS pos | 20.92 |
| | Purine metabolism, guanine containing | guanosine 5'- monophosphate (5'-GMP) | LC/MS pos | 5.74 |
| | Purine metabolism, urate metabolism | urate | LC/MS neg | 0.84 |
| | | 2'-deoxycytidine | LC/MS pos | 1.32 |

TABLE 4-continued

Serum Metabolites Altered in Saline and Poly(I:C) Offspring after *B. fragilis* Treatment

| Super Pathway | Sub Pathway | Biochemical Name | Platform | I:C-Bfrag CON |
|---|---|---|---|---|
| | Pyrimidine metabolism, uracil containing | uracil | GC/MS | 0.64 |
| | | pseudouridine | LC/MS neg | 0.89 |
| | Nicotinate and nicotinamide metabolism | nicotinamide | LC/MS pos | 0.79 |
| | | catechol sulfate | LC/MS neg | 0.77 |
| | Drug | salicylate | LC/MS neg | 0.68 |
| | | equol sulfate | LC/MS neg | 0.70 |
| | Sugar, sugar substitute, starch | erythritol | GC/MS | 0.79 |

Example 7

*B. fragilis* Treatment Corrects Levels of MIA-Induced Serum Metabolites

This examples shows *B. fragilis*-mediated improvement of intestinal barrier integrity prevents alterations in serum metabolite levels.

Figure 13:
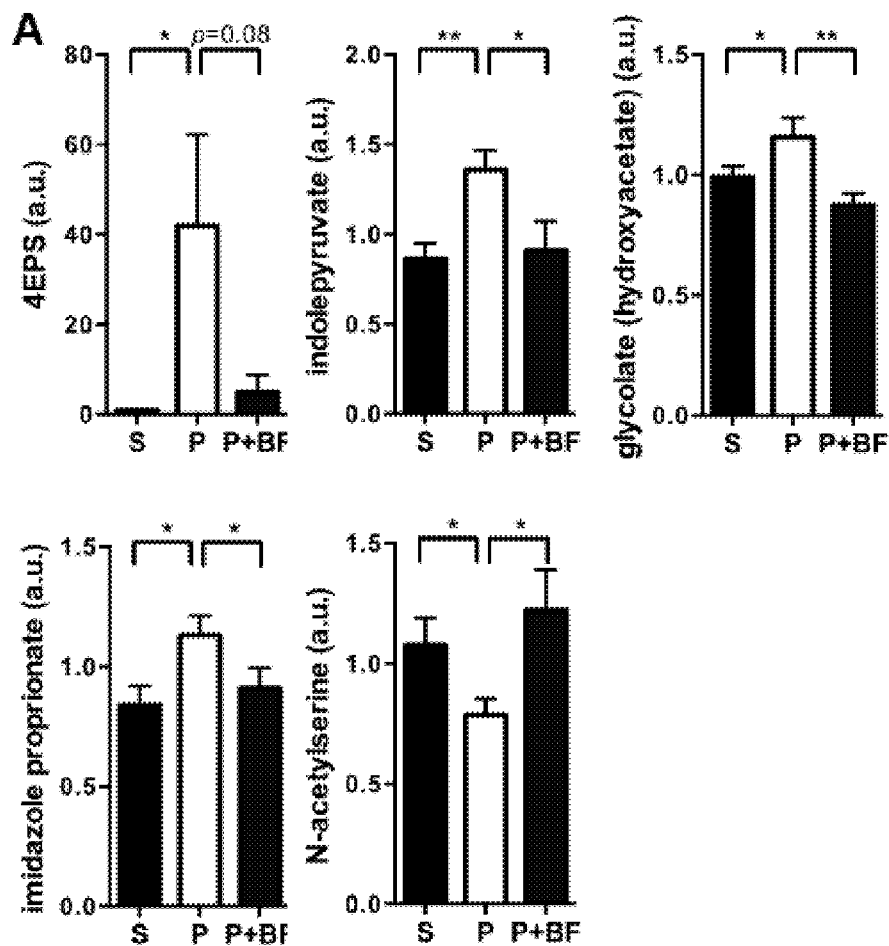
FIG. 13. B. fragilis treatment corrects MIA-induced alterations in 4-ethylphenylsulfate (4EPS), a microbe-dependent metabolite that sufficiently induces anxiety-like behavior.
Figure 13:
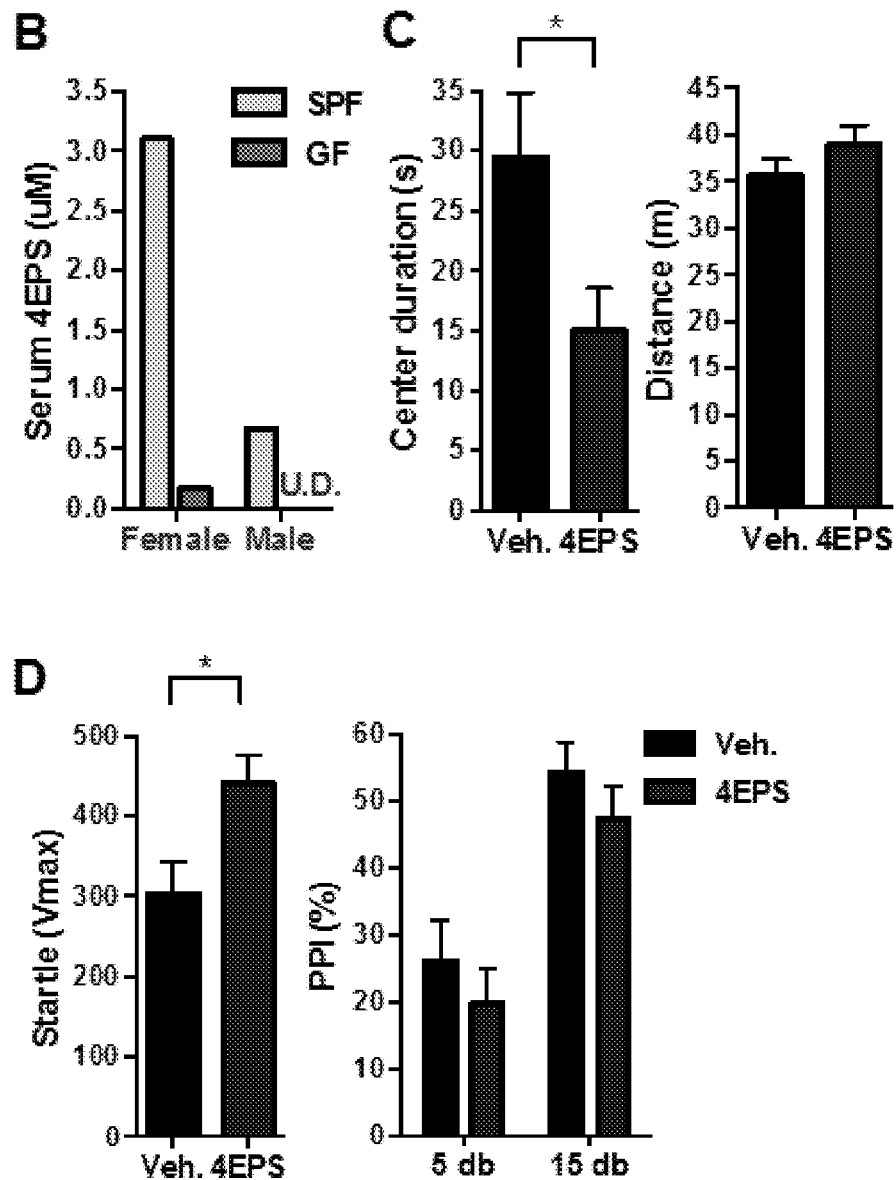
Figure 14A:
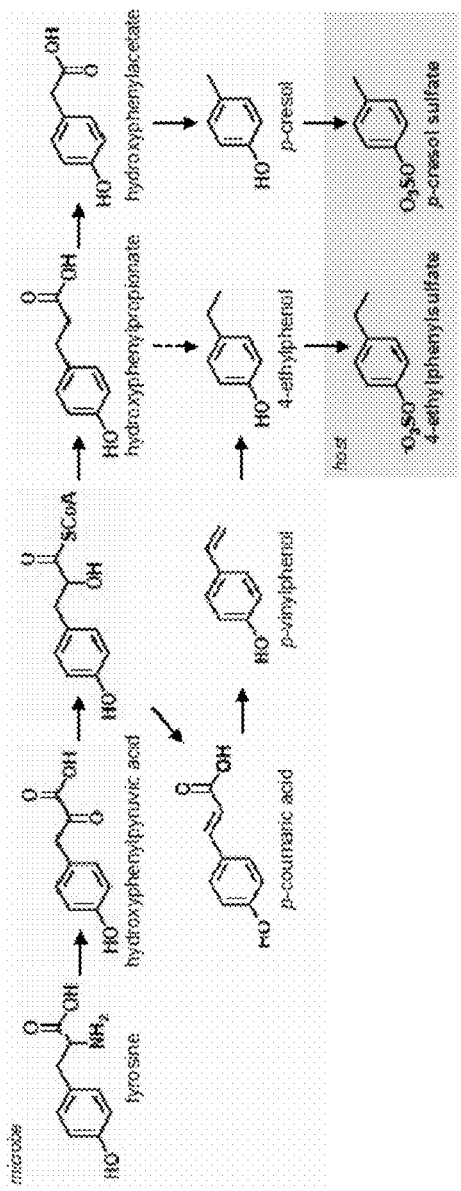
FIGS. 14A-B. Synthesis of autism-associated metabolites by host-microbe interactions.

4-ethylphenylsulfate (4EPS), indolepyruvate and several other serum metabolites are significantly altered by MIA treatment and restored to control levels by *B. fragilis* treatment (FIG. 13A). MIA offspring displayed a striking, 46-fold increase in serum levels of 4-ethylphenylsulfate (4EPS) which was dramatically reduced by *B. fragilis* treatment (FIG. 13A). Moreover, it was found that compared to conventionally colonized mice, germ-free mice display nearly undetectable levels of serum 4EPS, indicating that serum 4EPS is derived from, or critically modulated by, the commensal microbiota (FIG. 13B). 4EPS has been suggested to be a uremic toxin, as is p-cresol (4-methylphenol), a related metabolite identified as a possible urinary biomarker for human autism (Altieri et al., 2011; Persico and Napolioni, 2013). MIA offspring also exhibited elevated levels of serum p-cresol, although the increase did not reach statistical significance (Table 4). The fact that 4EPS shares close structural similarity to the toxic sulfated form of p-cresol (4-methylphenylsulfate; 4 MPS) is intriguing as the two metabolites may exhibit functional overlap (FIG. 14A) and link metabolite abnormalities seen in the MIA model to those observed in human ASD.

Figure 14B:
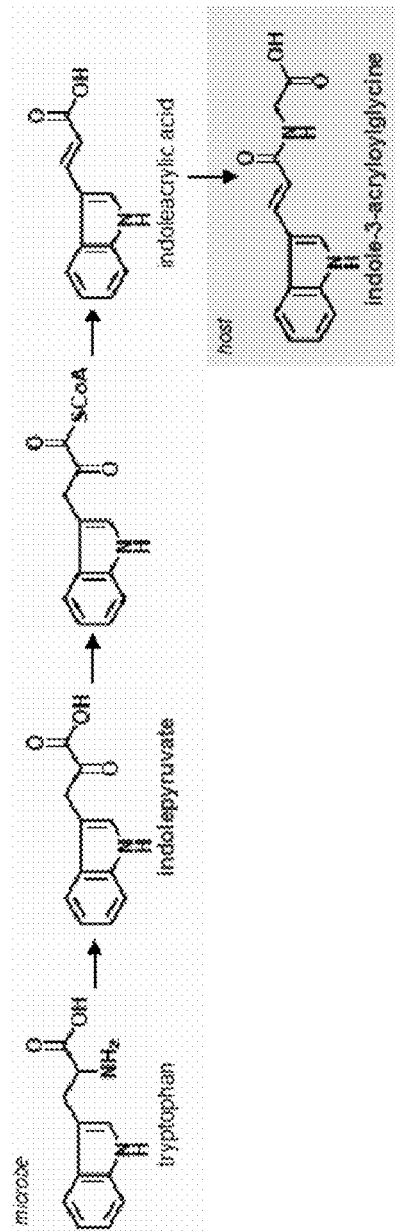

In addition to 4EPS, MIA offspring displayed significantly increased levels of serum indolepyruvate, a key molecule of the tryptophan metabolism pathway, which was restored to control levels by *B. fragilis* treatment (FIG. 13A). Indolepyruvate is generated by tryptophan catabolism and, like 4EPS, indolepyruvate is believed to be produced by gut microbes (Smith and Macfarlane, 1997) (FIG. 14B). Moreover, the elevation in serum indolepyruvate observed in MIA offspring is analogous to the increase in another major tryptophan metabolite observed in human autism, indolyl-3-acryloylglycine (IAG), which was suggested to be a urinary biomarker for ASD (Bull et al., 2003). Interestingly, IAG is involved in GI homeostasis and is produced by bacterial tryptophan metabolism (Keszthelyi et al., 2009). It is notable that MIA offspring exhibited increased levels of serum serotonin ($0.05 < P < 0.10$), which reflects an alteration in another pathway of tryptophan metabolism and is reminiscent of the hyperserotonemia endophenotype of autism (Mulder et al., 2004). Importantly, the commensal microbiota is known to impact serum levels of indole-containing tryptophan metabolites and serotonin (Wikoff et al., 2009). MIA also led to altered serum glycolate, imidazole propionate and N-acetylserine levels (FIG. 13A), which were corrected by *B. fragilis* treatment.

This example demonstrates that specific metabolites are altered in MIA offspring and normalized by *B. fragilis* treatment.

Example 8

A Serum Metabolite Induces ASD-Related Behaviors

MIA-dependent increases in the systemic bioavailability of specific metabolites, and restoration by *B. fragilis*, suggest that these molecules play a causative role in ASD-related behaviors in MIA offspring. This example examined whether experimentally increasing serum 4EPS, the most dramatic of all metabolites affected by gut bacteria, is sufficient to cause any ASD-related behavioral abnormalities in naïve mice.

4EPS was chemically synthesized by treatment of 4-ethylphenol with sulfur trioxide-pyridine complex, which, following ion exchange, yields 4EPS potassium salt (FIGS. 15A-C) (Burlingham et al., 2003; Grimes, 1959). Mice were intraperitoneally treated with 4EPS or saline vehicle daily, from 3 weeks of age (when increased gut permeability was detected in MIA offspring, see FIG. 1A) to 6 weeks of age (when behavior testing began).

Figure 15D:
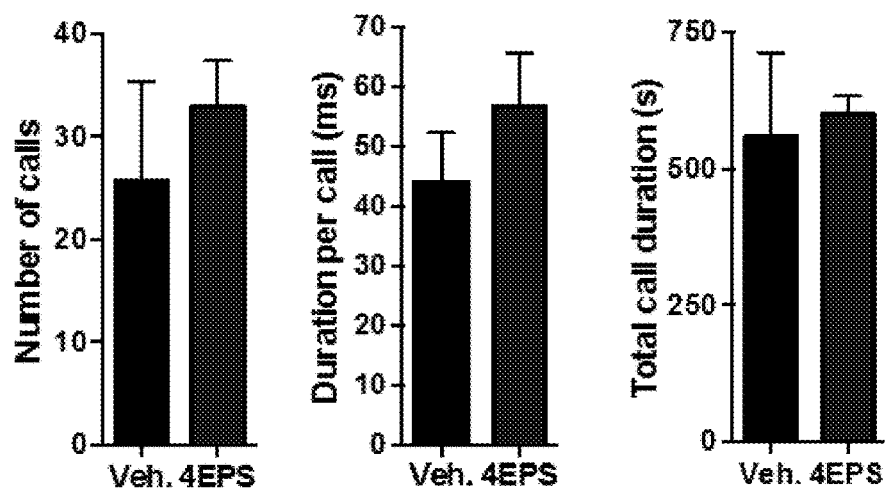
Figure 15E:
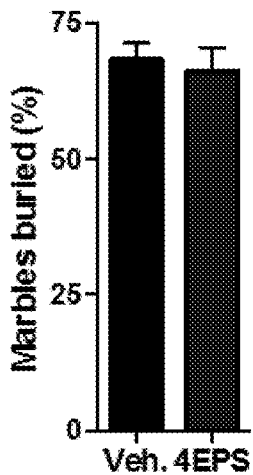

Remarkably, systemic administration of 4EPS to naïve wild-type mice was sufficient to induce anxiety-like behavior similar to that observed in MIA offspring (FIG. 13C). Relative to vehicle-treated controls, mice exposed to 4EPS traveled comparable distances in the open field but spent less time in the center arena (FIG. 13C). Notably, vehicle-treated controls exhibited symptoms of anxiety-like behavior compared to untreated saline offspring (center entries: 14.5±1.1 versus 23.7±1.4; center duration (s): 29.4±5.4 versus 46.4±4.2; distance (m): 35.6±1.8 versus 37.6±1.0, comparing vehicle-treated mice (Veh.) in FIG. 13C to saline offspring (S) in FIG. 10A). This reflects the well-known effect of chronic stress (daily injection) on raising anxiety levels in mice and humans (Bailey and Crawley, 2009; Bourn et al., 2007). Also, in the PPI test, 4EPS-treated mice exhibited increased intensity of startle in response to the unconditioned primary stimulus, but no significant alterations in PPI (FIG. 13D), representing anxiety-associated potentiation of the startle reflex (Bourn et al., 2007). Also, there was no difference in weight between 4EPS- and control-treated mice, and thus, no confounding effect of body mass on measured startle intensity. Conversely, there were no significant differences between 4EPS-treated versus saline-treated mice in marble burying or USV behavior (FIGS. 15D and 15E), suggesting that elevating serum 4EPS levels specifically promoted anxiety-like behavior.

Example 9

Treatment of Autism Spectrum Disorder (ASD)

This example illustrates the treatment of a patient suffering from ASD.

A patient is identified as being suffering from ASD. The blood level of 4EPS in the subject is determined. A composition with *B. fragilis* is administered to the patient via oral administration. The administration of *B. fragilis* is expected to alter the blood level of 4EPS and composition of gut microbiota in the patient. It is also expected that the bacterial administration will relieve one or more symptoms of ASD, such as improve behavioral performance, in the patient.

Example 10

Treatment of Autism Spectrum Disorder (ASD)

This example illustrates the treatment of a patient suffering from ASD.

A patient is identified as being suffering from ASD. The urine level of 4-methylphenysulfate in the subject is determined. A composition with *B. fragilis* is administered to the patient via oral administration. The administration of *B. fragilis* is expected to alter the urine level of 4-methylphenysulfate and the composition of gut microbiota in the patient. It is also expect that the bacterial administration will relieve one or more symptoms of ASD, such as improve behavioral performance, in the patient.

The foregoing description and examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof. Although the present application has been described in detail above, it will be understood by one of ordinary skill in the art that various modifications can be made without departing from the spirit of the invention.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein including, but not limited to, published and unpublished patent applications, patents, text books, literature references, and the like, to the extent that they are not already, are hereby incorporated by reference in their entirety. To the extent that one or more of the incorporated literature and similar materials differ from or contradict the disclosure contained in the specification, including but not limited to defined terms, term usage, described techniques, or the like, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method for improving behavioral performance in a subject suffering from anxiety, Fragile X, Rett syndrome, obsessive compulsive disorder, attention deficit disorder, autistic disorder (classic autism), Asperger's disorder (Asperger syndrome), pervasive developmental disorder not otherwise specified (PDD-NOS), childhood disintegrative disorder (CDD), or autism spectrum disorder (ASD), the method comprising:
   (a) measuring the blood level of 4-ethylphenylsulfate in the subject,
   wherein the blood level of said 4-ethylphenylsulfate in the subject is altered relative to the blood level of said 4-ethylphenylsulfate observed in a subject not suffering from or showing symptoms of anxiety, Fragile X, Rett syndrome, obsessive compulsive disorder, attention deficit disorder, autistic disorder (classic autism), Asperger's disorder (Asperger syndrome), pervasive developmental disorder not otherwise specified (PDD-NOS), childhood disintegrative disorder (CDD), or ASD; and
   (b) administering a composition comprising bacteria selected from the group consisting of B. fragilis, B. thetaiotaomicron, and B. vulgatus to the subject until a correction of the deficiency in at least one of the one or more symptoms of anxiety, Fragile X, Rett syndrome, obsessive compulsive disorder, attention deficit disorder, autistic disorder (classic autism), Asperger's disorder (Asperger syndrome), pervasive developmental disorder not otherwise specified (PDD-NOS), childhood disintegrative disorder (CDD), or ASD is observed.

2. The method of claim 1, wherein the subject is a subject that suffers from anxiety or ASD.

3. The method of claim 2, wherein the subject suffers from ASD.

4. The method of claim 1, wherein the composition comprising bacteria is a probiotic composition, a nutraceutical, a pharmaceutical composition, or a mixture thereof.

5. The method of claim 1, further comprising administering one or more of Ruminococcaceae, Erysipelotrichaceae, and Alcaligenaceae bacteria to the subject.

6. The method of claim 1, further comprising determining a reference level of the 4-ethylphenylsulfate in non-autistic subjects.

7. The method of claim 1, further comprising determining at least one of the one or more behavior features of the subject prior to and after the composition comprising bacteria is administered to the subject.

8. The method of claim 7, wherein determining at least one of the one or more behavior features of the subject comprises using one or more of Autism Behavior Checklist (ABC), Autism diagnostic Interview-Revised (ADI-R), childhood autism Rating Scale (CARS), and Pre-Linguistic Autism Diagnostic Observation Schedule (PL-ADOS).

9. The method of claim 1, further comprising (c) comparing the subject's blood level of 4-ethylphenylsulfate after the composition is administered to a reference level of the 4-ethylphenylsulfate in non-autistic subjects,
   wherein the subject's blood level of 4-ethylphenylsulfate is about 80% to about 120% of the reference level.

10. The method of claim 1, wherein the deficiency in at least one of the one or more behavior features of the subject is determined using a test selected from the group consisting of Autism Behavior Checklist (ABC), Autism diagnostic Interview-Revised (ADI-R), childhood autism Rating Scale (CARS), Pre-Linguistic Autism Diagnostic Observation Schedule (PL-ADOS), and a combination thereof.

11. The method of claim 1, wherein administering the composition comprising bacteria to the subject is performed via oral administration, rectum administration, or intranasal administration.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tgattccgca tggtttcatt                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
cgacccatag agccttcatc                                                 20
```

```
<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
actcctacgg gaggcagcag t                                              21

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
attaccgcgg ctgctggc                                                  18

<210> SEQ ID NO 5
<211> LENGTH: 17
<212> TYPE: PRT
<213> ORGANISM: Artificial Sequence
<220> FEATURE:
<223> OTHER INFORMATION: ASD-related metabolite

<400> SEQUENCE: 5

Thr Asp Thr Glu Asp Lys Gly Glu Phe Leu Ser Glu Gly Gly Gly Val
 1               5                  10                  15

Arg
```